(12) United States Patent
Miller et al.

(10) Patent No.: US 7,517,880 B2
(45) Date of Patent: Apr. 14, 2009

(54) INHIBITION OF P38 KINASE USING SYMMETRICAL AND UNSYMMETRICAL DIPHENYL UREAS

(75) Inventors: Scott Miller, Exton, PA (US); Martin Osterhout, Raleigh, NC (US); Jacques Dumas, Orange, CT (US); Uday Khire, Hamden, CT (US); Timothy B. Lowinger, Nishinomiya (JP); William J. Scott, Guilford, CT (US); Roger A. Smith, Madison, CT (US); Jill E. Wood, Hamden, CT (US); David E. Gunn, Hamden, CT (US); Holia Hatoum-Mokdad, Hamden, CT (US); Marell Rodriguez, Guilford, CT (US); Robert Sibley, North Haven, CT (US); Ming Wang, Stanford, CT (US); Tiffany Turner, Pittsburgh, PA (US); Catherine Brennan, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 273 days.

(21) Appl. No.: 10/060,396

(22) Filed: Feb. 1, 2002

(65) Prior Publication Data

US 2004/0102636 A1    May 27, 2004

Related U.S. Application Data

(63) Continuation of application No. 09/458,015, filed on Dec. 10, 1999, now abandoned, which is a continuation of application No. 09/285,522, filed on Dec. 22, 1998, now abandoned.

(60) Provisional application No. 60/126,439, filed on Dec. 22, 1997.

(51) Int. Cl.
  *A61K 31/40* (2006.01)
  *A61K 31/44* (2006.01)
  *A61K 31/535* (2006.01)
  *C07D 333/22* (2006.01)
  *C07D 233/61* (2006.01)

(52) U.S. Cl. .............. 514/237.8; 514/345; 514/351; 514/357; 514/411; 514/425; 514/438; 514/571; 544/165; 546/290; 546/300; 548/169; 548/333.5; 548/435; 548/444; 548/567

(58) Field of Classification Search .............. 544/165; 546/300, 329, 290; 548/435, 444, 169, 567; 548/333.5; 549/77, 475; 514/237.8, 351, 514/357, 411, 367, 398, 425, 438, 471, 571, 514/345; 564/55
See application file for complete search history.

(56) References Cited

U.S. PATENT DOCUMENTS

| | | | |
|---|---|---|---|
| 1,792,156 A | 2/1931 | Fitzky | .......................... 564/52 |
| 2,046,375 A | 7/1936 | Goldstein et al. | .............. 564/52 |
| 2,093,265 A | 9/1937 | Coffby et al. | .............. 564/52 X |
| 2,288,422 A | 6/1942 | Rohm | ....................... 564/52 X |
| 2,649,476 A | 8/1953 | Martin | |
| 2,683,082 A | 7/1954 | Hill et al. | ................... 564/52 X |
| 2,722,544 A | 11/1955 | Martin | |
| 2,745,874 A | 5/1956 | Schetty et al. | ............. 564/52 X |
| 2,781,330 A | 2/1957 | Downey | .................... 564/52 X |
| 2,797,214 A | 6/1957 | Werner Bossard | |
| 2,867,659 A | 1/1959 | Model et al. | ............... 564/52 X |
| 2,877,268 A | 3/1959 | Applegath et al. | ......... 564/53 X |
| 2,960,488 A | 11/1960 | Tamblyn et al. | ............ 564/52 X |
| 2,973,386 A | 2/1961 | Weldon | ..................... 564/55 X |
| 3,151,023 A | 9/1964 | Martin et al. | |
| 3,200,035 A | 8/1965 | Martin et al. | |
| 3,230,141 A | 1/1966 | Frick et al. | |
| 3,284,433 A | 11/1966 | Minami et al. | |
| 3,424,760 A | 1/1969 | Helsley et al. | |
| 3,424,761 A | 1/1969 | Helsley et al. | |
| 3,424,762 A | 1/1969 | Helsley et al. | |
| 3,547,940 A | 12/1970 | Brantley | |
| 3,646,059 A | 2/1972 | Brantley | |
| 3,689,550 A * | 9/1972 | Schellenbaum et al. | ........ 564/55 |
| 3,743,498 A | 7/1973 | Brantley | |
| 3,754,887 A | 8/1973 | Brantley | |
| 3,823,161 A | 7/1974 | Lesser | |
| 3,828,001 A | 8/1974 | Broad et al. | |
| 3,860,645 A | 1/1975 | Nikawitz | ...................... 564/52 |
| 3,990,879 A | 11/1976 | Soper | |
| 4,001,256 A | 1/1977 | Callahan et al. | |
| 4,009,847 A | 3/1977 | Aldrich et al. | |
| 4,042,372 A | 8/1977 | Harper | |
| 4,062,861 A | 12/1977 | Yukinaga et al. | |
| 4,071,524 A | 1/1978 | Banitt | |
| 4,111,680 A | 9/1978 | Yukinaga et al. | |
| 4,111,683 A | 9/1978 | Singer | |
| 4,116,671 A | 9/1978 | Yukinaga et al. | |
| 4,173,637 A | 11/1979 | Nishiyama et al. | |
| 4,173,638 A | 11/1979 | Nishiyama et al. | |
| 4,183,854 A | 1/1980 | Crossley | |
| 4,212,981 A | 7/1980 | Yukinaga et al. | |
| 4,240,820 A | 12/1980 | Dickore et al. | |
| 4,279,639 A | 7/1981 | Okamoto et al. | |

(Continued)

FOREIGN PATENT DOCUMENTS

CA          2146707        10/1995

(Continued)

OTHER PUBLICATIONS

U.S. Appl. No. 10/788,029 (Bayer Corporation), to Scott, et al, filed Feb. 27, 2004.*

(Continued)

*Primary Examiner*—Rei-Tsang Shiao
*Assistant Examiner*—Janet L Coppins
(74) *Attorney, Agent, or Firm*—Millen, White, Zelano & Branigan, P.C.

(57) ABSTRACT

This invention relates to the use of a group of aryl ureas in treating cytokine mediated diseases and proteolytic enzyme mediated diseases, and pharmaceutical compositions for use in such therapy.

21 Claims, No Drawings

U.S. PATENT DOCUMENTS

| | | | |
|---|---|---|---|
| 4,405,644 A | 9/1983 | Kabbe et al. | |
| 4,410,697 A | 10/1983 | Török et al. | |
| 4,437,878 A | 3/1984 | Acker et al. | |
| 4,468,380 A | 8/1984 | O'Doherty et al. | |
| 4,473,579 A | 9/1984 | Devries et al. | |
| 4,511,571 A | 4/1985 | Böger et al. | |
| 4,514,571 A | 4/1985 | Nakai et al. | |
| 4,526,997 A | 7/1985 | O'Doherty et al. | |
| 4,546,191 A | 10/1985 | Nishiyama et al. | |
| 4,623,662 A | 11/1986 | De Vries | |
| 4,643,849 A | 2/1987 | Hirai et al. | |
| 4,740,520 A | 4/1988 | Hallenbach et al. | |
| 4,760,063 A | 7/1988 | Hallenbach et al. | |
| 4,808,588 A | 2/1989 | King | |
| 4,820,871 A | 4/1989 | Kissener et al. | |
| 4,863,924 A | 9/1989 | Haga et al. | |
| 4,973,675 A | 11/1990 | Israel et al. | |
| 4,983,605 A | 1/1991 | Kondo et al. | |
| 4,985,449 A | 1/1991 | Haga et al. | |
| 5,036,072 A | 7/1991 | Nakajima et al. | |
| 5,059,614 A | 10/1991 | Lepage et al. | |
| 5,098,907 A | 3/1992 | Kondo et al. | |
| 5,130,331 A | 7/1992 | Pascual | |
| 5,162,360 A | 11/1992 | Creswell et al. | |
| 5,185,358 A | 2/1993 | Creswell et al. | |
| 5,312,820 A | 5/1994 | Ashton et al. | |
| 5,319,099 A | 6/1994 | Kamata et al. | |
| 5,399,566 A | 3/1995 | Katano et al. | |
| 5,423,905 A | 6/1995 | Fringeli | 564/55 X |
| 5,429,918 A | 7/1995 | Seto et al. | |
| 5,432,468 A | 7/1995 | Moriyama et al. | |
| 5,447,957 A | 9/1995 | Adams et al. | |
| 5,470,882 A | 11/1995 | Dixon et al. | |
| 5,500,424 A | 3/1996 | Nagamine et al. | |
| 5,508,288 A | 4/1996 | Forbes et al. | |
| 5,559,137 A | 9/1996 | Adams et al. | |
| 5,596,001 A | 1/1997 | Hamanaka | |
| 5,597,719 A | 1/1997 | Freed et al. | |
| 5,807,891 A | 1/1997 | Freed et al. | |
| 5,696,138 A | 12/1997 | Olesen et al. | |
| 5,698,581 A | 12/1997 | Kleemann et al. | |
| 5,710,380 A | 1/1998 | Talley et al. | |
| 5,773,459 A | 6/1998 | Tang et al. | |
| 5,780,483 A | 7/1998 | Widdowson et al. | |
| 5,814,646 A | 9/1998 | Heinz et al. | |
| 5,886,044 A | 3/1999 | Widdowson et al. | |
| 5,891,895 A | 4/1999 | Shiraishi et al. | |
| 5,908,865 A | 6/1999 | Doi et al. | |
| 5,929,250 A | 7/1999 | Widdowson et al. | |
| 5,965,573 A | 10/1999 | Petrie et al. | |
| 6,004,965 A | 12/1999 | Breu et al. | |
| 6,005,008 A | 12/1999 | Widdowson et al. | |
| 6,015,908 A | 1/2000 | Widdowson et al. | |
| 6,020,345 A | 2/2000 | Vacher et al. | |
| 6,022,884 A | 2/2000 | Mantlo et al. | |
| 6,040,339 A | 3/2000 | Yoshida et al. | |
| 6,043,374 A | 3/2000 | Widdowson et al. | |
| 6,080,763 A | 6/2000 | Regan | |
| 6,093,742 A | 7/2000 | Salituro et al. | |
| 6,133,319 A | 10/2000 | Widdowson | |
| 6,143,764 A | 11/2000 | Kubo et al. | |
| 6,147,116 A | 11/2000 | Barbachyn et al. | |
| 6,150,415 A | 11/2000 | Hammock et al. | |
| 6,174,901 B1 | 1/2001 | Mantlo et al. | |
| 6,178,399 B1 | 1/2001 | Takebayashi et al. | |
| 6,180,675 B1 | 1/2001 | Widdowson et al. | |
| 6,187,799 B1 | 2/2001 | Wood et al. | |
| 6,211,373 B1 | 4/2001 | Widdowson et al. | |
| 6,218,539 B1 | 4/2001 | Widdowson | |
| 6,242,601 B1 | 6/2001 | Breu et al. | |
| 6,262,113 B1 | 7/2001 | Widdowson et al. | |
| 6,271,261 B1 | 8/2001 | Widdowson | |
| 6,310,068 B1 | 10/2001 | Böttcher et al. | |
| 6,333,341 B1 | 12/2001 | Mantlo et al. | |
| 6,339,045 B1 | 1/2002 | Kanno et al. | |
| 6,344,476 B1 * | 2/2002 | Ranges et al. | 514/447 |
| 6,380,218 B1 | 4/2002 | Marfat et al. | |
| 6,391,917 B1 | 5/2002 | Petrie et al. | |
| 6,414,011 B1 * | 7/2002 | Hogenkamp et al. | 514/406 |
| 6,500,863 B1 * | 12/2002 | Jin et al. | 514/593 |
| 6,525,046 B1 * | 2/2003 | Cirillo et al. | 514/227.8 |
| 6,525,091 B2 * | 2/2003 | Robinson et al. | 514/517 |
| 6,608,052 B2 * | 8/2003 | Breitfelder et al. | 514/227.8 |
| 6,617,324 B1 * | 9/2003 | Naraian et al. | 514/235.8 |
| 7,235,576 B1 * | 6/2007 | Riedl et al. | 514/388 |
| 2002/0062763 A1 | 5/2002 | Macholdt et al. | |
| 2002/0065296 A1 | 5/2002 | Dumas et al. | |
| 2002/0082255 A1 | 6/2002 | Eastwood | |
| 2002/0128321 A1 | 9/2002 | Widdowson et al. | |

FOREIGN PATENT DOCUMENTS

| | | |
|---|---|---|
| DE | 0487014 | 12/1929 |
| DE | 0511468 | 10/1930 |
| DE | 0523437 | 5/1931 |
| DE | 2436179 A1 | 2/1975 |
| DE | 25 01 648 | 7/1975 |
| DE | 3305866 A1 | 2/1983 |
| DE | 3529247 A1 | 11/1986 |
| DE | 3540377 A1 | 5/1987 |
| DE | 0253997 | 2/1988 |
| EP | 4931 | 10/1979 |
| EP | 0016371 A1 | 10/1980 |
| EP | 0107214 A1 | 5/1984 |
| EP | 0116932 A | 8/1984 |
| EP | 0192263 B1 | 8/1986 |
| EP | 0202538 A1 | 11/1986 |
| EP | 0230400 A2 | 7/1987 |
| EP | 0233559 B1 | 8/1987 |
| EP | 0242666 A1 | 10/1987 |
| EP | 0264904 A2 | 4/1988 |
| EP | 335156 | 3/1989 |
| EP | 371876 | 11/1989 |
| EP | 0359148 A1 | 3/1990 |
| EP | 0379915 A1 | 8/1990 |
| EP | 0380048 A2 | 8/1990 |
| EP | 0381987 A1 | 8/1990 |
| EP | 0405233 | 1/1991 |
| EP | 0405233 A1 | 1/1991 |
| EP | 425443 | 5/1991 |
| EP | 459887 | 5/1991 |
| EP | 0676395 A2 | 10/1995 |
| EP | 0690344 | 1/1996 |
| EP | 0709225 | 5/1996 |
| EP | 0860433 A1 | 8/1998 |
| FR | 1457172 | 9/1966 |
| GB | 828231 | 10/1956 |
| GB | 0771333 | 3/1957 |
| GB | 0921682 | 3/1963 |
| GB | 1590870 | 6/1981 |
| IR | 26555 | 1/2000 |
| JP | 44-2569 | 2/1969 |
| JP | 50-76072 | 6/1975 |
| JP | 550-77375 | 6/1975 |
| JP | 50-149668 | 11/1975 |
| JP | 51-063170 | 6/1976 |
| JP | 51-80862 | 7/1976 |
| JP | 53-086033 | 7/1978 |
| JP | 54-032468 | 9/1979 |
| JP | 55-98152 | 7/1980 |
| JP | 55-124763 | 9/1980 |
| JP | 55-162772 | 12/1980 |
| JP | 3 532 47 | 3/1991 |
| JP | 8 031841 | 11/1996 |

| | | |
|---|---|---|
| JP | 10-306078 | 11/1998 |
| LB | 6124 | 1/2000 |
| WO | 90/02112 | 3/1990 |
| WO | 93/18028 | 9/1993 |
| WO | 93/24458 | 12/1993 |
| WO | 94/14801 | 7/1994 |
| WO | 94/18170 | 8/1994 |
| WO | 94-22807 | 10/1994 |
| WO | 94/25012 | 11/1994 |
| WO | 95/02591 | 1/1995 |
| WO | 95/07922 | 3/1995 |
| WO | 95/13067 | 5/1995 |
| WO | 95/31451 | 11/1995 |
| WO | 99/00357 | 1/1996 |
| WO | WO 96/10559 | 4/1996 |
| WO | WO 96/13632 | 5/1996 |
| WO | 96/25157 A1 | 8/1996 |
| WO | 96/40673 | 12/1996 |
| WO | 96/40675 A1 | 12/1996 |
| WO | WO 97/09973 | 3/1997 |
| WO | WO 97/17329 | 5/1997 |
| WO | 97/29743 | 8/1997 |
| WO | WO 99/40673 | 8/1997 |
| WO | 97/40028 A1 | 10/1997 |
| WO | 97/45400 | 12/1997 |
| WO | 97/49399 | 12/1997 |
| WO | 97/49400 | 12/1997 |
| WO | WO 98/17267 | 4/1998 |
| WO | 98/22432 | 5/1998 |
| WO | WO 98/20868 | 5/1998 |
| WO | WO 98/22103 | 5/1998 |
| WO | WO 97/30992 | 8/1998 |
| WO | WO 98/45268 | 10/1998 |
| WO | WO 98/52558 | 11/1998 |
| WO | WO 98/52559 | 11/1998 |
| WO | WO 99/33458 | 11/1998 |
| WO | 99/00370 | 1/1999 |
| WO | WO 99/20617 | 4/1999 |
| WO | WO 99/32110 | 4/1999 |
| WO | WO 99/21835 | 5/1999 |
| WO | WO 99/23091 | 5/1999 |
| WO | WO 99/24398 | 5/1999 |
| WO | WO 99/24635 | 5/1999 |
| WO | WO 99/28305 | 6/1999 |
| WO | WO 99/32106 | 7/1999 |
| WO | WO 99/32111 | 7/1999 |
| WO | WO 99/32436 | 7/1999 |
| WO | WO 99/32437 | 7/1999 |
| WO | WO 99/32455 | 7/1999 |
| WO | WO 99/32463 | 7/1999 |
| WO | WO 00/17175 | 3/2000 |
| WO | WO 00/41698 | 7/2000 |
| WO | WO 00/42012 | 7/2000 |
| WO | WO 00/43366 | 7/2000 |
| WO | WO 00/43384 | 7/2000 |
| WO | WO 0047577 | 8/2000 |
| WO | WO 00/55139 | 9/2000 |
| WO | WO 00/55152 | 9/2000 |
| WO | WO 00/56331 | 9/2000 |
| WO | WO 01/36403 A1 | 5/2001 |
| WO | WO 02/14331 | 2/2002 |
| WO | WO 02/24635 A2 | 3/2002 |
| WO | WO 02/062763 A2 | 8/2002 |
| WO | WO 02/083628 A1 | 10/2002 |
| WO | WO 02/085857 A2 | 10/2002 |
| WO | WO 02/085859 A1 | 10/2002 |
| WO | WO 02/092576 | 11/2002 |
| WO | WO 03/099771 | 12/2003 |

OTHER PUBLICATIONS

U.S. Appl. No. 10/789,446 (Bayer Corporation), to Dumas et al, filed Mar. 1, 2004.*

Tarzia G. et al. Synthesis and antiinflammatory properties of some pyrrolo(1H,3H)[3,4] pyrimidin-2-ones and pyrrolo(1H,3H)[3,4-d]pyrimidin-2-ones and pyrrolo(1H,6H),[3,4]-d]pyrimidin-2-ones. Chemical Abstracts. Aug. 27, 1979, No. 74558p; p. 594.

Chemical Abstract, vol. 116, No. 21, May 25, 1992, pp. 741-742.

Wild, Hanno, "Substructure #1," Jul. 18, 1996, pp. 1-107.

Michaelis, Justus, Liebigs Ann. Chem. (JLACBF) 397, 1913, 143.

Abstract of EP 116,932.

Abstract of EP 676,395.

Abstract of EP 202,538.

Abstract of EP 16,371.

Avruch et al., "Raf meets Ras: completing the framework of a signal transduction pathway", TIBS 19; Jul. 1994; pp. 279-2823.

White, A. D., et al., "Heterocyclic Ureas: Inhibitors of Acyl-CoA:Cholesterol O-Acyltransferase as Hypochelesterolemic Agents," Jun. 6, 1996, pp. 4382-4395.

Audia, James E., et al., "Potent, Selective Tetraphdro-β-carboline Antagonists of the Serotonin 2B ($5HT_{2B}$) Contractile Receptor in the Rat Stomach Fundus," Jan. 22, 1996, pp. 2773-2780.

Forbes, Ian T., "N-(1-Methyl-5-indolyl)-N'-(3-methyl-5-isothiazolyl)urea: A Novel, High-Affinity $5-HT_{2B}$ Receptor Antagonist," Mar. 17, 1995, pp. 955-957.

Boulton, A. J., et al., "Heterocyclic Rearrangements. Part X.[1] A Generalised Monocyclic Rearrangement," 1967, 2005-07.

N. S. Magnuson, et al., "The Raf-1 serine/threonine protein kinase," Cancer Biology, vol. 5, 1994, pp. 247-253.

G. Daum, et al., The ins and outs of Raf Kinases,: TIBS Nov. 19, 1994, pp. 474-480.

W. Kolch, et al., "Raf-1 protein kinase is required for growth of induced NIH/3T3 cells," Letters to Nature, vol. 349, Jan. 31, 1991, pp. 226-228.

M. Fridman, et al., "The Minimal Fragments of c-Raf-1 and NF1 That Can Suppress v-Ha-Ras-Induced Malignant Phenotype," The Journal of Biological Chemistry, vol. 269, No. 48, Dec. 2, 1994, pp. 30105-30108.

G. L. Bolton, et al., Chapter 17. Ras Oncogene Directed Approaches in Cancer Chemotherapy, Annual Reports In Medicinal Chemistry, vol. 29, 1994, pp. 165-174.

J. L. Bos, "ras Oncogenes in Human Cancer: A Review," Cancer Research, vol. 49, Sep. 1, 1989, pp. 4682-4689.

B. P. Monia, et al., "Antitumor activity of a phosphorothioate antisense oligodeopxynucleotide targeted against C-raf kinase," Nature Medicine, vol. 2, No. 6, Jun. 1996, pp. 668-675.

Lee, et al., Bicyclic Imidazoles as a Novel Class of Cytokine Biosynthesis Inhiibitors, N.Y. Academy of Science, 1993, pp. 149-170.

F. Lepage, et al., "New N-aryl isoxazolecarboxamides and N-isoxazolybenzamides as anticonvulsant agents," Eur. J. Med. Chem, vol. 27, 1992, pp. 581-593.

Ridley, et al., "Actions of IL-1 are Selectively Controlled by p38 Mitogen-Activated Protein Kinase," The American Association of Immunologists, 1997, pp. 3165-3173.

Caplus 86:72448, Abstract JP 57053785, Pyridine derivatives, Maeda Ryozo et al., Nov. 15, 1982.

Caplus 84:180049, Abstract JP 56029871, Hamada Yoshinori et al., Jul. 10, 1981.

Caplus 84:43857, Abstract JP 58021626, Maeda Ryozo et al., May 2, 1983.

Murata et al., Chemical and Pharmaceutical Bulletin, vol. 22, 1974, p. 1212.

Garcia-Lopez et al., Journal of the American Chemical Society, vol. 1978, pp. 438-437.

Joseph T. Bruder and Imre Kovesdi, Adenovirus Infectin Stimulates the Raf/MAPK Signaling Pathway and Induces Interleukin-8 Expression, May 17, 1996, vol. 71, No. 1, pp. 398-404.

Hiroshi Kubo et al., Herbicidal Activity of 1,3,4-Thiadiazole Derivatives, 1970, pp. 60-65.

F. Russo, Sintesi Di Derivati 2,6-Sostituiti Del 5H-1,3,5-Tiadiazolo[3,2-a]-s-Triazina-5,7-Dione, 1978, pp. 972-983.

A. M. Grant et al., Some Hypotensive Thiadiazoles, 1972, pp. 1083-1084.

Odette Foussard-Blanpin, Etude pharmacodynamique comparee de carboxamides diversement substitutes dans le domaine du systeme nerveux central; 1982; pp. 339-350.

Ian T. Forbes et al., "Medicinal Chemistry", vol. 38, No. 6, Mar. 17, 1995, pp. 855-857.

Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.

Caplus 113:142130, Abstract of JP 2023337, Silver halide photographic material containing phenolic cyan coupler a colorless cyan coupler, Toshihiko Yagi et al., Jan. 25, 1990.

Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat", Chemical Life Science, pp. 157-166, 1977.

Caplus 127:293717, "Optical properties of segmented oligourethane with azomethine terminal fragments", National Academy of Science of Ukraine, M. V. Kurik et al., pp. 2038-2041, 1996.

Caplus 127:273945, "Quantitative structure-biodegradability studies: an investigation of the MITI aromatic compound database", School of Pharmacy and Chemistry, J. C. Dearden, pp. 93-104, 1996.

Caplus 126:166148, "Inhibitors of coenzyme A-independent transacylase induce apoptosis in human HL-60 cells", James D. Winkler et al., J. Pharmacol. Exp. Ther. pp. 956-966, 1996.

Caplus 98:78152, Abstract of JP 57185219, "Antitumor benzophenone derivatives", Nov. 15, 1982.

Caplus 72:79046, Abstract of CH 479557, "Tuberculostatic and cancerostatic polybasic ureas", Dr. A. Wander, Oct. 15, 1969.

Caplus 125:245169, "Production of murine monoclonal antibodies against sulcofuron and flucofuron by in vitro immunization", G. A. Bonwick et al., J. Immunol. Methods, pp. 163-173, 1996.

Caplus 127:34137f, "Preparation of quinoline an dquinazoline derivatives inhibiting platelet-derived growth factor receptor autophosphorylation", Kazuo Kubo et al., May 15, 1997.

Caplus 131:58658, "Inhibition of raf kinase using symmetrical and unsymmetrical substituted diphenyl ureas", Miller, Scott, Jul. 1, 1999.

Caplus 131:87909y, "Inhibition of p38 kinase activity using substituted heterocyclic ureas", Jacques Dumas, Jul. 1, 1999.

Caplus 131:73649b, "Preparation of pyrazolyl aryl ureas and related compounds as p38kinase inhibitor", Jacques Dumas, Jul. 1, 1999.

Joseph V. Simone, "Cecil Textbook of Medicine", 20th Edition, vol. 1, Feb. 3, 1997. pp. 1004-1010.

Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.

Jacqueline E. van Muijlwijk-Koezen et al., "Isoquinoline and Quinazoline Urea Analogues as Antagonists for the Human Adenosine $A_3$ Receptor", J. Ed. Chem. 2000, 43, pp. 2227-2238, Jan. 3, 2000.

Jacques Dumas et al., "1-Phenyl-5-pyrazolyl Ureas: Potent and Selective p38 Kinase Inhibitors", Bioorganic & Medicinal Chemistry Letters, pp. 2051-2054, May 2, 2000.

Robert W. Carling et al., "1-(3-Cyanobenxylpiperidin-4-yl)-5-methyl-4-phenyl-1,3-dihydroimidazol-2-one: A Selective High-Affinity Antagonist for the Human Dopamine $D_4$ Receptor with Excellent Selectivity over Ion Channels", J. Med. Chem., 1999, 42, pp. 2706-2715.

XP-002086152 "Pulmonary-Allergy, Dermatological, Gastrointestinal & Arthritis", Gunnar J. Hanson, 1997.

XP-002103155 "The structural Basis For The Specificity Of Pyridinylimidazole Inhibitors Of p38 MAP Kinase", Keith P. Wilson et al, 1997.

Blanco, "p38 MAPK signaling cascades: ancient roles and new functions," Bioassays, 22:637-645, 2000.

Dumas, J. "Protein Kinase Inhibitors from the urea class," Curr. Opin. In Drug Discovery and Dev., 5:718-727, 2002.

Hotte et al., "Bay 43-9006: Early clinical data in patients with advanced solid malignancies," Current Pharmaceutical Design, 8:2249-2253, 2002.

Kubo et al. "Synthesis and structure-activity relationship of quinazoline-urea derivatives as novel orally active VEGF receptor tyrosine kinase selective inhibitors," Proceedings of the American Association of Cancer Res. 43:182, 2002.

Madwed et al., "Pharmacological Evaluation of BIRB 796, a selective inhibitor of P38 MAP kinase (MAPK), in animal models of endotoxic shock, inflammation and arthritis," Inflammation Res., 50:S184, 2001.

Regan et al., "Pyrazole urea-based inhibitors of P38 MAP kinase: from lead compound to clinical candidate," J. Med. Chem. 45:2994-3008, 2002.

Proceedings of the American Association for Cancer Research—vol. 42—Mar. 2001—#4954 Anti-Tumor Efficacy of the Orally Actibe Raf Kinase Inhibitor BAY 43-9006 in Human Tumor Xenograft Models. Christopher A. Carter et al., Bayer Corporation.

XP-001145779 "Antitumor Activity of a C-raf Antisense Oligonucleotide in Combination with Standard Chemotherapeutic Agents against Various Human Tumors Transplanted Subcutaneously into Nude Mice", Thomas Geiger et al., vol. 3, 1179-1185, Jul. 1997.

XP-002232130, "A Phase I Trial of H-ras Antisense Oligonucleotide ISIS 2503 Administered as a Continuous Intravenous Infusion in Patients with Advanced Carcinoma", C. Casey Cunningham et al., 2001 American Cancer Society, vol. 92, No. 5, pp. 1265-1271.

Riedl et al., Potent Raf Kinase Inhibitors from the Diphenylurea Class: Structure Activity Relationships, Proc. Amer. Assoc. Can. Res., 42:923, 2001.

XP-001145481 +2921 Phase I and Pharmacokinetic Study of the Raf Kinase Inhibitor Bay 43-9006 in Patients with Locally Advanced or Metastic Cancer, Proceedings of the Annual Meeting of the American Association of Cancer Research, 42:543, 2001, Dirk Strumberg et al., Bayer AG.

Dumas, "CAS Substructure" pp. 1-29 1997.

Facts and Comparisons, 1994, 2703-2705.

XP-002233466, Medline/NLM, NLM8336809—[Intra-arterial ACNU, CDDP chemotherapy for brain metastases from lung cancer: comparison of cases with and without intra-arterial mannitol infusion], Iwadate Y et al.

Lowinger, T. B.; Riedl, B.; Wood, J.; Dumas, J.; Smith, R. A.; Khire, U.; Bankston, D.; Monahan, M.K.; Scott, W. J.; Lee, W.; Johnson, J. S.; Caringal, Y.; Turner, T.; Gane, T.; Kennure, N.; Barbosa, J. "Discovery of a Novel Class of Potent Raf Kinase inhibitors: Structure Activity Relationships" Clin. Cancer Res. 2000, 6(suppl.) 335.

Redman, A. M.; Johnson, J. S.; Dally, R.; Swartz. S.; Wild, H.; Paulsen, H.; Caringal, Y.; Gunn, D.; Renick, J.; Osterhout, M.; Kingery-Wood, J.; Smith, R. A.; Lee, W.; Dumas, J.; Wilhelm, S. M.; Housley, T. J.; Bhargava, A.; Ranges, G. E.; Shrikhande, A.; Young, D.; Bombara, M.; Scott W. J. "P38 Kinase Inhibitors for the Treatment of Arthritis and Osteoporosis: Thienyl, Furyl and Pyrrolyl Ureas" Bioorg. Med. Chem. Lett. 2001, 11 (1), 9.

Dumas, J.; Hatoum-Mokdad, H.; Sibley, R. N.; Smith, R. A.; Scott, W. J.; Khire, .U.; Lee, W.; Wood, J.; Wolanin, D.; Cooley, J.; Bankston, D.; Redman, A. M.; Schoenleber, R.; Caringal, Y.; Gunn, D.; Romero, R.; Osterhout, M.; Paulsen, H.; Housley, T. J.; Wilhelm, S. M.; Bhargava, A.; Pirro, J.; Chien, D.-S.; Ranges, G. E.; Shrikhande, A.; Muzsi, A.; Bortolon, E.; Wakefield, J.; Gianpaolo-Ostravage, C.; Chau, T. "Synthesis and Pharmacological Characterization of a Potent, Orally Active p38 Kinase Inhibitor" Bioorg. Med. Chem. Lett. 2002, 12, 1559.

Lowinger, T. B.; Riedl, B.; Dumas, J.; Smith, R. A. "Design and Discovery of Small Molecules Targeting Raf-1 Kinase" Curr. Pharm. Design 2002, 8 (25), 2269.

Dumas, J. "Protein Kinase Inhibitors from the Urea Class" Curr. Opin. Drug Discov. Dev. 2002, 5(5), 715-724.

Bankston, D.; Dumas, J.; Natero, R.; Riedl, B.; Monahan, M.-K.; Sibley, R. "A Scaleable Synthesis of BAY 43-9006: A Potent Raf Kinase Inhibitor for the Treatment of Cancer" Org. Proc. Res. Dev. 2002, 6(6), 777-781.

Khire, U.; Bankston, D.; Barbosa, J.; Brittelli, D.; Caringal, Y.; Carlson, R.; Dumas, J.; Gane, T.; Heald, S.; Hibner, B.; Johnson, J. S.; Katz, M. E.; Kennure, N.; Kingery-Wood, J.; Lee, W.; Liu, X.-G.; Lowinger, T. B.; Renick, J.; McAlexander, I.; Monahan, M.-K.; Natero, R.; Riedl, B.; Rong, H.; Sibley, R. N.; Smith, R. A.; Wolanin, D.: "Omega-Carboxypyridyl Substituted Ureas as Raf Kinase Inhibitors: SAR of the Amide Substituent" Bioorg. Med. Chem. Lett. 2004, 14, 783-786.

Dumas, J.; Smith, R. A.; Lowinger, T. B.: "Recent Developments in the Discovery of Protein Kinase Inhibitors from the Urea Class" Curr. Opin. Drug Discov. Dev. 2004, 7(5), 600-616.

Wan PTC, Garnett MJ, Roe SM, Lee S, Niculescu-Duvaz D, Good VM, Cancer genome project, Jones CM, Marshall CJ, Springer CJ, Barford D, Marais R: Mechanism of activation of the RAF-ERK signaling pathway by oncogenic mutations of B-RAF. Cell 2004, 116, 855-867.

Mross K, Steinbild S, Baas F, Reil M, Buss P, Mersmann S, Voliotis D, Schwartz B, Brendel E: "Drug-drug interaction pharmacokinetic study with the Raf kinase inhibitor (RKI) BAY 43-9006 administered in combination with irinotecan (CPT-11) in patients with solid tumors" Int. J. Clin. Pharm. Ther. 2003, 41(12), 618-619.

Siu LL, Awada A, Takimoto CH, Moore MJ, Piccart M, Fiander W, Lathia C, Petrensiuc O: "Phase I study of oral Raf-1 kinase inhibitor BAY 43-9006 in combination with gemcitabine in patients with advanced solid tumors" 39th ASCO meeting, Chicago, IL (2003) Abstract 828.

Richly H, Kupsch P, Passage K, Grugert M, Hilger RA, Kredke S, Voliotis D, Scheulen ME, Seeber S, Strumberg D: "A Phase I clinical and pharmacokinetic study of the Raf kinase inhibitor (RKI) BAY 43-9006 administered in combination with doxorubicin in patients with solid tumors" Int. J. Clin. Pharm. Ther. 2003, 41(12), 620-621.

Sorbera LA, Castaner J, Bozzo J, Leeson PA: "Oncolytic Raf kinase inhibitor" Drugs Future 2002, 27, 1141-1147.

Bollag G, Freeman S, Lyons JF, Post LE: "Raf pathway inhibitors in oncology" Curr. Opin. Invest. Drugs 2003, 4(12), 1436-1441.

Lee JT, McCubrey JA: BAY-43-9006 (Bayer/Onyx). Curr Opin Invest Drugs (2003) 4(6):757-763.

Hotte SJ, Hirte HW: "BAY 43-9006: early clinical data in patients with advanced solid malignancies" Curr. Pharm. Design 2002, 8(25), 2249-2253.

DeGrendele H: "Activity of the Raf kinase inhibitor BAY 43-9006 in patients with advanced solid tumors" Clin. Colorectal Cancer 2003, 3(1), 16-18.

Wilhelm, S. M.; Carter, C.; Tang, L.Y.; Wilkie, D.; McNabola, A.; Rong, H.; Chen, C.; Zhang, X.; Vincent, P.; McHugh, M.; Cao, Y.; Shujath, J.; Gawlak, S.; Eveleigh, D.; Rowley, B.; Liu, L.; Adnane, L.; Lynch, M.; Auclair, D.; Taylor, I.; Gedrich, R.; Voznesensky, A.; Riedl, B.; Post, L. E.; Bollag, G.; Trail, P.A. "BAY 43-9006 exhibits broad spectrum oral antitumor activity and targets the RAF/MEK/ERK pathway and receptor tyrosine kinases involved in tumor progression and angiogenesis" Cancer Res. 2004, 64(19), 7099-7109.

Dumas, J.; Sibley, R.; Riedl, B.; Monahan, M.-K.; Lee, W.; Lowinger, T. B.; Redman, A. M.; Johnson, J. S.; Kingery-Wood, J.; Scott, W. J.; Smith, R. A.; Bobko, M.; Schoenleber, R.; Ranges, G. E.; Housley, T. J.; Bhargava, A.; Wilhelm, S. M.; Shrikhande, A. "Discovery of a New Class of p38 Kinase Inhibitors" Bioorg. Med. Chem. Lett. 2000, 10 (18), 2047.

Proceedings of the American Association for Cancer Research—vol. 42—Mar. 2001—#4957 A Novel Diphenylurea Raf-1 Kinase Inhibitor (RKI) Blocks the Raf/Mek/Erk Pathway in Tumor Cells. Scott McClelland Wilhelm et al., Bayer Corporation.

* cited by examiner

INHIBITION OF P38 KINASE USING SYMMETRICAL AND UNSYMMETRICAL DIPHENYL UREAS

This application is a continuation of 09/458,015, filed Dec. 10, 1999 (now abandoned); which is a continuation of 09/285,522, filed Dec. 22, 1998 (now abandoned), which claims benefit of Provisional Application 60/126,439, filed Dec. 22, 1997 (now abandoned).

FIELD OF THE INVENTION

This invention relates to the use of a group of aryl ureas in treating cytokine mediated diseases and proteolytic enzyme mediated diseases, and pharmaceutical compositions for use in such therapy.

BACKGROUND OF THE INVENTION

Two classes of effector molecules which are critical for the progression of rheumatoid arthritis are pro-inflammatory cytokines and tissue degrading proteases. Recently, a family of kinases was described which is instrumental in controlling the transcription and translation of the structural genes coding for these effector molecules.

The mitogen-activated protein (MAP) kinase family is made up of a series of structurally related proline-directed serine/threonine kinases which are activated either by growth factors (such as EGF) and phorbol esters (ERK), or by IL-1, TNFα or stress (p38, JNK). The MAP kinases are responsible for the activation of a wide variety of transcription factors and proteins involved in transcriptional control of cytokine production. A pair of novel protein kinases involved in the regulation of cytokine synthesis was recently described by a group from SmithKline Beecham (Lee et al. *Nature* 1994, 372, 739). These enzymes were isolated based on their affinity to bond to a class of compounds, named CSAIDs (cytokine suppressive anti-inflammatory drugs) by SKB. The CSAIDs, bicyclic pyridinyl imidazoles, have been shown to have cytokine inhibitory activity both in vitro and in vivo. The isolated enzymes, CSBP-1 and -2 (CSAID binding protein 1 and 2) have been cloned and expressed. A murine homologue for CSBP-2, p38, has also been reported (Han et al. *Science* 1994, 265, 808).

Early studies suggested that CSAIDs function by interfering with m-RNA translational events during cytokine biosynthesis. Inhibition of p38 has been shown to inhibit both cytokine production (eg., TNFα, IL-1, IL-6, IL-8) and proteolytic enzyme production (eg., MMP-1, MMP-3) in vitro and/or in vivo.

Clinical studies have linked TNFα production and/or signaling to a number of diseases including rheumatoid arthritis (Maini. *J. Royal Coll. Physicians London* 1996, 30, 344). In addition, excessive levels of TNFα have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoperosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including Plasmodium falciparum malaria (Perlmann et al. *Infect. Immunit.* 1997, 65, 116) and cerebral malaria (Rudin et al. *Am. J. Pathol.* 1997, 150, 257), non-insulin-dependent diabetes mellitus (NIDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M.S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). TNFα levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNFα has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), Helicobacter pylori infection during peptic ulcer disease (Beales et al. *Gastroenterology* 1997, 112, 136), Chaga's disease resulting from Trypanosoma cruzi infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), *meningococcal* infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491a), Sendai virus (Goldfield et al. *Proc. Nat'l. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

Because inhibition of p38 leads to inhibition of TNFα production, p38 inhibitors will be useful in treatment of the above listed diseases.

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1998, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al. *J. Invest. Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of MMP production, p38 inhibitors will be useful in treatment of the above listed diseases.

Inhibitors of p38 are active in animal models of TNFα production, including a muirne lipopolysaccharide (LPS) model of TNFα production. Inhibitors of p38 are active in a number of standard animal models of inflammatory diseases, including carrageenan-induced edema in the rat paw, arachadonic acid-induced edema in the rat paw, arachadonic acid-induced peritonitis in the mouse, fetal rat long bone resorption, murine type II collagen-induced arthritis, and Fruend's adjuvant-induced arthritis in the rat. Thus, inhibitors of p38 will be useful in treating diseases mediated by one or more of the above-mentioned cytokines and/or proteolytic enzymes.

The need for new therapies is especially important in the case of arthritic diseases. The primary disabling effect of osteoarthritis, rheumatoid arthritis and septic arthritis is the progressive loss of articular cartilage and thereby normal joint function. No marketed pharmaceutical agent is able to prevent or slow this cartilage loss, although nonsteroidal anti-inflammatory drugs (NSAIDs) have been given to control pain and swelling. The end result of these diseases is total loss of joint function which is only treatable by joint replacement surgery. P38 inhibitors will halt or reverse the progression of cartilage loss and obviate or delay surgical intervention.

Several patents have appeared claiming polyarylimidazoles and/or compounds containing polyarylimidazoles as inhibitors of p38 (for example, Lee et al. WO 95/07922; Adams et al. WO 95/02591; Adams et al. WO 95/13067; Adams et al. WO 95/31451). It has been reported that arylimidazoles complex to the ferric form of cytochrome $P450_{cam}$ (Harris et al. *Mol. Eng.* 1995, 5, 143, and references therein), causing concern that these compounds may display structure-related toxicity (Howard-Martin et al. *Toxicol. Pathol.* 1987, 15, 369). Therefore, there remains a need for improved p38 inhibitors.

SUMMARY OF THE INVENTION

This invention provides compounds, generally described as aryl ureas, including both aryl and heteroaryl analogues, which inhibit p38 mediated events and thus inhibit the production of cytokines (such as TNFα, IL-1 and IL-8) and proteolytic enzymes (such as MMP-1 and MMP-3). The invention also provides a method of treating a cytokine mediated disease state in humans or mammals, wherein the cytokine is one whose production is affected by p38. Examples of such cytokines include, but are not limited to TNFα, IL-1 and IL-8. The invention also provides a method of treating a protease mediated disease state in humans or mammals, wherein the protease is one whose production is affected by p38. Examples of such proteases include, but are not limited to collagenase (MMP-1) and stromelysin (MMP-3).

Accordingly, these compounds are useful therapeutic agents for such acute and chronic inflammatory and/or immunomodulatory diseases as rheumatoid arthritis, osteoarthritis, septic arthritis, rheumatic fever, bone resorption, postmenopausal osteoperosis, sepsis, gram negative sepsis, septic shock, endotoxic shock, toxic shock syndrome, systemic inflammatory response syndrome, inflammatory bowel diseases including Crohn's disease and ulcerative colitis, Jarisch-Herxheimer reactions, asthma, adult respiratory distress syndrome, acute pulmonary fibrotic diseases, pulmonary sarcoidosis, allergic respiratory diseases, silicosis, coal worker's pneumoconiosis, alveolar injury, hepatic failure, liver disease during acute inflammation, severe alcoholic hepatitis, malaria including Plasmodium falciparum malaria and cerebral malaria, non-insulin-dependent diabetes mellitus (NIDDM), congestive heart failure, damage following heart disease, atherosclerosis, Alzheimer's disease, acute encephalitis, brain injury, multiple sclerosis including demyelation and oligiodendrocyte loss in multiple sclerosis, advanced cancer, lymphoid malignancies, tumor metastasis, pancreatitis, including systemic complications in acute pancreatitis, impaired wound healing in infection, inflammation and cancer, periodontal diseases, corneal ulceration, proteinuria, myelodysplastic syndromes, systemic lupus erythematosus, biliary cirrhosis, bowel necrosis, psoriasis, radiation injury, toxicity following administration of monoclonal antibodies such as OKT3, host-versus-graft reactions including ischemia reperfusion injury and allograft rejections including kidney, liver, heart, and skin allograft rejections, lung allograft rejection including chronic lung allograft rejection (obliterative bronchitis) as well as complications due to total hip replacement, and infectious diseases including tuberculosis, *Helicobacter pylori* infection during peptic ulcer disease, Chaga's disease resulting from Trypanosoma cruzi infection, effects of Shiga-like toxin resulting from *E. coli* infection, effects of enterotoxin A resulting from *Staphylococcus* infection, *meningococcal* infection, and infections from *Borrelia burgdorferi, Treponema pallidum,* cytomegalovirus, influenza virus, Theiler's encephalomyelitis virus, and the human immunodeficiency virus (HIV).

The present invention, therefore, provides compounds generally described as aryl ureas, including both aryl and heteroaryl analogues, which inhibit the p38 pathway. The invention also provides a method for treatment of p38-mediated disease states in humans or mammals, e.g., disease states mediated by one or more cytokines or proteolytic enzymes produced and/or activated by a p38 mediated process. Thus, the invention is directed to compounds and methods for the treatment of diseases mediated by p38 kinase comprising administering a compound of Formula I

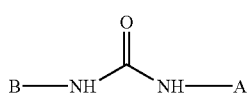

I wherein

A is

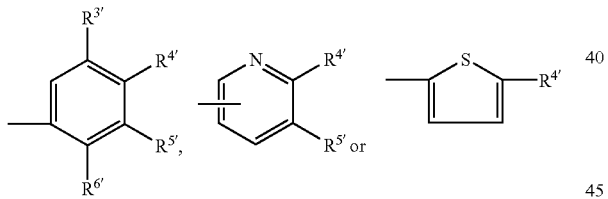

B is a substituted or unsubstituted, up to tricyclic aryl or heteroaryl moiety of up to 30 carbon atoms with at least one 6-member aromatic structure containing 0-4 members of the group consisting of nitrogen, oxygen and sulfur, wherein if B is substituted, it is substituted by one or more substituents selected from the group consisting of halogen, up to per-halo, and $W_n$, wherein n is 0-3 and each W is independently selected from the group consisting of —CN, —$CO_2R^7$, —C(O)$NR^7R^7$, —C(O)—$R^7$, —$NO_2$, —$OR^7$, —$SR^7$, —$NR^7R^7$, —$NR^7C(O)OR^7$, —$NR^7C(O)R^7$, $C_1$-$C_{10}$ alkyl, $C_{2-10}$-alkenyl, $C_{1-10}$-alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_{2-10}$-alkenyl, substituted $C_{1-10}$-alkoxy, substituted $C_3$-$C_{10}$ cycloalkyl, substituted $C_4$-$C_{23}$ alkheteroaryl and Q-Ar;

wherein if W is a substituted group, it is substituted by one or more substituents independently selected from the group consisting of —CN, —$CO_2R^7$, —C(O)$R^7$, —C(O)$NR^7R^7$, —$OR^7$, —$SR^7$, —$NR^7R^7$, $NO_2$, —$NR^7C(O)R^7$, —$NR^7C(O)OR^7$ and halogen up to per-halo;

wherein each $R^7$ is independently selected from H, $C_1$-$C_{10}$ alkyl, $C_{2-10}$-alkenyl, $C_3$-$C_{10}$ cycloalkyl, $C_6$-$C_{14}$ aryl, $C_3$-$C_{13}$ hetaryl, $C_7$-$C_{24}$ alkaryl, $C_4$-$C_{23}$ alkheteroaryl, up to per-halosubstituted $C_1$-$C_{10}$ alkyl, up to per-halosubstituted $C_{2-10}$-alkenyl, up to per-halosubstituted $C_3$-$C_{10}$ cycloalkyl, up to per-halosubstituted $C_6$-$C_{14}$ aryl and up to per-halosubstituted $C_3$-$C_{13}$ hetaryl, wherein Q is —O—, —S—, —N($R^7$)—, —$(CH_2)_m$—, —C(O)—, —CH(OH)—, —$(CH_2)_mO$—, —$NR^7C(O)NR^7R^7$—, —$NR^7C(O)$—, —C(O)$NR^7$—, —$(CH_2)_mS$—, —$(CH_2)_mN(R^7)$—, —O$(CH_2)_m$—, —CH$X^a$—, —C$X^a_2$—, —S—$(CH_2)_m$— and —N($R^7$)$(CH_2)_m$—, m=1-3, and $X^a$ is halogen; and Ar is a 5-10 member aromatic structure containing 0-2 members of the group consisting of nitrogen, oxygen and sulfur, which is unsubstituted or substituted by halogen up to per-halo and optionally substituted by $Z_{n1}$, wherein $_{n1}$ is 0 to 3 and each Z is independently selected from the group consisting of of —CN, —$CO_2R^7$, —C(O)$NR^7R^7$, —C(O)—$NR^7$, —C(O)$R^7$, —$NO_2$, —$OR^7$, —$SR^7$, —$NR^7R^7$, —$NR^7C(O)OR^7$, —$NR^7C(O)R^7$, $C_1$-$C_{10}$ alkyl, $C_3$-$C_{10}$ cycloalkyl, $C_6$-$C_{14}$ aryl, $C_3$-$C_{13}$ hetaryl, $C_7$-$C_{24}$ alkaryl, $C_4$-$C_{23}$ alkheteroaryl, substituted $C_1$-$C_{10}$ alkyl, substituted $C_3$-$C_{10}$ cycloalkyl, substituted $C_7$-$C_{24}$ alkaryl and substituted $C_4$-$C_{23}$ alkheteroaryl; wherein the one or more substituents of Z is selected from the group consisting of —CN, —$CO_2R^7$, —C(O)$NR^7R^7$, —$OR^7$, —$SR^7$, —$NO_2$, —$NR^7R^7$, —$NR^7C(O)R^7$, —$NR^7C(O)OR^7$, $R^{3'}$, $R^{4'}$, $R^{5'}$ are each independently H, $C_1$-$C_{10}$-alkyl, optionally substituted by halogen, up to perhalo, $C_{1-10}$ alkoxy, optionally substituted by halogen, up to perhaloalkoxy, halogen; $NO_2$ or $NH_2$;

$R^{6'}$ is H, $C_{1-10}$-alkyl, $C_{1-10}$ alkoxy, —NHCO$R^1$; —$NR^1COR^1$; $NO_2$;

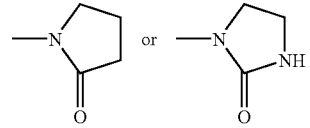

one of $R^{4'}$, $R^{5'}$ or $R^{6'}$ can be -X-Y, or 2 adjacent $R^{4'}$-$R^{6'}$ can together be an aryl or hetaryl ring with 5-12 atoms, optionally substituted by $C_{1-10}$-alkyl, $C_{1-10}$ alkoxy, $C_{3-10}$ cycloalkyl, $C_{2-10}$ alkenyl, $C_{1-10}$ alkanoyl, $C_{6-12}$ aryl, $C_{5-12}$ hetaryl or $C_{6-12}$ aralkyl;

$R^1$ is $C_{1-10}$-alkyl optionally substituted by halogen, up to perhalo;

X is —$CH_2$—, —S—, —N(CH$_3$)—, —NHC(O)—, —$CH_2$—S—, —S—$CH_2$—, —C(O)—, or —O—; and X is additionally a single bond where Y is pyridyl;

Y is phenyl, pyridyl, naphthyl, pyridone, pyrazine, benzodioxane, benzopyridine, pyrimidine or benzothiazole, each optionally substituted by $C_{1-10}$-alkyl, $C_{1-10}$-alkoxy, halogen, OH, —SCH$_3$ or $NO_2$ or, where Y is phenyl, by

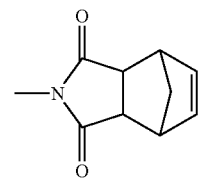

or a pharmaceutically acceptable salt thereof.

Preferably, the compounds of formula I are of formula Ia

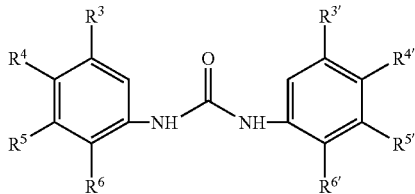

wherein $R^3$, $R^4$, $R^5$ and $R^6$ are each independently H, halogen, $C_{1-10}$-alkyl optionally substituted by halogen, up to perhalo, $C_{1-10}$-alkoxy, optionally substituted by at least one hydroxy group or by halogen, up to perhalo; $C_{6-12}$ aryl, optionally substituted by $C_{1-10}$ alkoxy or halogen, $C_{5-12}$ hetaryl, optionally substituted by $C_{1-10}$ alkyl, $C_{1-10}$ alkoxy or halogen; $NO_2$, $SO_2F$ or —$SO_2CH_pX_{3-p}$; —$COOR^1$; —$OR^1CONHR^1$; —$NHCOR^1$; —$SR^1$; phenyl optionally substituted by halo or $C_{1-10}$-alkoxy; $NH_2$; —$N(SO_2R^1)_2$, furyloxy,

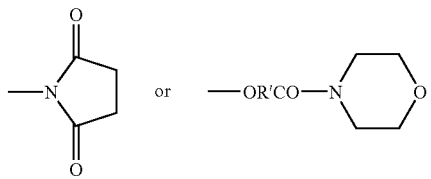

2 adjacent $R^3$-$R^6$ can together form an aryl or hetaryl ring with 5-12 atoms, optionally substituted by $C_{1-10}$-alkyl, $C_{1-1}$-alkoxy, $C_{3-10}$-cycloalkyl, $C_{2-10}$-alkenyl, $C_{1-10}$-alkanoyl, $C_{6-12}$-aryl, $C_{5-12}$-hetaryl, $C_{6-12}$-aralkyl, $C_{6-12}$-alkaryl, halogen; —$NR^1$, —$NO_2$; —$CF_3$; —$COOR^1$; —$NHCOR^1$; —$CN$; —$CONR^1R^1$; —$SO_2R^2$; —$SOR^2$; —$SR^2$; in which $R^1$ is H or $C_{1-10}$-alkyl and $R^2$ is $C_{1-10}$-alkyl; optionally substituted by halogen, up to perhalo, with —$SO_2$— optionally incorporated in the aryl or hetaryl ring;

one of $R^4$, $R^5$ or $R^6$ can be —X—Y, $R^1$ is $C_{1-10}$-alkyl, optionally substituted by halogen, up to perhalo;

p is 0 or 1;

X is —$CH_2$—, —S—, $N(CH_3)$—, —NHC(O), $CH_2$—S—, —S—$CH_2$—, —C(O)—, or —O—; and Y is phenyl, pyridyl, naphthyl, pyridone, pyrazine, benzodixane, benzopyridine, pyrimidine or benzothiazole, each optionally substituted by $C_{1-10}$-alkyl, $C_{1-10}$-alkoxy, halogen or $NO_2$ or, where Y is phenyl, by

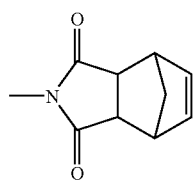

with the proviso that if $R^3$ and $R^6$ are both H, one of $R^4$ or $R^5$ is not H.

In formula I, suitable hetaryl groups B include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms, Each ring typically has 3-7 atoms. For example, B can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5- 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methyl-phenyl, 5-methyl-2-thienyl, 4-methyl-2-thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

Suitable aryl groups include, for example, phenyl and 1- and 2-naphthyl.

The term "cycloalkyl", as used herein, refers to cyclic structures with or without alkyl substituents such that, for example, "$C_4$ cycloakyl" includes methyl substituted cyclopropyl groups as well as cyclobutyl groups. The term "cycloalkyl" also includes saturated heterocyclic groups.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety.

Preferred compounds of formula I include those where $R^3$ is H, halogen or $C_{1-10}$-alkyl, optionally substituted by halogen, up to perhalo, $NO_2$, —$SO_2F$, —$SO_2CHF_2$; or —$SO_2CF_3$; $R^4$ is H, $C_{1-10}$-alkyl, $C_{1-10}$-alkoxy, halogen or $NO_2$; $R^5$ is H, $C_{1-10}$-alkyl optionally substituted by halogen, up to perhalo; $R^6$ is H, hydroxy, $C_{1-10}$-alkoxy, optionally substituted by at least one hydroxy group; —$COOR^1$; —$OR^1CONHR^1$; —$NHCOR^1$; —$SR^1$; phenyl optionally substituted by halo or $C_{1-10}$-alkoxy; $NH_2$; —$N(SO_2R^1)_2$, furyloxy, Preferably, $R^3$ is Cl, F, $C_{4-5}$-branched alkyl, —$SO_2F$ or —$SO_2CF_3$; and $R^6$ is hydroxy; $C_{1-10}$-alkoxy optionally substituted by at leaset one hydroxy group; —$COOR^1$; —$OR^1CONHR^1$; —$NHCOR^1$; —$SR^1$; phenyl optionally substituted by halo or $C_{1-10}$- alkoxy; $NH_2$; —$N(SO_2R^1)_2$, furyloxy, More preferably, $R^6$ is t-butyl or $CF_3$ and $R^6$ is —$OCH_3$. Preferably, $R^{4'}$ is $C_{1-10}$-alkyl or halogen; $R^{5'}$ is H, $C_{1-10}$-alkyl, halogen, $CF_3$, halogen, $NO_2$ or $NH_2$; and $R^{6'}$ is H, $C_{1-10}$-alkyl, halogen, —$NHCOCH_3$, —$N(CH_3)COCH_3$, $NO_2$,

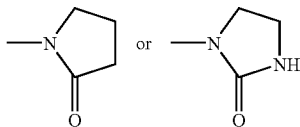

The invention also relates to compounds per se, of formula II

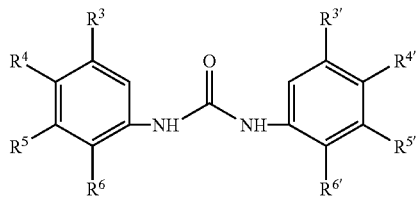

wherein

R³, R⁴, R⁵ and R⁶ are each independently H, halogen, $C_{1-10}$-alkyl optionally substituted by halogen up to perhalo, $C_{1-10}$-alkoxy, optionally substituted by at least one hydroxy group or halogen, up to perhalo; $NO_2$, $SO_2F$ or $-SO_2CH_nX_{3-n}$, $C_{1-10}$-alkoxy; $-COOR^1$; $-OR^1CONHR^1$; $-NH-COR^1$; $-SR^1$; $C_{6-12}$ aryl, optionally substituted by $C_{1-10}$-alkyl, $C_{1-10}$ alkoxy or halogen, $C_{5-12}$ hetaryl, optionally substitued by $C_{1-10}$ alkyl, $C_{1-10}$ alkoxy or halogen; $NH_2$; $-N(SO_2R^1)_2$; furyloxy;

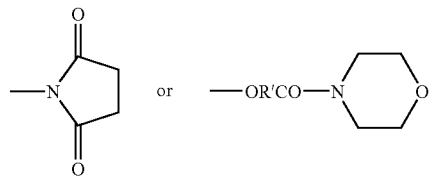

2 adjacent R³-R⁶ can together form an aryl or hetaryl ring with 5-12 atoms, optionally substituted by $C_{1-10}$-alkyl, $C_{1-10}$-alkoxy, $C_{3-10}$-cycloalkyl, $C_{2-10}$-alkenyl, $C_{1-10}$-alkanoyl, $C_{6-12}$-aryl, $C_{5-12}$-hetaryl, $C_{6-12}$-aralkyl, $C_{6-12}$-alkaryl, halogen; $-NR^1$; $-NO_2$; $-CF_3$; $-COOR^1$; $-NHCOR^1$; $-CN$; $-CONR^1R^1$; $-SO_2R^2$; $-SOR^2$; $-SR^2$; in which $R^1$ is H or $C_{1-10}$-alkyl and $R^2$ is $C_{1-10}$-alkyl;

R³', R⁴' and R⁵' are each independently H, $C_{1-10}$-alkyl, optionally substituted by halogen, up to perhalo; $NO_2$ or $NH_2$;

R⁶' is H, $C_{1-10}$-alkyl, halogen, $-NHCOR^1$; $-NR^1COR^1$; $NO_2$;

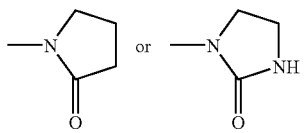

2 adjacent R⁴'-R⁶' can together be an aryl or hetaryl ring with 5-12 atoms;

$R^1$ is $C_{1-10}$-alkyl, optionally substituted by halogen, up to perhalo;

n is 0 or 1;

with the provisos that
(a) if R³ and R⁶ are both H, one of R⁴ or R⁵ is not H, and
(b) that R⁶ is phenyl substituted by alkoxy or halogen, alkoxy substituted by hydroxy, $-SO_2CF_2H$, $-OR^1CONHR^1$,

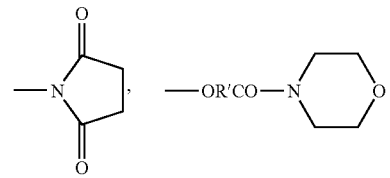

furyloxy or $-N(SO_2R^1)_2$;

or R⁶' is

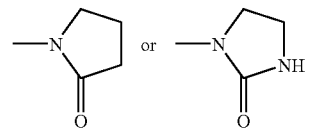

and (c) if R⁶ is phenyl substituted by alkoxy or halogen, the compounds have a pKa greater than 10, e.g., greater than 12, preferably greater than 15.

Preferred 5-tert-butylphenyl ureas are:
N-(5-tert-Butyl-2-methoxyphenyl)-N'-(4-phenyloxphenyl) urea;
N-(5-tert-Butyl-2-methoxyphenyl)-N'-(4-(4-methoxyphenyloxy)phenyl)urea;
N-(5-tert-Butyl-2-methoxyphenyl)-N'-(4-(4-pyridinyloxy) phenyl)urea;
N-(5-tert-Butyl-2-methoxyphenyl)-N'-(4-(4-pyridinylmethyl)phenyl)urea;
N-(5-tert-Butyl-2-methoxyphenyl)-N'-(4-(4-pyridinylthio) phenyl)urea;
N-(5-tert-Butyl-2-methoxyphenyl)-N'-(4-(4-(4,7-methano-1H-isoindole-1,3(2H)-dionyl)methyl)phenyl)urea;
N-(5-tert-Butyl-2-phenylphenyl)-N'-(2,3-dichlorophenyl) urea;
N-(5-tert-Butyl-2-(3-thienyl)phenyl)-N'-(2,3-dichlorophenyl)urea;
N-(5-tert-Butyl-2-(N-methylaminocarbonyl)methoxyphenyl)-N'-(2,3-dichlorophenyl)urea;
N-(5-tert-Butyl-2-(N-methylaminocarbonyl)methoxyphenyl)-N'-(1-naphthyl)urea;
N-(5-tert-Butyl-2-(N-morpholinocarbonyl)methoxyphenyl)-N'-(2,3-dichlorophenyl)urea;
N-(5-tert-Butyl-2-(N-morpholinocarbonyl)methoxyphenyl)-N'-(1-naphthyl)urea;
N-(5-tert-Butyl-2-(3-tetrahydrofuranyloxy)phenyl)-N'-(2,3-dichlorophenyl)urea; and
N-(5-tert-Butyl-2-methoxyphenyl)-N'-(4-(3-pyridinyl)methylphenyl)urea.

Preferred 5-trifuoromethylphenyl ureas are:
N-(5-Trifluoromethyl-2-methoxyphenyl)-N'-(4-methylphenyl)urea;
N-(5-Trifluoromethyl-2-methoxyphenyl)-N'-(4-methyl-2-fluorophenyl)urea;
N-(5-Trifluoromethyl-2-methoxyphenyl)-N'-(4-fluoro-3-chlorophenyl)urea;

N-(5-Trifluoromethyl-2-methoxyphenyl)-N'-(4-methyl-3-chlorophenyl)urea;
N-(5-Trifluoromethyl-2-methoxyphenyl)-N'-(4-methyl-3-fluorophenyl)urea;
N-(5-Trifluoromethyl-2-methoxyphenyl)-N'-(2,4-difluorophenyl)urea;
N-(5-Trifluoromethyl-2-methoxyphenyl)-N'-(4-phenyloxy-3,5-dichlorophenyl)urea;
N-(5-Trifluoromethyl-2-methoxyphenyl)-N'-(4-(4-pyridinylmethyl)phenyl)urea;
N-(5-Trifluoromethyl-2-methoxyphenyl)-N'-(4-(4-pyridinylthio)phenyl)urea;
N-(5-Trifluoromethyl-2-methoxyphenyl)-N'-(4-(4-pyridinyloxy)phenyl)urea;
N-(5-Trifluoromethyl-2-methoxyphenyl)-N'-(3-(4-pyridinylthio)phenyl)urea; and
N-(5-Trifluoromethyl-2-methoxyphenyl)-N'-(4-(3-(N-methylaminocarbonyl)phenyloxy)phenyl)-urea.

Preferred 5-sulfonylphenyl ureas are:
N-(5-Fluorosulfonyl)-2-methoxyphenyl)-N'-(4-methylphenyl)urea;
N-(5-(Difluromethanesulfonyl)-2-methoxyphenyl)-N'-(4-methylphenyl)ureaN-(5-(Difluromethanesulfonyl)-2-methoxyphenyl)-N'-(4-fluorophenyl)urea;
N-(5-(Difluromethanesulfonyl)-2-methoxyphenyl)-N'-(4-methyl-2-fluorophenyl)urea;
N-(5-(Difluromethanesulfonyl)-2-methoxyphenyl)-N'-(4-methyl-3-fluorophenyl)urea;
N-(5-(Difluromethanesulfonyl)-2-methoxyphenyl)-N'-(4-methyl-3-chlorophenyl)urea;
N-(5-(Difluromethanesulfonyl)-2-methoxyphenyl)-N'-(4-fluoro-3-chlorophenyl)urea;
N-(5-(Difluromethanesulfonyl)-2-methoxyphenyl)-N'-(4-fluoro-3-methylphenyl)urea;
N-(5-(Difluromethanesulfonyl)-2-methoxyphenyl)-N'-(2,3-dimethylphenyl)urea; and
N-(5-(Trifluoromethanesulfonyl)-2-methoxyphenyl)-N'-(4-methylphenyl)urea.

Preferred 2-naphthyl ureas are:
N-(3-Methoxy-2-naphthyl)-N'-(2-fluorophenyl)urea;
N-(3-Methoxy-2-naphthyl)-N'-(4-methylphenyl)urea;
N-(3-Methoxy-2-naphthyl)-N'-(3-fluorophenyl)urea;
N-(3-Methoxy-2-naphthyl)-N'-(4-methyl-3-fluorophenyl)urea;
N-(3-Methoxy-2-naphthyl)-N'-(2,3-dimethylphenyl)urea;
N-(3-Methoxy-2-naphthyl)-N'-(1-naphthyl)urea;
N-(3-Methoxy-2-naphthyl)-N'-(4-(4-pyridinylmethyl)phenyl)urea;
N-(3-Methoxy-2-naphthyl)-N'-(4-(4-pyridinylthio)phenyl)urea;
N-(3-Methoxy-2-naphthyl)-N'-(4-(4-methoxyphenyloxy)phenyl)urea; and
N-(3-Methoxy-2-naphthyl)-N'-(4-(4-(4,7-methano-1H-isoindole-1,3(2H)-dionyl)methyl)phenyl)urea.

Other preferred ureas are:
N-(2-Hydroxy-4-nitro-5-chlorophenyl)-N'-(phenyl)urea; and
N-(2-Hydroxy-4-nitro-5-chlorophenyl)-N'-(4-(4-pyridinylmethyl)phenyl)urea.

The present invention is also directed to pharmaceutically acceptable salts of formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, sulphonic acid, acetic acid, trifluoroacetic acid, malic acid, tartartic acid, citric acid, lactic acid, oxalic acid, succinic acid, fumaric acid, maleic acid, benzoic acid, salicyclic acid, phenylacetic acid, and mandelic acid. In addition, pharmaceutically acceptable salts include acid salts of inorganic bases, such as salts containing alkaline cations (e.g., $Li^+Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formula I possess asymmetric carbons and can therefore exist in racemic and optically active forms. Methods of separation of enantiomeric and diastereomeric mixtures are well known to one skilled in the art. The present invention encompasses any isolated racemic or optically active form of compounds described in Formula I which possess p38 kinase inhibitory activity.

General Preparative Methods

The compounds of Formula I may be prepared by use of known chemical reactions and procedures, some from starting materials which are commercially available. Nevertheless, the following general preparative methods are presented to aid one of skill in the art in synthesizing these compounds, with more detailed particular examples being presented in the experimental section describing the working examples.

Scheme I
Reduction of Nitroaryls to Aryl Amines

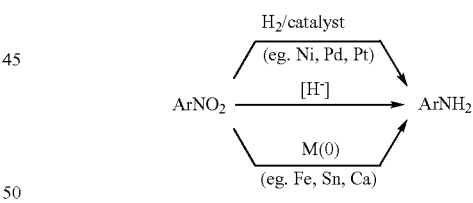

Nitroaryls are commonly formed by electrophilic aromatic nitration using $HNO_3$, or an alternative $NO_2^+$ source. Nitroaryls may be further elaborated prior to reduction. Thus, nitroaryls substituted with

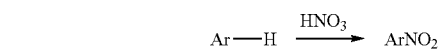

potential leaving groups (eg. F, Cl, Br, etc.) may undergo substitution reactions on treatment with nucleophiles, such as thiolate (exemplified in Scheme II) or phenoxide. Nitroaryls may also undergo Ullman-type coupling reactions (Scheme II).

Scheme II
Selected Nucleophilic Aromatic Substitution using Nitroaryls

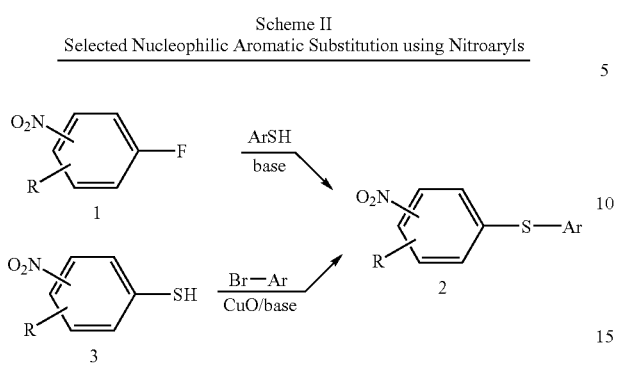

Nitroaryls may also undergo transition metal mediated cross coupling reactions. For example, nitroaryl electrophiles, such as nitroaryl bromides, iodides or triflates, undergo palladium mediated cross coupling reactions with aryl nucleophiles, such as arylboronic acids (Suzuki reactions, exemplified below) aryltins (Stille reactions) or arylzincs (Negishi reaction) to afford the biaryl (5).

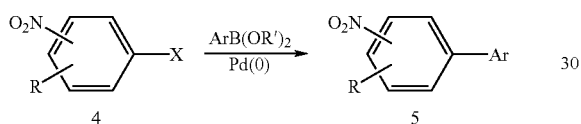

Either nitroaryls or anilines may be converted into the corresponding arenesulfonyl chloride (7) on treatment with chlorosulfonic acid. Reaction of the sulfonyl chloride with a fluoride source, such as KF then affords sulfonyl fluoride (8). Reaction of sulfonyl fluoride 8 with trimethylsilyl trifluoromethane in the presence of a fluoride source, such as tris(dimethylamino)sulfonium difluorotrimethylsiliconate (TASF) leads to the corresponding trifluoromethylsulfone (9). Alternatively, sulfonyl chloride 7 may be reduced to the arenethiol (10), for example with zinc amalgum. Reaction of thoil 10 with CHClF$_2$ in the presence of base gives the difluoromethyl mercaptam (11), which may be oxidized to the sulfone (12) with any of a variety of oxidants, including CrO$_3$-acetic anhydride (Sedova et al. *Zh. Org. Khim.* 1970, 6, 568).

Scheme III
Selected Methods of fluorinated Aryl Sulfone Synthesis

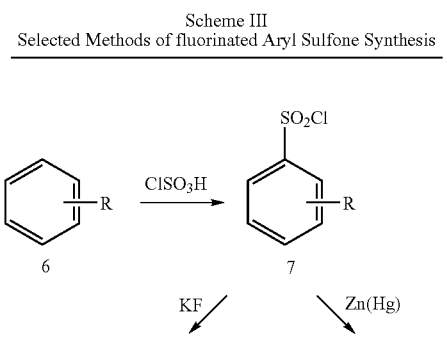

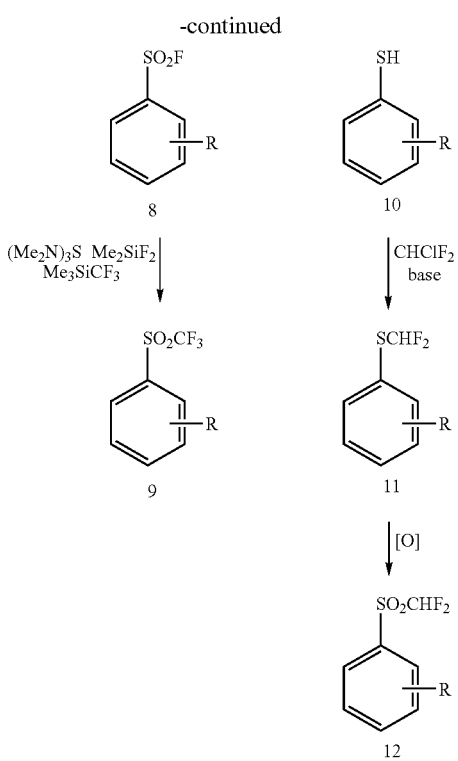

As shown in Scheme IV, non-symmetrical urea formation may involve reaction of an aryl isocyanate (14) with an aryl amine (13). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, following by rearrangement affords the isocyanate. The corresponding carboxylic acid (17) may also be subjected to Curtius-type rearrangements using diphenylphosphoryl azide (DPPA) or a similar reagent.

Scheme IV
Selected Methods of Non-Symmetrical Urea Formation

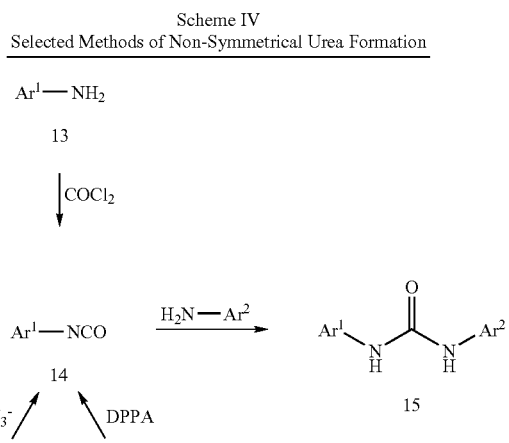

-continued

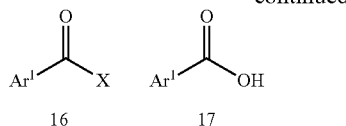

Finally, ureas may be further manipulated using methods familiar to those skilled in the art.

The invention also includes pharmaceutical compositions including a compound of Formula I, and a physiologically acceptable carrier.

The compounds may be administered orally, topically, parenterally, by inhalation or spray, vaginally, rectally or sublingually in dosage unit formulations. The term 'administration by injection' includes intravenous, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Compounds of the invention may also be administrated transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily vaginal dosage regimen will preferably be from 0.01 to 200 mg/Kg of total body weight. The daily rectal dosage regimen will preferably be from 0.01 to 200 mg/Kg of total body weight. The transdermal concentration will preferably be that required to maintain a daily dose of from 0.01 to 200 mg/Kg. The daily topical dosage regimen will preferably be from 0.1 to 200 mg administered between one to four times daily. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for a given patient depends on a variety of factors, including specific activity of the compound administered, the age of the patient, the body weight of the patient, the general health of the patient, the gender of the patient, the diet of the patient, time of administration, route of administration, rate of excretion, drug combination, and the severity of the condition undergoing therapy, etc. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional course of treatmment tests.

The compounds of FIG. I are producible from known compounds (or from starting materials which, in turn, are producible from known compounds), e.g., through the general preparative methods shown above. The activity of a given compound to inhibit raf kinase can be routinely assayed, e.g., according to procedures disclosed below. The following examples are for illustrative purposes only and are not intended, nor should they be construde to limit the invention in any way.

The entire disclosure of all applications, patents and publications cited above and below are hereby incorporated by reference, including provisional application serial number attorney docket number Bayer 10-V1, filed on Dec. 22, 1997 as Ser. No. 08/995,749, and converted on Dec. 22, 1998.

The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg.

All temperatures are reported uncorrected in degrees Celsius (° C.). Unless otherwise indicated, all parts and percentages are by weight.

Commercial grade reagents and solvents were used without further purification. Thin-layer chromatography (TLC) was performed using Whatman® pre-coated glass-backed silica gel 60A F-254 250 µm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Fourier transform infrared sprectra were obtained using a Mattson 4020 Galaxy Series spectrophotometer. Proton ($^1$H) nuclear magnetic resonance (NMR) spectra were measured with a General Electric GN-Omega 300 (300 MHz) spectrometer with either Me$_4$Si (d 0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer. Chemical ionization mass spectra (CI-MS) were obtained using a Hewlett Packard MS-Engine (5989A) with methane or ammonia as the reagent gas ($1 \times 10^{-4}$ torr to $2.5 \times 10^{-4}$ torr). The direct insertion desorption chemical ionization (DCI) probe (Vaccumetrics, Inc.) was ramped from 0-1.5 amps in 10 sec and held at 10 amps until all traces of the sample disappeared (~1-2 min). Spectra were scanned from 50-800 amu at 2 sec per scan. HPLC—electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source. Gas chromatography—ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses are conducted by Robertson Microlit Labs, Madison, N.J.

All compounds displayed NMR spectra, LRMS and either elemental analysis or HRMS consistant with assigned structures.

| List of Abbreviations and Acronyms: | |
|---|---|
| AcOH | acetic acid |
| anh | anhydrous |
| BOC | tert-butoxycarbonyl |
| conc | concentrated |
| dec | decomposition |
| DMPU | 1,3-dimethyl-3,4,5,6-tetrahydro-2(1H)-pyrimidinone |
| DMF | N,N-dimethylformamide |
| DMSO | dimethylsulfoxide |
| DPPA | diphenylphosphoryl azide |
| EtOAc | ethyl acetate |
| EtOH | ethanol (100%) |
| $Et_2O$ | diethyl ether |
| $Et_3N$ | triethylamine |
| m-CPBA | 3-chloroperoxybenzoic acid |
| MeOH | methanol |
| pet. ether | petroleum ether (boiling range 30-60° C.) |
| THF | tetrahydrofuran |
| TFA | trifluoroacetic acid |
| Tf | trifluoromethanesulfonyl |

A. General Methods for Synthesis of Substituted Anilines

A1. Synthesis of 2,5-Dioxopyrrolidinylanilines

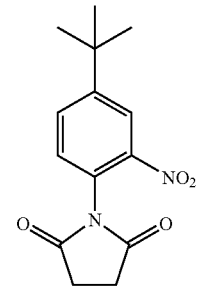

Step 1. 4-tert-Butyl-1-(2,5-dioxo-1-pyrrolidinyl)-2-nitrobenzene: To a solution of 4-tert-butyl-2-nitroaniline (1.04 g, 5.35 mmol) in xylene (25 mL) was added succinic anhydride (0.0535 g, 5.35 mmol) and triethylamine (0.75 mL, 5.35 mmol). The reaction mixture was heated at the reflux temp. for 24 h, cooled to room temp. and diluted with $Et_2O$ (25 mL). The resulting mixture was sequentially washed with a 10% HCl solution (50 mL), a saturated $NH_4Cl$ solution (50 mL) and a saturated NaCl solution (50 mL), dried ($MgSO_4$), and concentrated under reduced pressure. The residue was purified by flash cromatography (60% EtOAc/40% hexane) to yield the succinimide as a yellow solid (1.2 g, 86%): mp 135-138° C.; $^1$H NMR ($CHCl_3$) δ 1.38 (s, 9H), 2.94-2.96 (m, 4H), 7.29-7.31 (m, 1H), 7.74-7.78 (m, 1H), 8.18-8.19 (m, 1H).

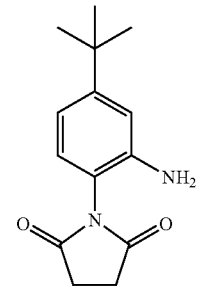

Step 2. 5-tert-Butyl-2-(2,5-dioxo-1-pyrrolidinyl)aniline: To a solution of 4-tert-butyl-1-(2,5-dioxo-1-pyrrolidinyl)-2-nitrobenzene (1.1 g, 4.2 mmol) in EtOAc (25 mL) was added a 10% Pd/C (0.1 g). The resulting slurry was placed under a $H_2$ atmosphere using 3 cycles of an evacuate-quench protocol and was allowed to stir under a $H_2$ atmosphere for 8 h. The reaction mixture was filtered through a pad of Celite® and the residue was washed with $CHCl_3$. The combined filtrate was concentrated under reduced pressure to yield the desired aniline as an off-white solid (0.75 g, 78%): mp 208-211° C.; $^1$H-NMR (DMSO-$d_6$) δ 1.23 (s, 9H), 2.62-2.76 (m, 4H), 5.10 (br s, 2H), 6.52-6.56 (m, 1H), 6.67-6.70 (m, 2H).

A2. General Method for the Synthesis of Tetrahydrofuranyloxyanilines

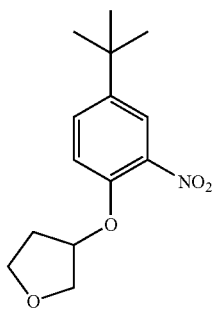

Step 1. 4-tert-Butyl-1-(3-tetrahydrofuranyloxy)-2-nitrobenzene: To a solution of 4-tert-butyl-2-nitrophenol (1.05 g, 5.4 mmol) in anh THF (25 mL) was added 3-hydroxytetrahydrofuran (0.47 g, 5.4 mmol) and triphenylphosphine (1.55 g, 5.9 mmol) followed by diethyl azodicarboxylate (0.93 ml, 5.9 mmol) and the mixture was allowed to stir at room temp. for 4 h. The resulting mixture was diluted with $Et_2O$ (50 mL) and washed with a saturated $NH_4Cl$ solution (50 mL) and a saturated NaCl solution (50 mL), dried ($MgSO_4$), and concentrated under reduced pressure. The residue was purified by flash cromatography (30% EtOAc/70% hexane) to yield the desired ether as a yellow solid (1.3 g, 91%): $^1$H-NMR ($CHCl_3$) δ 1.30 (s, 9H), 2.18-2.24 (m, 2H), 3.91-4.09 (m, 4H), 5.00-5.02 (m, 1H), 6.93 (d, J=8.8 Hz, 1H), 7.52 (dd, J=2.6, 8.8 Hz, 1H), 7.81 (d, J=2.6 Hz, 1H).

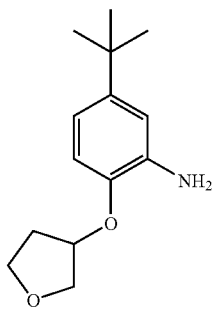

Step 2. 5-tert-Butyl-2-(3-tetrahydrofuranyloxy)aniline: To a solution of 4-tert-butyl-1-(3-tetrahydrofuranyloxy)-2-nitrobenzene (1.17 g, 4.4 mmol) in EtOAc (25 mL) was added 10% Pd/C (0.1). The resulting slurry was placed under a $H_2$ atmosphere using 3 cycles of an evacuate-quench protocol and was allowed to stir under a $H_2$ atmosphere for 8 h. The reaction mixture was filtered through a pad of Celite® and washed with $CHCl_3$. The combined filtrate was concentrated under reduced pressure to yield of the desired aniline as a yellow solid (0.89 g, 86%): mp 79-82° C.; $^1$H-NMR ($CHCl_3$) δ 1.30 (s, 9H), 2.16-2.20 (m, 2H), 3.78 (br s, 2H), 3.85-4.10 (m, 4H), 4.90 (m, 1H), 6.65-6.82 (m, 3H).

A3. General Method for the Synthesis of Trifluoromethanesulfonylanilines

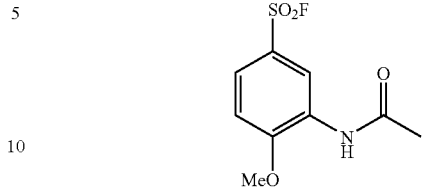

Step 1. 2-Methoxy-5-(fluorosulfonyl)acetanilide: Acetic anhydride (0.90 mL, 9.6 mmol) was added to a solution of 4-methoxymetanilyl fluoride (1.0 g, 4.8 mmol) in pyridine (15 mL). After being stirred at room temp. for 4 h, the reaction mixture was concentrated under reduced pressure. The resulting residue was dissolved in $CH_2Cl_2$ (25 mL), washed with a saturated $NaHCO_3$ solution (25 mL), dried ($Na_2SO_4$), and concentrated under reduced pressure to give a foam which was triturated with a $Et_2O$/hexane solution to provide the title compound (0.85 g): $^1$H-NMR ($CHCl_3$) δ 2.13 (s, 3H), 3.98 (s, 3H), 7.36 (d, J=8.5 Hz, 1H), 7.82 (dd, J=2.6, 8.8 Hz, 1H), 8.79 (d, J=2.2 Hz, 1H), 9.62 (br s, 1H).

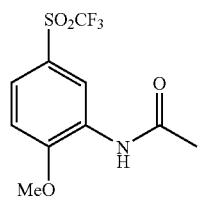

Step 2. 2-Methoxy-5-(trifluoromethanesulfonyl)acetanilide: To an ice-cooled suspension of tris(dimethylamino)sulfonium difluorotrimethylsiliconate (0.094 g, 0.34 mmol) in THF (4 mL) was added a solution of (trifluoromethyl)trimethylsilane (1.0 mL, 6.88 mmol) in THF (3 mL) followed by a solution of 2-methoxy-5-(fluorosulfonyl)acetanilide (0.85 g, 3.44 mmol) in THF (3 mL). The reaction mixture was stirred for 2 h on an ice bath, then was allowed to warm to room temp. and was then concentrated under reduced pressure. The resulting residue was dissolved in $CH_2Cl_2$ (25 mL), washed with water (25 mL), dried ($Na_2SO_4$), and concentrated under reduced pressure. The resulting material was purified by flash chromatography (3% MeOH/97% $CH_2Cl_2$) to provide the title compound as a white solid (0.62 g); $^1$H-NMR ($CHCl_3$) δ 2.13 (s, 3H), 4.00 (s, 3H), 7.42 (d, J=8.8 Hz, 1H), 7.81 (dd, J=2.6, 8.8 Hz, 1H), 8.80 (d, J=2.2 Hz, 1H), 9.64 (br s, 1H); FAB-MS m/z 298 ((M+1)$^+$).

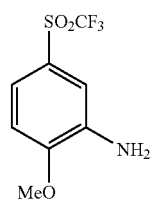

Step 3. 2-Methoxy-5-(trifluoromethanesulfonyl)aniline: A solution of 2-methoxy-5-(trifluoromethanesulfonyl)acetanilide (0.517 g, 1.74 mmol) in EtOH (5 mL) and a 1 N HCl solution (5 mL) was heated at the reflux temp. for 4 h and the resulting mixture was concentrated under reduced pressure. The residue was dissolved in CH$_2$Cl$_2$ (30 mL), washed with water (30 mL), dried (Na$_2$SO$_4$), and concentrated under reduced pressure to afford the title compound as a gum (0.33 g): $^1$H-NMR (CDCl$_3$) δ 3.90 (s, 3H) 5.57 (br s, 2H), 7.11-7.27 (m, 3H); FAB-MS m/z 256 ((M+1)$^+$). This material was used in urea formation without further purification.

A4. General Method for Aryl Amine Formation via Phenol Nitration Followed by Ether Formation and Reduction

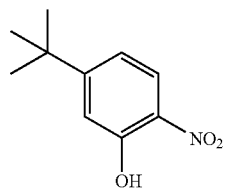

Step 1. 2-Nitro-5-tert-butylphenol: A mixture of fuming nitric acid (3.24 g, 77.1 mmol) in glacial HOAc (10 mL) was added dropwise to a solution of m-tert-butylphenol (11.58 g, 77.1 mmol) in glacial HOAc (15 mL) at 0° C. The mixture was allowed to stir at 0° C. for 15 min then warmed to room temp. After 1 h the mixture was poured into ice water (100 mL) and extracted with Et$_2$O (2×50 mL). The organic layer was washed with a saturated NaCl solution (100 mL), dried (MgSO$_4$) and concentrated in vacuo. The residue was purified by flash chromatography (30% EtOAc/70% hexane) to give the desired phenol (4.60 g, 31%): $^1$H-NMR (DMSO-d$_6$) δ 1.23 (s, 9H), 7.00 (dd, J=1.84, 8.83 Hz, 1H), 7.07 (d, J=1.84 Hz, 1H), 7.82 (d, J=8.83 Hz, 1H), 10.74 (s, 1H).

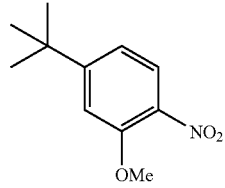

Step 2. 2-Nitro-5-tert-butylanisole: A slurry of 2-nitro-5-tert-butylphenol (3.68 g, 18.9 mmol) and K$_2$CO$_3$ (3.26 g, 23.6 mmol) in anh DMF (100 mL) was stirred at room temp with stirring for 15 min then treated with iodomethane (2.80 g, 19.8 mmol) via syringe. The reaction was allowed to stir at room temp for 18 h., then was treated with water (100 mL) and extracted with EtOAc (2×100 mL). The combined organic layers were washed with a saturated NaCl solution (50 mL), dried (MgSO$_4$) and concentrated in vacuo to give the desired ether (3.95 g, 100%): $^1$H-NMR (DMSO-d$_6$) δ 1.29 (s, 9H), 3.92 (s, 3H), 7.10 (dd, J=1.84, 8.46 Hz, 1H), 7.22 (d, J=1.84 Hz, 1H), 7.79 (d, J=8.46 Hz, 1H). This material was used in the next step without further purification.

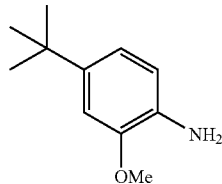

Step 3. 4-tert-Butyl-2-methoxyaniline: A solution of 2-nitro-5-tert-butylanisole (3.95 g, 18.9 mmol) in MeOH (65 mL) and added to a flask containing 10% Pd/C in MeOH (0.400 g), then placed under a H$_2$ atmosphere (balloon). The reaction was allowed to stir for 18 h at room temp, then filtered through a pad of Celite® and concentrated in vacuo to afford the desired product as a dark sitcky solid (3.40 g, 99%): $^1$H-NMR (DMSO-d$_6$) δ 1.20 (s, 9H), 3.72 (s, 3H), 4.43 (br s, 2H), 6.51 (d, J=8.09 Hz, 1H), 6.64 (dd, J=2.21, 8.09 Hz, 1H), 6.76 (d, J=2.21 Hz, 1H).

A5. General Method for Aryl Amine Formation via Carboxylic Acid Esterification Followed by Reduction

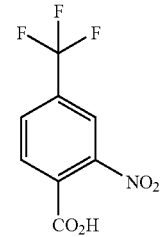

Step 1. Methyl 2-Nitro-4-(trifluoromethyl)benzoate: To a solution of 2-nitro-4-(trifluoromethyl)benzoic acid (4.0 g, 17.0 mmol) in MeOH (150 mL) at room temp was added conc H$_2$SO$_4$ (2.5 mL). The mixture was heated at the reflux temp for 25 h., cooled to room temp and concentrated in vacuo. The residue was diluted with water (100 mL) and extracted with EtOAc (2×10 mL). The combined organic layers were washed with a saturated NaCl solution, dried (MgSO$_4$), concentrated in vacuo. The residue was purified by flash chromatography (14% EtOAc/86% hexane) to give the desired ester as a pale yellow oil (4.17 g, 98%): $^1$H-NMR (DMSO-d$_6$) δ 3.87 (s, 3H), 8.09 (d, J=7.72 Hz, 1H), 8.25 (dd, J=1.11, 8.09 Hz, 1H), 8.48 (d, J=1.11 Hz, 1H).

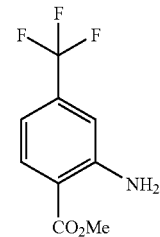

Step 2. Methyl 2-Amino-4-(trifluoromethyl)benzoate: A solution of methyl 2-nitro-4-(trifluoromethyl)benzoate (3.90 g, 15.7 mmol) in EtOAc (100 mL) and added to a flask containing 10% Pd/C (0.400 mg) in EtOAc (10 mL), then placed under a H$_2$ atmosphere (balloon). The reaction was allowed to stir for 18 h at room temp, then was filtered through Celite® and concentrated in vacuo to afford the desired product as a white crystalline solid (3.20 g, 93%): $^1$H-NMR (DMSO-$d_6$) δ 3.79 (s, 3H), 6.75 (dd, J=1.84, 8.46 Hz, 1H), 6.96 (br s, 2H), 7.11 (d, J=0.73 Hz, 1H), 7.83 (d, J=8.09 Hz, 1H).

A6. General Method for Aryl Amine Formation via Ether Formation Followed Ester Saponification, Curtius Rearrangement, and Carbamate Deprotection

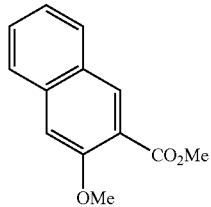

Step 1. Methyl 3-Methoxy-2-naphthoate: A slurry of methyl 3-hydroxy-2-naphthoate (10.1 g, 50.1 mmol) and $K_2CO_3$ (7.96 g, 57.6 mmol) in DMF (200 mL) was stirred at room temp for 15 min, then treated with iodomethane (3.43 mL, 55.1 mmol). The mixture was allowed to stir at room temp overnight, then was treated with water (200 mL). The resulting mixture was extracted with EtOAc (2×200 mL). The combined organic layers were washed with a saturated NaCl solution (100 mL), dried (MgSO$_4$), concentrated in vacuo (approximately 0.4 mmHg overnight) to give the desired ether as an amber oil (10.30 g): $^1$H-NMR (DMSO-$d_6$) δ 2.70 (s, 3H), 2.85 (s, 3H), 7.38 (app t, J=8.09 Hz, 1H), 7.44 (s, 1H), 7.53 (app t, J=8.09 Hz, 1H), 7.84 (d, J=8.09 Hz, 1H), 7.90 (s, 1H), 8.21 (s, 1H).

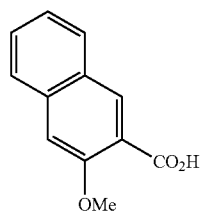

Step 2. 3-Methoxy-2-naphthoic Acid: A solution of methyl 3-methoxy-2-naphthoate (6.28 g, 29.10 mmol) and water (10 mL) in MeOH (100 mL) at room temp was treated with a 1 N NaOH solution (33.4 mL, 33.4 mmol). The mixture was heated at the reflux temp for 3 h, cooling to room temp, and made acidic with a 10% citric acid solution. The resulting solution was extracted with EtOAc (2×100 mL). The combined organic layers were washed with a saturated NaCl solution, dried (MgSO$_4$) and concentrated in vacuo. The residue was triturated with hexanes and washed several times with hexanes to give the desired carboxylic acid as a white crystalline solid (5.40 g, 92%): $^1$H-NMR (DMSO-$d_6$) δ 3.88 (s, 3H), 7.34-7.41 (m, 2H), 7.49-7.54 (m, 1H), 7.83 (d, J=8.09 Hz, 1H), 7.91 (d, J=8.09 Hz, 1H), 8.19 (s, 1H), 12.83 (br s, 1H).

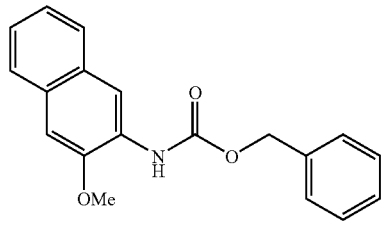

Step 3. 2-(N-(Carbobenzyloxy)amino-3-methoxynaphthalene: A solution of 3-methoxy-2-naphthoic acid (3.36 g, 16.6 mmol) and Et$_3$N (2.59 mL, 18.6 mmol) in anh toluene (70 mL) was stirred at room temp. for 15 min., then treated with a solution of diphenylphosphoryl azide (5.12 g, 18.6 mmol) in toluene (10 mL) via pipette. The resulting mixture was heated at 80° C. for 2 h. After cooling the mixture to room temp. benzyl alcohol (2.06 mL, 20 mmol) was added via syringe. The mixture was then warmed to 80° C. overnight. The resulting mixture was cooled to room temp., quenched with a 10% citric acid solution, and extracted with EtOAc (2×100 mL). The combined organic layers were washed with a saturated NaCl solution, dried (MgSO$_4$), and concentrated in vacuo. The residue was purified by flash chromatography (14% EtOAc/86% hexane) to give the benzyl carbamate as a pale yellow oil (5.1 g, 100%): $^1$H-NMR (DMSO-$d_6$) δ 3.89 (s, 3H), 5.17 (s, 2H), 7.27-7.44 (m, 8H), 7.72-7.75 (m, 2H), 8.20 (s, 1H), 8.76 (s, 1H).

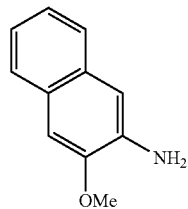

Step 4. 2-Amino-3-methoxynaphthalene: A slurry of 2-(N-(carbobenzyloxy)amino-3-methoxynaphthalene (5.0 g, 16.3 mmol) and 10% Pd/C (0.5 g) in EtOAc (70 mL) was maintained under a H$_2$ atmospheric (balloon) at room temp. overnight. The resulting mixture was filtered through Celite® and concentrated in vacuo to give the desired amine as a pale pink powder (2.40 g, 85%): $^1$H-NMR (DMSO-$d_6$) δ 3.86 (s, 3H), 6.86 (s, 2H), 7.04-7.16 (m, 2H), 7.43 (d, J=8.0 Hz, 1H), 7.56 (d, J=8.0 Hz, 1H); EI-MS m/z 173 (M$^+$).

A7. General Method for the Synthesis of Aryl Amines via Metal-Mediated Cross Coupling Followed by Reduction

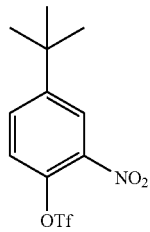

Step 1. 5-tert-Butyl-2-(trifluoromethanesulfonyl)oxy-1-nitrobenzene: To an ice cold solution of 4-tert-butyl-2-nitrophenol (6.14 g, 31.5 mmol) and pyridine (10 mL, 125 mmol) in CH$_2$Cl$_2$ (50 mL) was slowly added trifluoromethanesulfonic anhydride (10 g, 35.5 mmol) via syringe. The reaction mixture was stirred for 15 min, then allowed to warm up to room temp. and diluted with CH$_2$Cl$_2$ (100 mL). The resulting mixture was sequentially washed with a 1M NaOH solution (3×100 mL), and a 1M HCl solution (3×100 mL), dried (MgSO$_4$), and concentrated under reduced pressure to afford the title compound (8.68 g, 84%): $^1$H-NMR (CDCl$_3$) δ 1.39 (s, 9H), 7.30-8.20 (m, 3H).

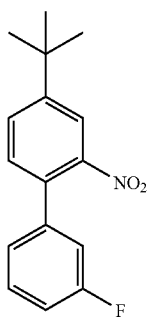

Step 2. 5-tert-Butyl-2-(3-fluorophenyl)-1-nitrobenzene: A mixture of 3-fluorobenzeneboronic acid (3.80 g, 27.5 mmol), KBr (2.43 g, 20.4 mmol), K$_3$PO$_4$ (6.1 g, 28.8 mmol), and Pd(PPh$_3$)$_4$ (1.0 g, 0.9 mmol) was added to a solution of 5-tert-butyl-2-(trifluoromethanesulfonyl)oxy-1-nitrobenzene (6.0 g, 18.4 mmol) in dioxane (100 mL). The reaction mixture was heated at 80° C. for 24 h, at which time TLC indicated complete reaction. The reaction mixture was treated with a saturated NH$_4$Cl solution (50 mL) and extracted EtOAc (3×100 mL). The combined organic layers were dried (MgSO$_4$) and concentrated under reduced pressure. The residue was purified by flash chromatography (3% EtOAc/97% hexane) to give the title compound (4.07 g, 81%): $^1$H-NMR (CDCl$_3$) δ 1.40 (s, 9H), 6.90-7.90 (m, 7H).

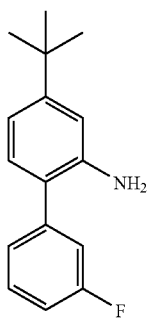

Step 3. 5-tert-Butyl-2-(3-fluorophenyl)aniline: To a solution of 5-tert-butyl-2-(3-fluorophenyl)-1-nitrobenzene (3.5 g, 12.8 mmol) and EtOH (24 mL) in EtOAc (96 mL) was added 5% Pd/C (0.350 g) and the resulting slurry was stirred under a H$_2$ atmosphere for 24 h, at which time TLC indicated complete consumption of starting material. The reaction mixture was filtered through a pad of Celite® to give the desired product (2.2 g, 72%): $^1$H-NMR (CDCl$_3$) δ 1.35 (s, 9H), 3.80 (br s, 2H), 6.90-7.50 (m, 7H).

A8. General Method for the Synthesis of Nitroanilines

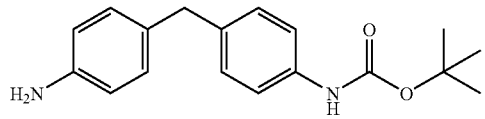

Step 1. 4-(4-(2-Propoxycarbonylamino)phenyl)methylaniline: A solution of di-tert-butyl dicarbonate (2.0 g, 9.2 mmol) and 4,4'-methylenedianiline (1.8 g, 9.2 mmol) in DMF (100 mL) was heated at the reflux temp. for 2 h, then cooled to room temp. This mixture was diluted with EtOAc (200 mL) sequentially washed with a saturated NH$_4$Cl (200 mL) and a saturated NaCl solution (100 mL), and dried (MgSO$_4$). The residue was purified by flash chromatography (30% EtOAc/70% hexane) to give the desired carbamate (1.3 g, 48%): $^1$H-NMR (CDCl$_3$) δ 1.51 (s, 9H), 3.82 (s, 2H), 6.60-7.20 (m, 8H).

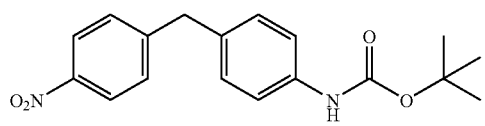

Step 2. 4-(4-(2-Propoxycarbonylamino)phenyl)methyl-1-nitrobenzene: To an ice cold solution of 4-(4-(2-propoxycarbonylamino)phenyl)methylaniline (1.05 g, 3.5 mmol) in CH$_2$Cl$_2$ (15 mL) was added m-CPBA (1.2 g, 7.0 mmol). The reaction mixture was slowly allowed to warm to room temp. and was stirred for 45 min, at which time TLC indicated disappearance of starting material. The resulting mixture was diluted with EtOAc (50 mL), sequentially washed with a 1M NaOH solution (50 mL) and a saturated NaCl solution (50 mL), and dried (MgSO$_4$). The residue was purified by chromatography (20% EtOAc/80% hexane) to give the desired nitrobenzene (0.920 g): FAB-MS m/z 328 (M$^+$).

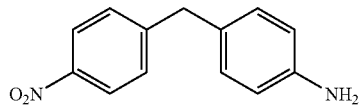

Step 3. 4-(4-Nitrophenyl)methylaniline: To a solution of 4-(4-(2-propoxycarbonylamino)phenyl)methyl-1-nitrobenzene (0.920 g, 2.8 mmol) in dioxane (10 mL) was added a conc. HCl solution (4.0 mL) and the resulting mixture was heated at 80° C. for 1 h at which time TLC indicated disappearance of starting material. The reaction mixture was cooled to room temp. The resulting mixture was diluted with EtOAc (50 mL), then washed with a 1M NaOH solution (3×50 mL), and dried (MgSO$_4$) to give the desired aniline (0.570 mg, 89%): $^1$H-NMR (CDCl$_3$) δ 3.70 (br s, 2H), 3.97 (s, 2H), 6.65 (d, J=8.5 Hz, 2H), 6.95 (d, J=8.5 Hz, 2H), 7.32 (d, J=8.8 Hz, 2H), 8.10 (d, J=8.8 Hz, 2H).

A9. General Method for Synthesis of Aryl Anilines via Alkylation of a Nitrophenol Followed by Reduction

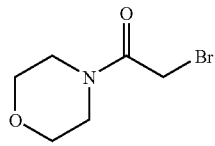

Step 1. 4-(α-Bromoacetyl)morpholine: To an ice cold solution of morpholine (2.17 g, 24.9 mmol) and diisopropylethylamine (3.21 g, 24.9 mmol) in $CH_2Cl_2$ (70 mL) was added a solution of bromoacetyl bromide (5.05 g, 25 mmole) in $CH_2Cl_2$ (8 mL) via syringe. The resulting solution was kept at 0° C. for 45 min, then was allowed to warm to room temp. The reaction mixture was diluted with EtOAc (500 mL), sequentially washed with a 1M HCl solution (250 mL) and a saturated NaCl solution (250 mL), and dried ($MgSO_4$) to give the desired product (3.2 g, 62%): $^1$H-NMR (DMSO-$d_6$) δ 3.40-3.50 (m, 4H), 3.50-3.60 (m, 4H), 4.11 (s, 2H).

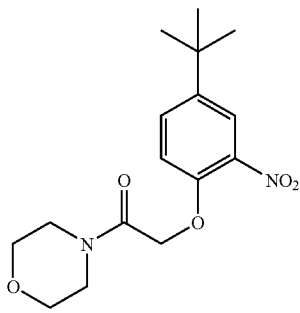

Step 2. 2-(N-Morpholinylcarbonyl)methoxy-5-tert-butyl-1-nitrobenzene: A slurry of 4-tert-butyl-2-nitrophenol (3.9 g, 20 mmol) and $K_2CO_3$ (3.31 g, 24 mmol) in DMF (75 mL) was stirred at room temp. for 15 minutes, then a solution of 4-(α-bromoacetyl)morpholine (4.16 g, 20 mmol) in DMF (10 mL) was added. The reaction was allowed to stir at room temp. overnight, then was diluted with EtOAc (500 mL) and sequentially washed with a saturated NaCl solution (4×200 mL) and a 1M NaOH solution (400 mL). The residue was purified by flash chromatography (75% EtOAc/25% hexane) to give the nitrobenzene (2.13 g, 33%): $^1$H-NMR (DMSO-$d_6$) δ 1.25 (s, 9H), 3.35-3.45 (m, 4H), 3.50-3.58 (m, 4H), 5.00 (s, 2H), 7.12 (d, J=8.8 Hz, 1H), 7.50-7.80 (m, 2H).

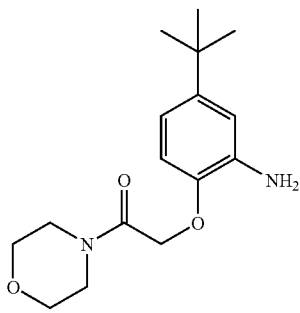

Step 3. 2-(N-Morpholinylcarbonyl)methoxy-5-tert-butylaniline: To a solution of 2-(N-morpholinylcarbonyl)methoxy-5-tert-butyl-1-nitrobenzene (2.13 g, 6.6 mmol) and EtOH (10 mL) in EtOAc (40 mL) was added 5% Pd/C (0.215 g). The resulting slurry was stirred under a $H_2$ atmosphere for 6 h, at which time TLC indicated complete consumption of starting material. The reaction mixture was filtered through a pad of Celite® to give the desired product (1.9 g, 98%): $^1$H-NMR (DMSO-$d_6$) δ 1.18 (s, 9H), 3.40-3.50 (m, 4H), 3.50-3.60 (m, 4H), 4.67 (br s, 2H), 4.69 (s, 2H), 6.40-6.70 (m, 3H).

A10. General Method for Aryl Amine Formation via Nitrophenol Alkylation Followed by Reduction

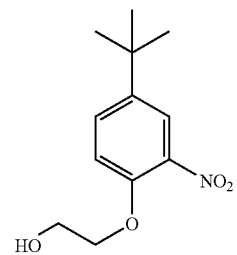

Step 1. 5-tert-Butyl-2-(2-hydroxyethoxy)-1-nitrobenzene: A solution of 4-tert-butyl-2-nitrophenol (30 g, 0.15 mol) and tetra-n-butylammonium fluoride (0.771 g, 3.0 mmol) in ethylene carbonate (10.24 mL, 0.15 mol) was heated at 150° C. for 18 h, then cooled to room temp. and separated between water (50 mL) and $CH_2Cl_2$ (50 mL). The organic layer was dried ($MgSO_4$) and concentrated under reduced pressure. The residue was purified by column chromatography (20% EtOAc/80% hexane) to afford the desired product as a brown oil (35.1 g, 90%): $^1$H-NMR (DMSO-$d_6$) δ 1.25 (s, 9H), 3.66-3.69 (m, 2H), 4.10-4.14 (t, J=5.0 Hz, 2H), 4.85 (t, J=5.0 Hz, 1H), 7.27 (d, J=8.8 Hz, 1H), 7.60-7.64 (m, 1H), 7.75 (d, J=2.6 Hz, 1H).

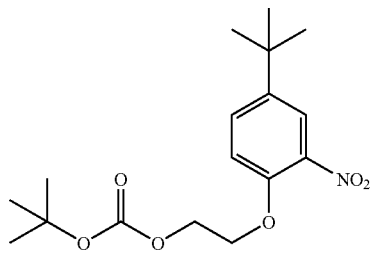

Step 2. 5-tert-Butyl-2-(2-tert-butoxycarbonyloxy)ethoxy)-1-nitrobenzene: A solution of 5-tert-butyl-2-(2-hydroxyethoxy)-1-nitrobenzene (0.401 g, 1.68 mmol), di-tert-butyl dicarbonate (0.46 mL, 2.0 mmol) and dimethylaminopyridine (0.006 g, 0.05 mmol) in $CH_2Cl_2$ (15 mL) was stirred at room temp. for 30 min, at which time TLC indicated consumption of starting material. The resulting mixture was washed with water (20 mL), dried ($MgSO_4$) and concentrated under reduced pressure. The residue was purified by column chromatography (3% MeOH/97% $CH_2Cl_2$) to give the desired product as a yellow oil (0.291 g, 51%): $^1$H-NMR (DMSO-$d_6$) δ 1.25 (s, 9H), 1.38 (s, 9H), 4.31 (br s, 4H), 7.27 (d, J=9.2 Hz, 1H) 7.64 (dd, J=2.6, 8.8 Hz, 1H) 7.77 (d, J=2.6 Hz, 1H).

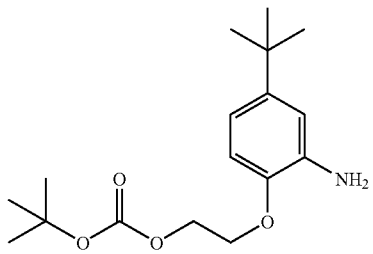

Step 3. 5-tert-Butyl-2-(2-tert-butoxycarbonyloxy)ethoxy) aniline: To a mixture of 5-tert-butyl-2-(2-tert-butoxycarbonyloxy)ethoxy)-1-nitrobenzene (0.290 g, 0.86 mmol) and 5% Pd/C (0.058 g) in MeOH (2 mL) was ammonium formate (0.216 g, 3.42 mmol), and the resulting mixture was stirred at room temp. for 12 h, then was filtered through a pad of Celite® with the aid of EtOH. The filtrate was concentrated under reduced pressure and the residue was purified by column chromatography (2% MeOH/98% $CH_2Cl_2$) tp give the desired product as a pale yellow oil (0.232 g, 87%): TLC (20% EtOAc/80% hexane) $R_f$ 0.63; $^1$H-NMR (DMSO-$d_6$) δ 1.17 (s, 9H), 1.39 (s, 9H), 4.03-4.06 (m, 2H), 4.30-4.31 (m, 2H), 4.54 (br s, 2H), 6.47 (dd, J=2.2, 8.1 Hz, 1H) 6.64-6.67 (m, 2H).

A11. General Method for Substituted Aniline Formation via Hydrogenation of a Nitroarene

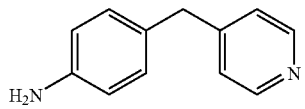

4-(4-Pyridinylmethyl)aniline: To a solution of 4-(4-nitrobenzyl)pyridine (7.0 g, 32.68 mmol) in EtOH (200 mL) was added 10% Pd/C (0.7 g) and the resulting slurry was shaken under a $H_2$ atmosphere (50 psi) using a Parr shaker. After 1 h, TLC and $^1$H-NMR of an aliquot indicated complete reaction. The mixture was filtered through a short pad of Celite®. The filtrate was concentrated in vacuo to afford a white solid (5.4 g, 90%): $^1$H-NMR (DMSO-$d_6$) δ 3.74 (s, 2H), 4.91 (br s, 2H), 6.48 (d, J=8.46 Hz, 2H), 6.86 (d, J=8.09 Hz, 2H), 7.16 (d, J=5.88 Hz, 2H), 8.40 (d, J=5.88 Hz, 2H); EI-MS m/z 184 ($M^+$). This material was used in urea formation reactions without further purification.

A12. General Method for Substituted Aniline Formation via Dissolving Metal Reduction of a Nitroarene

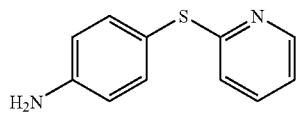

4-(2-Pyridinylthio)aniline: To a solution of 4-(2-pyridinylthio)-1-nitrobenzene (Menai ST 3355A; 0.220 g, 0.95 mmol) and $H_2O$ (0.5 mL) in AcOH (5 mL) was added iron powder (0.317 g, 5.68 mmol) and the resulting slurry stirred for 16 h at room temp. The reaction mixture was diluted with EtOAc (75 mL) and $H_2O$ (50 mL), basified to pH 10 by adding solid $K_2CO_3$ in portions (Caution: foaming). The organic layer was washed with a saturated NaCl solution, dried (MgSO$_4$), concentrated in vacuo. The residual solid was purified by MPLC (30% EtOAc/70% hexane) to give the desired product as a thick oil (0.135 g, 70%): TLC (30% EtOAc/70% hexanes) $R_f$ 0.20.

A13a. General Method for Substituted Aniline Formation via Nitroarene Formation Through Nucleophilic Aromatic Substitution, Followed by Reduction

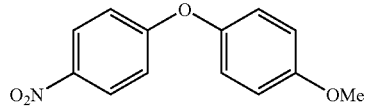

Step 1. 1-Methoxy-4-(4-nitrophenoxy)benzene: To a suspension of NaH (95%, 1.50 g, 59 mmol) in DMF (100 mL) at room temp. was added dropwise a solution of 4-methoxyphenol (7.39 g, 59 mmol) in DMF (50 mL). The reaction was stirred 1 h, then a solution of 1-fluoro-4-nitrobenzene (7.0 g, 49 mmol) in DMF (50 mL) was added dropwise to form a dark green solution. The reaction was heated at 95° C. overnight, then cooled to room temp., quenched with $H_2O$, and concentrated in vacuo. The residue was partitioned between EtOAc (200 mL) and $H_2O$ (200 mL). The organic layer was sequentially washed with $H_2O$ (2×200 mL), a saturated NaHCO$_3$ solution (200 mL), and a saturated NaCl solution (200 mL), dried (Na$_2$SO$_4$), and concentrated in vacuo. The residue was triturated (Et$_2$O/hexane) to afford 1-methoxy-4-(4-nitrophenoxy)benzene (12.2 g, 100%): $^1$H-NMR (CDCl$_3$) δ 3.83 (s, 3H), 6.93-7.04 (m, 6H), 8.18 (d, J=9.2 Hz, 2H); EI-MS m/z 245 ($M^+$).

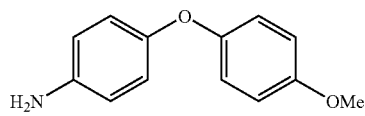

Step 2. 4-(4-Methoxyphenoxy)aniline: To a solution of 1-methoxy-4-(4-nitrophenoxy)benzene (12.0 g, 49 mmol) in EtOAc (250 mL) was added 5% Pt/C (1.5 g) and the resulting slurry was shaken under a $H_2$ atmosphere (50 psi) for 18 h. The reaction mixture was filtered through a pad of Celite® with the aid of EtOAc and concentrated in vacuo to give an oil which slowly solidified (10.6 g, 100%): $^1$H-NMR (CDCl$_3$) δ 3.54 (br s, 2H), 3.78 (s, 3H), 6.65 (d, J=8.8 Hz, 2H), 6.79-6.92 (m, 6H); EI-MS m/z 215 ($M^+$).

A13b. General Method for Substituted Aniline Formation via Nitroarene Formation Through Nucleophilic Aromatic Substitution, Followed by Reduction

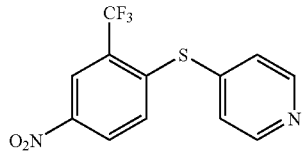

Step 1. 3-(Trifluoromethyl)-4-(4-pyridinylthio)nitrobenzene: A solution of 4-mercaptopyridine (2.8 g, 24 mmoles), 2-fluoro-5-nitrobenzotrifluoride (5 g, 23.5 mmoles), and potassium carbonate (6.1 g, 44.3 mmoles) in anhydrous DMF (80 mL) was stirred at room temperature and under argon overnight. TLC showed complete reaction. The mixture was diluted with Et$_2$O (100 mL) and water (100 mL) and the aqueous layer was back-extracted with Et$_2$O (2×100 mL). The organic layers were washed with a saturated NaCl solution (100 mL), dried (MgSO$_4$), and concentrated under reduced pressure. The solid residue was triturated with Et$_2$O to afford the desired product as a tan solid (3.8 g, 54%): TLC (30% EtOAc/70% hexane) R$_f$ 0.06; $^1$H-NMR (DMSO-d$_6$) δ 7.33 (dd, J=1.2, 4.2 Hz, 2H), 7.78 (d, J=8.7 Hz, 1H), 8.46 (dd, J=2.4, 8.7 Hz, 1H), 8.54-8.56 (m, 3H).

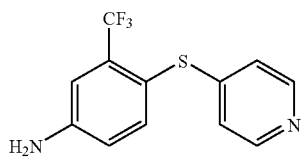

Step 2. 3-(Trifluoromethyl)-4-(4-pyridinylthio)aniline: A slurry of 3-trifluoromethyl-4-(4-pyridinylthio)nitrobenzene (3.8 g, 12.7 mmol), iron powder (4.0 g, 71.6 mmol), acetic acid (100 mL), and water (1 mL) were stirred at room temp. for 4 h. The mixture was diluted with Et$_2$O (100 mL) and water (100 mL). The aqueous phase was adjusted to pH 4 with a 4 N NaOH solution. The combined organic layers were washed with a saturated NaCl solution (100 mL), dried (MgSO$_4$), and concentrated under reduced pressure. The residue was filtered through a pad of silica (gradient from 50% EtOAc/50% hexane to 60% EtOAc/40% hexane) to afford the desired product (3.3 g): TLC (50% EtOAc/50% hexane) R$_f$ 0.10; $^1$H-NMR (DMSO-d$_6$) δ 6.21 (s, 2H), 6.84-6.87 (m, 3H), 7.10 (d, J=2.4 Hz, 1H), 7.39 (d, J=8.4 Hz, 1H), 8.29 (d, J=6.3 Hz, 2H).

A13c. General Method for Substituted Aniline Formation via Nitroarene Formation Through Nucleophilic Aromatic Substitution, Followed by Reduction

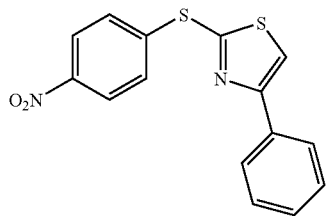

Step 1. 4-(2-(4-Phenyl)thiazolyl)thio-1-nitrobenzene: A solution of 2-mercapto-4-phenylthiazole (4.0 g, 20.7 mmoles) in DMF (40 mL) was treated with 1-fluoro-4-nitrobenzene (2.3 mL, 21.7 mmoles) followed by K$_2$CO$_3$ (3.18 g, 23 mmol), and the mixture was heated at approximately 65° C. overnight. The reaction mixture was then diluted with EtOAc (100 mL), sequentially washed with water (100 mL) and a saturated NaCl solution (100 mL), dried (MgSO$_4$) and concentrated under reduced pressure. The solid residue was triturated with a Et$_2$O/hexane solution to afford the desired product (6.1 g): TLC (25% EtOAc/75% hexane) R$_f$ 0.49; $^1$H-NMR (CDCl$_3$) δ 7.35-7.47 (m, 3H), 7.58-7.63 (m, 3H), 7.90 (d, J=6.9 Hz, 2H), 8.19 (d, J=9.0 Hz, 2H).

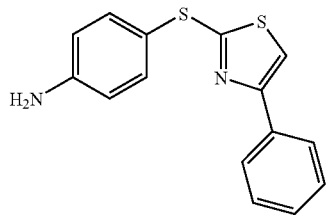

Step 2. 4-(2-(4-Phenyl)thiazolyl)thioaniline: 4-(2-(4-Phenyl)thiazolyl)thio-1-nitro-benzene was reduced in a manner analagous to that used in the preparation of 3-(trifluoromethyl)-4-(4-pyridinylthio)aniline: TLC (25% EtOAc/75% hexane) R$_f$ 0.18; $^1$H-NMR (CDCl$_3$) δ 3.89 (br s, 2H), 6.72-6.77 (m, 2H), 7.26-7.53 (m, 6H), 7.85-7.89 (m, 2H).

A13d. General Method for Substituted Aniline Formation via Nitroarene Formation Through Nucleophilic Aromatic Substitution, Followed by Reduction

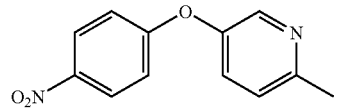

Step 1. 4-(6-Methyl-3-pyridinyloxy)-1-nitrobenzene: To a solution of 5-hydroxy-2-methylpyridine (5.0 g, 45.8 mmol) and 1-fluoro-4-nitrobenzene (6.5 g, 45.8 mmol) in anh DMF (50 mL) was added K$_2$CO$_3$ (13.0 g, 91.6 mmol) in one portion. The mixture was heated at the reflux temp. with stirring for 18 h and then allowed to cool to room temp. The resulting mixture was poured into water (200 mL) and extracted with EtOAc (3×150 mL). The combined organics were sequentially washed with water (3×100 mL) and a saturated NaCl solution (2×100 mL), dried (Na$_2$SO$_4$), and concentrated in vacuo to afford the desired product (8.7 g, 83%). The this material was carried to the next step without further purification.

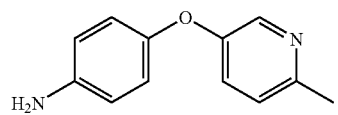

Step 2. 4-(6-Methyl-3-pyridinyloxy)aniline: A solution of 4-(6-methyl-3-pyridinyloxy)-1-nitrobenzene (4.0 g, 17.3 mmol) in EtOAc (150 mL) was added to 10% Pd/C (0.500 g, 0.47 mmol) and the resulting mixture was placed under a H$_2$ atmosphere (balloon) and was allowed to stir for 18 h at room temp. The mixture was then filtered through a pad of Celite® and concentrated in vacuo to afford the desired product as a tan solid (3.2 g, 92%): EI-MS m/z 200 (M$^+$).

A13e. General Method for Substituted Aniline Formation via Nitroarene Formation Through Nucleophilic Aromatic Substitution, Followed by Reduction

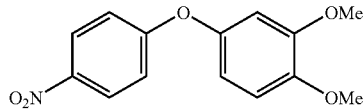

Step 1. 4-(3,4-Dimethoxyphenoxy)-1-nitrobenzene: To a solution of 3,4-dimethoxyphenol (1.0 g, 6.4 mmol) and 1-fluoro-4-nitrobenzene (700 μL, 6.4 mmol) in anh DMF (20 mL) was added $K_2CO_3$ (1.8 g, 12.9 mmol) in one portion. The mixture was heated at the reflux temp was stirring for 18 h and then allowed to cool to room temp. The mixture was then poured into water (100 mL) and extracted with EtOAc (3×100 mL). The combined organics were sequentially washed with water (3×50 mL) and a saturated NaCl solution (2×50 mL), dried ($Na_2SO_4$), and concentrated in vacuo to afford the desired product (0.8 g, 54%). The crude product was carried to the next step without further purification.

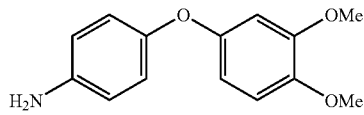

Step 2. 4-(3,4-Dimethoxyphenoxy)aniline: A solution of 4-(3,4-dimethoxy-phenoxy)-1-nitrobenzene (0.8 g, 3.2 mmol) in EtOAc (50 mL) was added to 10% Pd/C (0.100 g) and the resulting mixture was placed under a $H_2$ atmosphere (balloon) and was allowed to stir for 18 h at room temp. The mixture was then filtered through a pad of Celite® and concentrated in vacuo to afford the desired product as a white solid (0.6 g, 75%): EI-MS m/z 245 ($M^+$).

A13f. General Method for Substituted Aniline Formation via Nitroarene Formation Through Nucleophilic Aromatic Substitution, Followed by Reduction

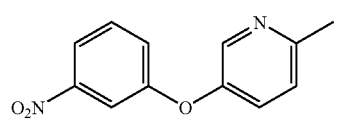

Step 1. 3-(3-Pyridinyloxy)-1-nitrobenzene: To a solution of 3-hydroxypyridine (2.8 g, 29.0 mmol), 1-bromo-3-nitrobenzene (5.9 g, 29.0 mmol) and copper(I) bromide (5.0 g, 34.8 mmol) in anh DMF (50 mL) was added $K_2CO_3$ (8.0 g, 58.1 mmol) in one portion. The resulting mixture was heated at the reflux temp. with stirring for 18 h and then allowed to cool to room temp. The mixture was then poured into water (200 mL) and extracted with EtOAc (3×150 mL). The combined organics were sequentially washed with water (3×100 mL) and a saturated NaCl solution (2×100 mL), dried ($Na_2SO_4$), and concentrated in vacuo. The resulting oil was purified by flash chromatography (30% EtOAc/70% hexane) to afford the desired product (2.0 g, 32%). This material was used in the next step without further purification.

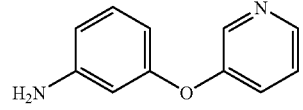

Step 2. 3-(3-Pyridinyloxy)aniline: A solution of 3-(3-pyridinyloxy)-1-nitrobenzene (2.0 g, 9.2 mmol) in EtOAc (100 mL) was added to 10% Pd/C (0.200 g) and the resulting mixture was placed under a $H_2$ atmosphere (balloon) and was allowed to stir for 18 h at room temp. The mixture was then filtered through a pad of Celite® and concentrated in vacuo to afford the desired product as a red oil (1.6 g, 94%): EI-MS m/z 186 ($M^+$).

A13g. General Method for Substituted Aniline Formation via Nitroarene Formation Through Nucleophilic Aromatic Substitution, Followed by Reduction

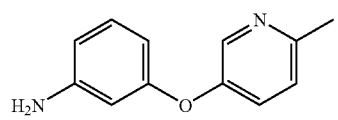

Step 1. 3-(5-Methyl-3-pyridinyloxy)-1-nitrobenzene: To a solution of 3-hydroxy-5-methylpyridine (5.0 g, 45.8 mmol), 1-bromo-3-nitrobenzene (12.0 g, 59.6 mmol) and copper(I) iodide (10.0 g, 73.3 mmol) in anh DMF (50 mL) was added $K_2CO_3$ (13.0 g, 91.6 mmol) in one portion. The mixture was heated at the reflux temp. with stirring for 18 h and then allowed to cool to room temp. The mixture was then poured into water (200 mL) and extracted with EtOAc (3×150 mL). The combined organics were sequentially washed with water (3×100 mL) and a saturated NaCl solution (2×100 mL), dried ($Na_2SO_4$), and concentrated in vacuo. The resulting oil was purified by flash chromatography (30% EtOAc/70% hexane) to afford the desired product (1.2 g, 13%).

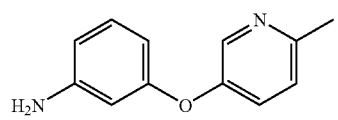

Step 2. 3-(5-Methyl-3-pyridinyloxy)-1-nitrobenzene: A solution of 3-(5-methyl-3-pyridinyloxy)-1-nitrobenzene (1.2 g, 5.2 mmol) in EtOAc (50 mL) was added to 10% Pd/C (0.100 g) and the resulting mixture was placed under a $H_2$ atmosphere (balloon) and was allowed to stir for 18 h at room temp. The mixture was then filtered through a pad of Celite® and concentrated in vacuo to afford the desired product as a red oil (0.9 g, 86%): CI-MS m/z 201 (($M+H)^+$).

A13h. General Method for Substituted Aniline Formation via Nitroarene Formation Through Nucleophilic Aromatic Substitution, Followed by Reduction

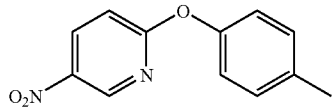

Step 1. 5-Nitro-2-(4-methylphenoxy)pyridine: To a solution of 2-chloro-5-nitropyridine (6.34 g, 40 mmol) in DMF (200 mL) were added of 4-methylphenol (5.4 g, 50 mmol, 1.25 equiv) and $K_2CO_3$ (8.28 g, 60 mmol, 1.5 equiv). The mixture was stirred overnight at room temp. The resulting mixture was treated with water (600 mL) to generate a precipitate. This mixture was stirred for 1 h, and the solids were separated and sequentially washed with a 1 N NaOH solution (25 mL), water (25 mL) and pet ether (25 mL) to give the desired product (7.05 g, 76%): mp 80-82° C.; TLC (30% EtOAc/70% pet ether) $R_f$ 0.79; $^1$H-NMR (DMSO-$d_6$) δ 2.31 (s, 3H), 7.08 (d, J=8.46 Hz, 2H), 7.19 (d, J=9.20 Hz, 1H), 7.24 (d, J=8.09 Hz, 2H), 8.58 (dd, J=2.94, 8.82 Hz, 1H), 8.99 (d, J=2.95 Hz, 1H); FAB-MS m/z (rel abundance) 231 ((M+H)$^+$, 100%).

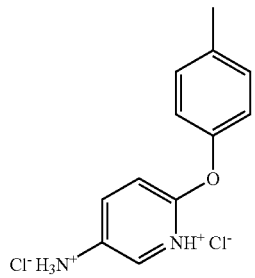

Step 2. 5-Amino-2-(4-methylphenoxy)pyridine Dihydrochloride: A solution 5-nitro-2-(4-methylphenoxy)pyridine (6.94 g, 30 mmol, 1 eq) and EtOAc (10 mL) in EtOAc (190 mL) was purged with argon then treated with 10% Pd/C (0.60 g). The reaction mixture was then placed under a $H_2$ atmosphere and was vigorously stirred for 2.5 h. The reaction mixture was filtered through a pad of Celite®. A solution of HCl in $Et_2O$ was added to the filtrate was added dropwise. The resulting precipitate was separated and washed with EtOAc to give the desired product (7.56 g, 92%): mp 208-210° C. (dec); TLC (50% EtOAc/50% pet ether) $R_f$ 0.42; $^1$H-NMR (DMSO-$d_6$) δ 2.25 (s, 3H), 6.98 (d, J=8.45 Hz, 2H), 7.04 (d, J=8.82 Hz, 1H), 7.19 (d, J=8.09 Hz, 2H), 8.46 (dd, J=2.57, 8.46 Hz, 1H), 8.63 (d, J=2.57 Hz, 1H); EI-MS m/z (rel abundance) (M$^+$, 100%).

A13i. General Method for Substituted Aniline Formation via Nitroarene Formation Through Nucleophilic Aromatic Substitution, Followed by Reduction

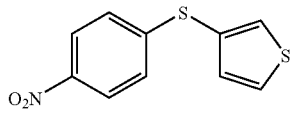

Step 1. 4-(3-Thienylthio)-1-nitrobenzene: To a solution of 4-nitrothiophenol (8%pure; 1.2 g, 6.1 mmol), 3-bromothiophene (1.0 g, 6.1 mmol) and copper(II) oxide (0.5 g, 3.7 mmol) in anhydrous DMF (20 mL) was added KOH (0.3 g, 6.1 mmol), and the resulting mixture was heated at 130° C. with stirring for 42 h and then allowed to cool to room temp. The reaction mixture was then poured into a mixture of ice and a 6N HCl solution (200 mL) and the resulting aqueous mixture was extracted with EtOAc (3×100 mL). The combined organic layers were sequentially washed with a 1M NaOH solution (2×100 mL) and a saturated NaCl solution (2×100 mL), dried (MgSO$_4$), and concentrated in vacuo. The residual oil was purified by MPLC (silica gel; gradient from 10% EtOAc/90% hexane to 5% EtOAc/95% hexane) to afford of the desired product (0.5 g, 34%). GC-MS m/z 237 (M$^+$).

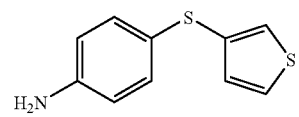

Step 2. 4-(3-Thienylthio)aniline: 4-(3-Thienylthio)-1-nitrobenzene was reduced to the aniline in a manner analogous to that described in Method B1.

A13j. General Method for Substituted Aniline Formation via Nitroarene Formation Through Nucleophilic Aromatic Substitution, Followed by Reduction

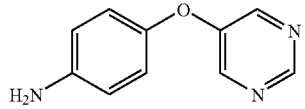

4-(5-Pyrimininyloxy)aniline: 4-Aminophenol (1.0 g, 9.2 mmol) was dissolved in DMF (20 mL) then 5-bromopyrimidine (1.46 g, 9.2 mmol) and $K_2CO_3$ (1.9 g, 13.7 mmol) were added. The mixture was heated to 100° C. for 18 h and at 130° C. for 48 h at which GC-MS analysis indicated some remaining starting material. The reaction mixture was cooled to room temp. and diluted with water (50 mL). The resulting solution was extracted with EtOAc (100 mL). The organic layer was washed with a saturated NaCl solution (2×50 mL), dried (MgSO$_4$), and concentrated in vacuo. The residular solids were purified by MPLC (50% EtOAc/50% hexanes) to give the desired amine (0.650 g, 38%).

A13k. General Method for Substituted Aniline Formation via Nitroarene Formation Through Nucleophilic Aromatic Substitution, Followed by Reduction

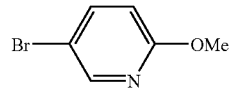

Step 1. 5-Bromo-2-methoxypyridine: A mixture of 2,5-dibromopyridine (5.5 g, 23.2 mmol) and NaOMe (3.76 g, 69.6 mmol) in MeOH (60 mL) was heated at 70° C. in a sealed reaction vessel for 42 h, then allowed to cool to room temp. The reaction mixture was treated with water (50 mL) and extracted with EtOAc (2×100 mL). The combined organic layers were dried (Na$_2$SO$_4$) and concentrated under reduced pressure to give a pale yellow, volatile oil (4.1 g, 95% yield): TLC (10% EtOAc/90% hexane) R$_f$ 0.57.

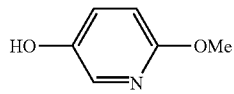

Step 2. 5-Hydroxy-2-methoxypyridine: To a stirred solution of 5-bromo-2-methoxypyridine (8.9 g, 47.9 mmol) in THF (175 mL) at −78° C. was added an n-butyllithium solution (2.5 M in hexane; 28.7 mL, 71.8 mmol) dropwise and the resulting mixture was allowed to stir at −78° C. for 45 min. Trimethyl borate (7.06 mL, 62.2 mmol) was added via syringe and the resulting mixture was stirred for an additional 2 h. The bright orange reaction mixture was warmed to 0° C. and was treated with a mixture of a 3 N NaOH solution (25 mL, 71.77 mmol) and a hydrogen peroxide solution (30%; approx. 50 mL). The resulting yellow and slightly turbid reaction mixture was warmed to room temp. for 30 min and then heated to the reflux temp. for 1 h. The reaction mixture was then allowed to cool to room temp. The aqueous layer was neutralized with a 1N HCl solution then extracted with Et$_2$O (2×100 mL). The combined organic layers were dried (Na$_2$SO$_4$) and concentrated under reduced pressure to give a viscous yellow oil (3.5 g, 60%).

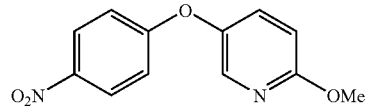

Step 3. 4-(5-(2-Methoxy)pyridyl)oxy-1-nitrobenzene: To a stirred slurry of NaH (97%, 1.0 g, 42 mmol) in anh DMF (100 mL) was added a solution of 5-hydroxy-2-methoxypyridine (3.5 g, 28 mmol) in DMF (100 mL). The resulting mixture was allowed to stir at room temp. for 1 h, 4-fluoronitrobenzene (3 mL, 28 mmol) was added via syringe. The reaction mixture was heated to 95° C. overnight, then treated with water (25 mL) and extracted with EtOAc (2×75 mL). The organic layer was dried (MgSO$_4$) and concentrated under reduced pressure. The residual brown oil was crystalized EtOAc/hexane) to afford yellow crystals (5.23 g, 75%).

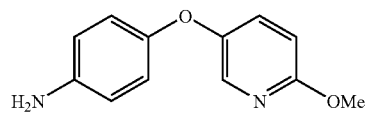

Step 4. 4-(5-(2-Methoxy)pyridyl)oxyaniline: 4-(5-(2-Methoxy)pyridyl)oxy-1-nitrobenzene was reduced to the aniline in a manner analogous to that described in Method B3d, Step 2.

A14a. General Method for Substituted Aniline Synthesis via Nucleophilic Aromatic Substitution using a Halopyridine

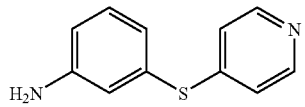

3-(4-Pyridinylthio)aniline: To a solution of 3-aminothiophenol (3.8 mL, 34 mmoles) in anh DMF (90 mL) was added 4-chloropyridine hydrochloride (5.4 g, 35.6 mmoles) followed by K$_2$CO$_3$ (16.7 g, 121 mmoles). The reaction mixture was stirred at room temp. for 1.5 h, then diluted with EtOAc (100 mL) and water (100 mL). The aqueous layer was back-extracted with EtOAc (2×100 mL). The combined organic layers were washed with a saturated NaCl solution (100 mL), dried (MgSO$_4$), and concentrated under reduced pressure. The residue was filtered through a pad of silica (gradient from 50% EtOAc/50% hexane to 70% EtOAc/30% hexane) and the resulting material was triturated with a Et$_2$O/hexane solution to afford the desired product (4.6 g, 66%): TLC (100% ethyl acetate) R$_f$ 0.29; $^1$H-NMR (DMSO-d$_6$) δ 5.41 (s, 2H), 6.64-6.74 (m, 3H), 7.01 (d, J=4.8, 2H), 7.14 (t, J=7.8 Hz, 1H), 8.32 (d, J=4.8, 2H).

A14b. General Method for Substituted Aniline Synthesis via Nucleophilic Aromatic Substitution using a Halopyridine

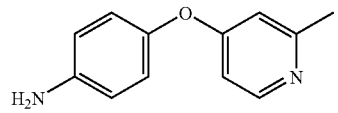

4-(2-Methyl-4-pyridinyloxy)aniline: To a solution of 4-aminophenol (3.6 g, 32.8 mmol) and 4-chloropicoline (5.0 g, 39.3 mmol) in anh DMPU (50 mL) was added potassium tert-butoxide (7.4 g, 65.6 mmol) in one portion. The reaction mixture was heated at 100° C. with stirring for 18 h, then was allowed to cool to room temp. The resulting mixture was poured into water (200 mL) and extracted with EtOAc (3×150 mL). The combined extracts were sequentially washed with water (3×100 mL) and a saturated NaCl solution (2×100 mL), dried (Na$_2$SO$_4$), and concentrated in vacuo. The resulting oil was purified by flash chromatography (50% EtOAc/50% hexane) to afford the desired product as a yellow oil (0.7 g, 9%): CI-MS m/z 201 ((M+H)$^+$).

A14c. General Method for Substituted Aniline Synthesis via Nucleophilic Aromatic Substitution using a Halopyridine

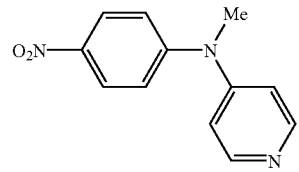

Step 1. Methyl(4-nitrophenyl)-4-pyridylamine: To a suspension of N-methyl-4-nitroaniline (2.0 g, 13.2 mmol) and K$_2$CO$_3$ (7.2 g, 52.2 mmol) in DMPU (30 mL) was added 4-chloropyridine hydrochloride (2.36 g, 15.77 mmol). The reaction mixture was heated at 90° C. for 20 h, then cooled to room temperature. The resulting mixture was diluted with water (100 mL) and extracted with EtOAc (100 mL). The organic layer was washed with water (100 mL), dried (Na$_2$SO$_4$) and concentrated under reduced pressure. The residue was purified by column chromatography (silica gel, gradient from 80% EtOAc/20% hexanes to 100% EtOAc) to afford methyl(4-nitrophenyl)-4-pyridylamine (0.42 g)

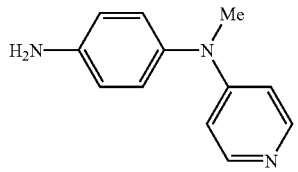

Step 2. Methyl(4-aminophenyl)-4-pyridylamine: Methyl(4-nitrophenyl)-4-pyridylamine was reduced in a manner analogous to that described in Method B1.

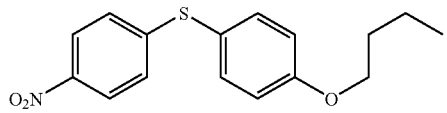

Step 1. 4-(4-Butoxyphenyl)thio-1-nitrobenzene: To a solution of 4-(4-nitrophenyl-thio)phenol (1.50 g, 6.07 mmol) in anh DMF (75 ml) at 0° C. was added NaH (60% in mineral oil, 0.267 g, 6.67 mmol). The brown suspension was stirred at 0° C. until gas evolution stopped (15 min), then a solution of iodobutane (1.12 g, 0.690 ml, 6.07 mmol) in anh DMF (20 mL) was added dropwise over 15 min at 0° C. The reaction was stirred at room temp. for 18 h at which time TLC indicated the presence of unreacted phenol, and additional iodobutane (56 mg, 0.035 mL, 0.303 mmol, 0.5 equiv) and NaH (13 mg, 0.334 mmol) were added. The reaction was stirred an additional 6 h room temp., then was quenched by the addition of water (400 mL). The resulting mixture was extracted with Et$_2$O (2×500 mL). The combined organics were washed with water (2×400 mL), dried (MgSO$_4$), and concentrated under reduced pressure to give a clear yellow oil, which was purified by silica gel chromatography (gradient from 20% EtOAc/80% hexane to 50% EtOAc/50% hexane) to give the product as a yellow solid (1.24 g, 67%): TLC (20% EtOAc/80% hexane) R$_f$ 0.75; $^1$H-NMR (DMSO-d$_6$) δ 0.92 (t, J=7.5 Hz, 3H), 1.42 (app hex, J=7.5 Hz, 2H), 1.70 (m, 2H), 4.01 (t, J=6.6 Hz, 2H), 7.08 (d, J=8.7 Hz, 2H), 7.17 (d, J=9 Hz, 2H), 7.51 (d, J=8.7 Hz, 2H), 8.09 (d, J=9 Hz, 2H).

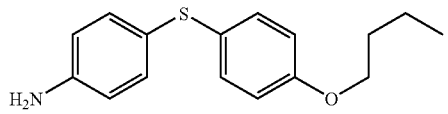

Step 2. 4-(4-Butoxyphenyl)thioaniline: 4-(4-Butoxyphenyl)thio-1-nitrobenzene was reduced to the aniline in a manner analagous to that used in the preparation of 3-(trifluoromethyl)-4-(4-pyridinylthio)aniline (Method B3b, Step 2): TLC (33% EtOAc/77% hexane) R$_f$ 0.38.

A16. General Method for Synthesis of Substituted Anilines by the Acylation of Diaminoarenes

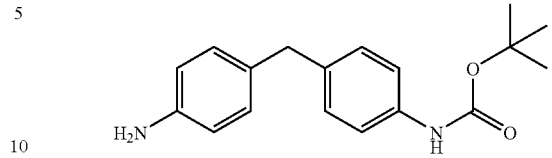

4-(4-tert-Butoxycarbamoylbenzyl)aniline: To a solution of 4,4'-methylenedianiline (3.00 g, 15.1 mmol) in anh THF (50 mL) at room temp was added a solution of di-tert-butyl dicarbonate (3.30 g, 15.1 mmol) in anh THF (10 mL). The reaction mixture was heated at the reflux temp. for 3 h, at which time TLC indicated the presence of unreacted methylenedianiline. Additional di-tert-butyl dicarbonate (0.664 g, 3.03 mmol, 0.02 equiv) was added and the reaction stirred at the reflux temp. for 16 h. The resulting mixture was diluted with Et$_2$O (200 mL), sequentially washed with a saturated NaHCO$_3$ solution (100 ml), water (100 mL) and a saturated NaCl solution (50 mL), dried (MgSO$_4$), and concentrated under reduced pressure. The resulting white solid was purified by silica gel chromatography (gradient from 33% EtOAc/67% hexane to 50% EtOAc/50% hexane) to afford the desired product as a white solid (2.09 g, 46%): TLC (50% EtOAc/50% hexane) R$_f$ 0.45; $^1$H-NMR (DMSO-d$_6$) δ 1.43 (s, 9H), 3.63 (s, 2H), 4.85 (br s, 2H), 6.44 (d, J=8.4 Hz, 2H), 6.80 (d, J=8.1 Hz, 2H), 7.00 (d, J=8.4 Hz, 2H), 7.28 (d, J=8.1 Hz, 2H), 9.18 (br s, 1H); FAB-MS m/z 298 (M$^+$).

A17. General Method for the Synthesis of Aryl Amines via Electrophilic Nitration Followed by Reduction

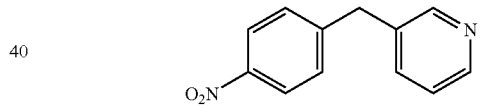

Step 1. 3-(4-Nitrobenzyl)pyridine: A solution of 3-benzylpyridine (4.0 g, 23.6 mmol) and 70% nitric acid (30 mL) was heated overnight at 50° C. The resulting mixture was allowed to cool to room temp. then poured into ice water (350 mL). The aqueous mixture then made basic with a 1N NaOH solution, then extracted with Et$_2$O (4×100 mL). The combined extracts were sequentially washed with water (3×100 mL) and a saturated NaCl solution (2×100 mL), dried (Na$_2$SO$_4$), and concentrated in vacuo. The residual oil was purified by MPLC (silica gel; 50% EtOAc/50% hexane) then recrystallization (EtOAc/hexane) to afford the desired product (1.0 g, 22%): GC-MS m/z 214 (M$^+$).

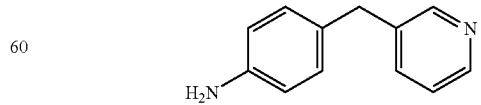

Step 2. 3-(4-Pyridinyl)methylaniline: 3-(4-Nitrobenzyl)pyridine was reduced to the aniline in a manner analogous to that described in Method B1.

A18. General Method for Synthesis of Aryl Amines via Substitution with Nitrobenzyl Halides Followed by Reduction

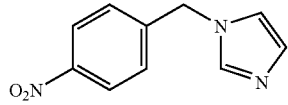

Step 1. 4-(1-Imidazolylmethyl)-1-nitrobenzene: To a solution of imidazole (0.5 g, 7.3 mmol) and 4-nitrobenzyl bromide (1.6 g, 7.3 mmol) in anh acetonitrile (30 mL) was added $K_2CO_3$ (1.0 g, 7.3 mmol). The resulting mixture was stirred at room temp. for 18 h and then poured into water (200 mL) and the resulting aqueous solution was extracted with EtOAc (3×50 mL). The combined organic layers were sequentially washed with water (3×50 mL) and a saturated NaCl solution (2×50 mL), dried ($MgSO_4$), and concentrated in vacuo. The residual oil was purified by MPLC (silica gel; 25% EtOAc/ 75% hexane) to afford the desired product (1.0 g, 91%): EI-MS m/z 203 ($M^+$).

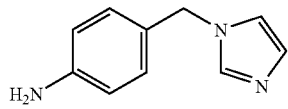

Step 2. 4-(1-Imidazolylmethyl)aniline: 4-(1-Imidazolylmethyl)-1-nitrobenzene was reduced to the aniline in a manner analogous to that described in Method B2.

A19. Formation of Substituted Hydroxymethylanilines by Oxidation of Nitrobenzyl Compounds Followed by Reduction

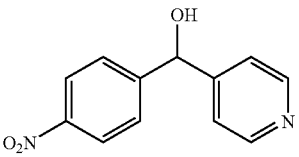

Step 1. 4-(1-Hydroxy-1-(4-pyridyl)methyl-1-nitrobenzene: To a stirred solution of 3-(4-nitrobenzyl)pyridine (6.0 g, 28 mmol) in $CH_2Cl_2$ (90 mL) was added m-CPBA (5.80 g, 33.6 mmol) at 10° C., and the mixture was stirred at room temp. overnight. The reaction mixture was successively washed with a 10% $NaHSO_3$ solution (50 mL), a saturated $K_2CO_3$ solution (50 mL) and a saturated NaCl solution (50 mL), dried ($MgSO_4$) and concentrated under reduced pressure. The resulting yellow solid (2.68 g) was dissolved in anh acetic anhydride (30 mL) and heated at the reflux temperature overnight. The mixture was concentrated under reduced pressure. The residue was dissolved in MeOH (25 mL) and treated with a 20% aqueous $NH_3$ solution (30 mL). The mixture was stirred at room temp. for 1 h, then was concentrated under reduced pressure. The residue was poured into a mixture of water (50 mL) and $CH_2Cl_2$ (50 mL). The organic layer was dried ($MgSO_4$), concentrated under reduced pressure, and purified by column chromatography (80% EtOAc/20% hexane) to afford the desired product as a white solid. (0.53 g, 8%): mp 110-118° C.; TLC (80% EtOAc/20% hexane) $R_f$ 0.12; FAB-MS m/z 367 ($(M+H)^+$, 100%).

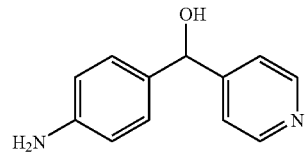

Step 2. 4-(1-Hydroxy-1-(4-pyridyl)methylaniline: 4-(1-Hydroxy-1-(4-pyridinyl)-methyl-1-nitrobenzene was reduced to the aniline in a manner analogous to that described in Method B3d, Step 2.

A20. Formation of 2-(N-methylcarbamoyl)pyridines via the Menisci reaction

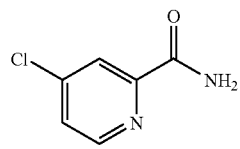

Step 1. 2-(N-methylcarbamoyl)-4-chloropyridine. (Caution: this is a highly hazardous, potentially explosive reaction.) To a solution of 4-chloropyridine (10.0 g) in N-methylformamide (250 mL) under argon at ambient temp was added conc. $H_2SO_4$ (3.55 mL) (exotherm). To this was added $H_2O_2$ (17 mL, 30% wt in H2O) followed by $FeSO_4^-7H2$) (0.55 g) to produce an exotherm. The reaction was stirred in the dark at ambient temp for 1 h then was heated slowly over 4 h at 45° C. When bubbling subsided, the reaction was heated at 60° C. for 16 h. The opaque brown solution was diluted with H2O (700 mL) followed by a 10% NaOH solution (250 mL). The aqueous mixture was extracted with EtOAc (3×500 mL) and the organic layers were washed separately with a saturated NaCl solution (3×50 mlL. The combined organics were dried ($MgSO_4$) and filtered through a pad of silica gel eluting with EtOAc. The solvent was removed in vacuo and the brown residue was purified by silica gel chromatography (gradient from 50% EtOAc/50% hexane to 80% EtOAc/20% hexane). The resulting yellow oil crystallized at 0° C. over 72 h to give 2-(N-methylcarbamoyl)-4-chloropyridine in yield (0.61 g, 5.3%): TLC (50% EtOAc/50% hexane) $R_f$ 0.50; MS; $^1H$ NMR ($CDCl_3$): d 8.44 (d, 1H, J=5.1 Hz, CHN), 8.21 (s, 1H, CHCCO), 7.96 (b s, 1H, NH), 7.43 (dd, 1H, J=2.4, 5.4 Hz, ClCHCN), 3.04 (d, 3H, J=5.1 Hz, methyl); CI-MS m/z 171 ($(M+H)+$).

A21. General Method for the Synthesis of ω-Sulfonylphenyl Anilines

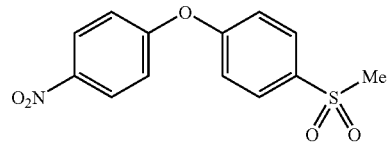

Step 1. 4-(4-Methylsulfonylphenoxy)-1-nitrobenzene: To a solution of 4-(4-methylthiophenoxy)-1-nitrobenzene (2 g, 7.66 mmol) in $CH_2Cl_2$ (75 mL) at 0° C. was slowly added mCPBA (57-86%, 4 g), and the reaction mixture was stirred at room temperature for 5 h. The reaction mixture was treated with a 1 N NaOH solution (25 mL). The organic layer was sequentially washed with a 1N NaOH solution (25 mL), water (25 mL) and a saturated NaCl solution (25 mL), dried (MgSO$_4$), and concentrated under reduced pressure to give 4-(4-methylsulfonylphenoxy)-1-nitrobenzene as a solid (2.1 g).

Step 2. 4-(4-Methylsulfonylphenoxy)-1-aniline: 4-(4-Methylsulfonylphenoxy)-1-nitrobenzene was reduced to the aniline in a manner anaologous to that described in Method B3d, step 2.

A22. General Method for Synthesis of ω-Alkoxy-ω-carboxyphenyl Anilines

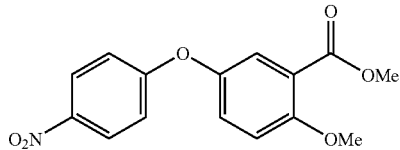

Step 1. 4-(3-Methoxycarbonyl-4-methoxyphenoxy)-1-nitrobenzene: To a solution of (prepared in a manner analogous to that described in Method B3a, step 1, 12 mmol) in acetone (50 mL) was added K$_2$CO$_3$ (5 g) and dimethyl sulfate (3.5 mL). The resulting mixture was heated aaaaaat the reflux tempoerature overnight, then cooled to room temperature and filtered through a pad of Celite®. The resulting solution was concentrated under reduced pressure, absorbed onto silica gel, and purified by column chromatography (50% EtOAc/50% hexane) to give 4-(3-methoxycarbonyl-4-methoxyphenoxy)-1-nitrobenzene as a yellow powder (3 g): mp 115 118° C.

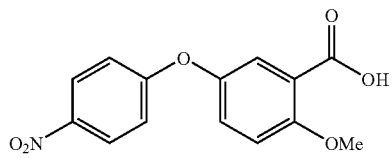

Step 2. 4-(3-Carboxy-4-methoxyphenoxy)-1-nitrobenzene: A mixture of 4-(3-methoxycarbonyl-4-methoxyphenoxy)-1-nitrobenzene (1.2 g), KOH (0.33 g), and water (5 mL) in MeOH (45 mL) was stirred at room temperature overnight and then heated at the reflux temperature for 4 h. The resulting mixture was cooled to room temperature and concentrated under reduced pressure. The residue was dissolved in water (50 mL), and the aqueous mixture was made acidic with a 1N HCl solution. The resulting mixture was extracted with EtOAc (50 mL). The organic layer was dried (MgSO$_4$) and concentrated under reduced pressure to give 4-(3-carboxy-4-methoxyphenoxy)-1-nitrobenzene (1.04 g).

B. General Methods for Urea Formation

B1a. General Method for the Reaction of an Aryl Amine with an Aryl Isocyanate

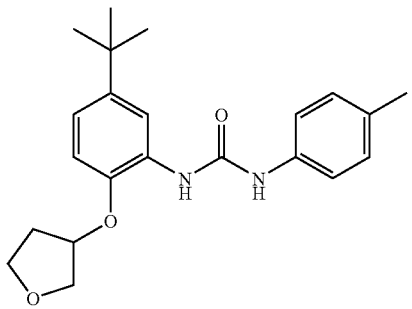

N-(5-tert-Butyl-2-(3-tetrahydrofuranyloxy)phenyl)-N'-(4-methylphenyl)urea: To a solution of 5-tert-butyl-2-(3-tetrahydrofuranyloxy)aniline (0.078 g, 0.33 mmol) in toluene (2.0 mL) was added p-tolyl isocyanate (0.048 g, 0.36 mmol) and the resulting mixture was allowed to stir at room temp. for 8 h to produce a precipitate. The reaction mixture was filtered and the residue was sequentially washed with toluene and hexanes to give the desired urea as a white solid (0.091 g, 75%): mp 229-231° C.; $^1$H-NMR (DMSO-d$_6$) δ 1.30 (s, 9H), 1.99-2.03 (m, 1H), 2.19-2.23 (m, 4H), 3.69-3.76 (m, 1H), 3.86-3.93 (m, 3H), 4.98-5.01 (m, 1H), 6.81-6.90 (m, 2H), 7.06 (d, J=8.09 Hz, 2H), 7.32 (d, J=8.09 Hz, 2H), 7.84 (s, 1H), 8.22 (d, J=2.21 Hz, 1H), 9.26 (s, 1H).

B1b. General Method for the Reaction of an Aryl Amine with an Aryl Isocyanate

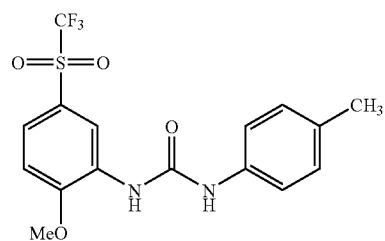

N-(2-Methoxy-5-(trifluoromethanesulfonyl)phenyl)-N'(4-methylphenyl)urea: p-Tolyl isocyanate (0.19 mL, 1.55 mmol) was added to a solution of 2-methoxy-5-(trifluoromethanesulfonyl)aniline (0.330 g, 1.29 mmol) in EtOAc (5 mL), and the reaction mixture was stirred at room temp. for 18 h. The resulting precipitate was collected by filtration and washed with Et$_2$O to give a white solid (0.28 g). This material was then purified by HPLC (C-18 column, 50% CH$_3$CN/50% H$_2$O) and the resulting solids were triturated with Et$_2$O to provide the title compound (0.198 g): $^1$H-NMR (CDCl$_3$) δ 7.08 (d, J=8.5 Hz, 2H), 7.33 (d, J=8.5 Hz, 2H), 7.40 (d, J=8.8 Hz, 1H), 7.71 (dd, J=2.6, 8.8 Hz, 1H), 8.66 (s, 1H), 8.90 (d, J=2.6 Hz, 1H), 9.36 (s, 1H); FAB-MS m/z 389 ((M+1)$^+$).

B1c. General Method for the Reaction of an Aryl Amine with an Aryl Isocyanate

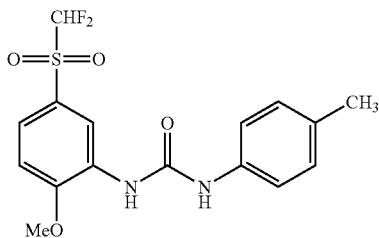

N-(2-Methoxy-5-(difluoromethanesulfonyl)phenyl)-N'-(4-methylphenyl)urea: p-Tolyl isocyanate (0.058 mL, 0.46 mmol) was added to a solution of 2-methoxy-5-(difluoromethanesulfonyl)aniline (0.100 g, 0.42 mmol) in EtOAc (0.5 mL) and the reaction mixture was stirred at room temp. for 3 d. The resulting precipitate was filtered and washed with $Et_2O$ to provide the title compound as a white solid (0.092 g): $^1$H-NMR (CDCl$_3$) δ 2.22 (s, 3H), 4.01 (s, 3H), 7.01-7.36 (m, 6H), 7.54 (dd, J=2.4, 8.6 Hz, 1H), 8.57 (s, 1H), 8.79 (d, J=2.6 Hz, 1H), 9.33 (s, 1H); EI-MS m/z 370 (M$^+$).

B1d. General Method for the Reaction of an Aryl Amine with an Aryl Isocyanate

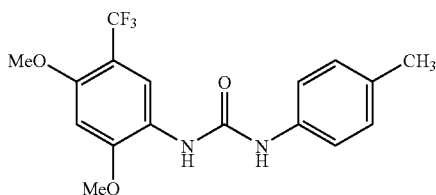

N-(2,4-Dimethoxy-5-(trifluoromethyl)phenyl)-N'-(4-methylphenyl)urea: p-Tolyl isocyanate (0.16 mL, 1.24 mmol) was added to a solution of 2,4-dimethoxy-5-(trifluoromethyl)aniline (0.25 g, 1.13 mmol) in EtOAc (3 mL) and the resulting mixture was stirred at room temp. for 18 h. The resulting precipitate was washed with $Et_2O$ to give the title compound as a white solid (0.36 g): $^1$H-NMR (CDCl$_3$) δ 2.21 (s, 3H), 3.97 (s, 3H), 3.86 (s, 3H), 6.88 (s, 1H), 7.05 (d, J=8.5 Hz, 2H), 7.29 (d, J=8.5 Hz, 2H), 8.13 (s, 1H), 8.33 (s, 1H), 9.09 (s, 1H); FAB-MS m/z 355 ((M+1)$^+$).

B1e. General Method for the Reaction of an Aryl Amine with an Aryl Isocyanate

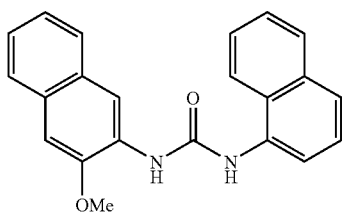

N-(3-Methoxy-2-naphthyl)-N'-(1-naphthyl)urea: To a solution of 2-amino-3-methoxynaphthalene (0.253 g, 1.50 mmol) in $CH_2Cl_2$ (3 mL) at room temp. was added a solution of 1-naphthyl isocyanate (0.247 g, 1.50 mmol) in $CH_2Cl_2$ (2 mL) and the resulting mixture was allowed to stir overnight. The resulting precipitate was separated and washed with $CH_2Cl_2$ to give the desired urea as a white powder (0.450 g, 90%): mp 235-236° C.; $^1$H-NMR (DMSO-d$_6$) δ 4.04 (s, 3H), 7.28-7.32 (m, 2H), 7.38 (s, 1H), 7.44-7.72 (m, 6H), 7.90-7.93 (m, 1H), 8.05-8.08 (m, 1H), 8.21-8.24 (m, 1H), 8.64 (s, 1H), 9.03 (s, 1H), 9.44 (s, 1H); FAB-MS m/z 343 ((M+H)$^+$).

B1f. General Method for the Reaction of an Aryl Amine with an Aryl Isocyanate

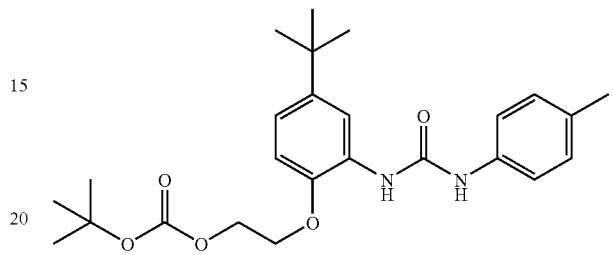

N-(5-tert-Butyl-2-(2-tert-butoxycarbonyloxy)ethoxy)phenyl)-N'-(4-methylphenyl)urea: A mixture of 5-tert-butyl-2-(2-tert-butoxycarbonyloxy)ethoxy)aniline (Method A10, 0.232 g, 0.75 mmol) and p-tolyl isocyanate (0.099 mL, 0.79 mmol) in EtOAc (1 mL) was stirred at room temp. for 3 d to produce a solid, which was separated. The filtrate was purified by column chromatography (100% $CH_2Cl_2$) and the residue was triturated ($Et_2O$/hexane) to give the desired product (0.262 g, 79%); mp 155-156° C.; TLC (20% EtOAc/80% hexane) R$_f$ 0.49; $^1$H-NMR (DMSO-d$_6$) δ 1.22 (s, 9H), 1.37 (s, 9H), 2.21 (s, 3H), 4.22-4.23 (m, 2H), 4.33-4.35 (m, 2H), 6.89-7.00 (m, 4H), 7.06 (d, J=8.5 Hz, 2H), 7.32 (d, J=8.1 Hz, 2H), 7.96 (s, 1H); 8.22 (d, J=1.5 Hz, 1H), 9.22 (s, 1H); FAB-MS m/z (rel abundance) 443 ((M+H)$^+$, 6%).

B2a. General Method for Reaction of an Aryl Amine with Phosgene Followed by Addition of a Second Aryl Amine

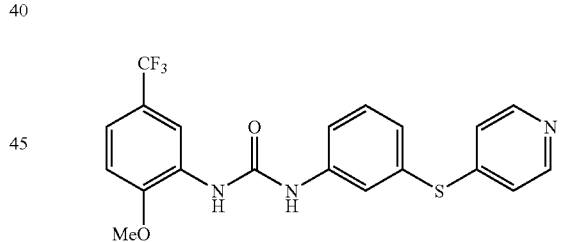

N-(2-Methoxy-5-(trifluoromethyl)phenyl)-N'-(3-(4-pyridinylthio)phenyl)urea: To a solution of pyridine (0.61 mL, 7.5 mmol, 3.0 equiv) and phosgene (20% in toluene; 2.65 mL, 5.0 mmol, 2.0 equiv) in $CH_2Cl_2$ (20 mL) was added 2-methoxy-5-(trifluoromethyl)aniline (0.48 g, 2.5 mmol) at 0° C. The resulting mixture was allowed warm to room temp. stirred for 3 h, then treated with anh. toluene (100 mL) and concentrated under reduced pressure. The residue was suspended in a mixture of $CH_2Cl_2$ (10 mL) and anh. pyridine (10 mL) and treated with 3-(4-pyridinylthio)aniline (0.61 g, 2.5 mmol, 1.0 equiv). The mixture was stirred overnight at room temp., then poured into water (50 mL) and extracted with $CH_2Cl_2$ (3×25 mL). The combined organic layers were dried (MgSO$_4$) and concentrated under reduced pressure. The residue was dissolved in a minimal amount of $CH_2Cl_2$ and treated with pet. ether to give the desired product as a white precipitate (0.74 g, 70%): mp 202° C.; TLC (5% acetone/95% $CH_2Cl_2$) R$_f$ 0.09;

¹H-NMR (DMSO-d₆) δ 7.06 (d, J=5.5 Hz, 2H), 7.18 (dd, J=2.4, 4.6 Hz, 2H), 7.31 (dd, J=2.2, 9.2 Hz, 1H), 7.44 (d, J=5.7 Hz, 1H), 7.45 (s, 1H), 7.79 (d, J=2.2 Hz, 1H), 8.37 (s, 2H), 8.50 (dd, J=2.2, 9.2 Hz, 2H), 9.63 (s, 1H), 9.84 (s, 1H); FAB-MS m/z 420 ((M+H)⁺, 70%).

B2b. General Method for Reaction of an Aryl Amine with Phosgene Followed by Addition of a Second Aryl Amine

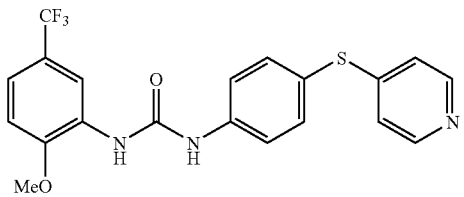

N-(2-Methoxy-5-(trifluoromethyl)phenyl)-N'-(4-(4-pyridinylthio)phenyl)urea: To a solution of pyridine (0.61 mL, 7.5 mmol, 3.0 equiv) and phosgene (20% in toluene; 2.65 mL, 5.0 mmol, 2.0 equiv) in CH₂Cl₂ (20 mL) was added 4-(4-pyridinylthio)aniline (0.506 g, 2.5 mmol) at 0° C. After stirring for 3 h at room temp., the mixture was treated with anh. toluene (100 mL) then concentrated under reduced pressure. The residue was suspended in a mixture of CH₂Cl₂ (10 mL) and anh. pyridine (10 mL) and treated with 2-methoxy-5-(trifluoromethyl)aniline (0.50 g, 2.5 mmol, 1.0 equiv). After stirring the mixture overnight at room temp., it was poured into a 1 N NaOH solution (50 mL) and extracted with CH₂Cl₂ (3×25 mL). The combined organic layers were dried (MgSO₄) and concentrated under reduced pressure to give the desired urea (0.74 g, 71%): mp 215° C.; TLC (5% acetone/95% CH₂Cl₂) R_f 0.08; ¹H-NMR (DMSO-d₆) δ 3.96 (s, 3H), 6.94 (dd, J=1.1, 4.8 Hz, 2H), 7.19 (d, J=8.4 Hz, 1H), 7.32 (dd, J=2.2, 9.3 Hz, 1H), 7.50 (d, J=8.8 Hz, 2H), 7.62 (d, J=8.8 Hz, 2H), 8.32 (d, J=5.1 Hz, 2H), 8.53 (d, J=0.7 Hz, 1H), 8.58 (s, 1H), 9.70 (s, 1H); FAB-MS m/z 420 ((M+H)⁺).

B3a. General Method for Reaction of an Aryl Amine with Phosgene with Isolation of the Isocyanate, Followed by Reaction with a Second Aryl Amine

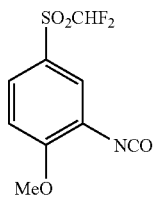

Step 1. 5-(Difluoromethanesulfonyl)-2-methoxyphenyl isocyanate: To a solution of phosgene (1.95 M in toluene; 3.0 mL, 5.9 mmol) in CH₂Cl₂ (40 mL) at 0° C. was added a solution of 5-(difluoromethanesulfonyl)-2-methoxyaniline (0.70 g, 2.95 mmol) and pyridine (0.44 mL, 8.85 mmol) in CH₂Cl₂ (10 mL) dropwise. After being stirred at 0° C. for 30 min and at room temp. for 3 h, the reaction mixture was concentrated under reduced pressure, then treated with toluene (50 mL). The resulting mixture was concentrated under reduced pressure, then was treated with Et₂O (50 mL) to produce a precipitate (pyridinium hydrochloride). The resulting filtrate was concentrated under reduced pressure to provide the title compound as a white solid (0.33 g). This material was used in the next step without further purification.

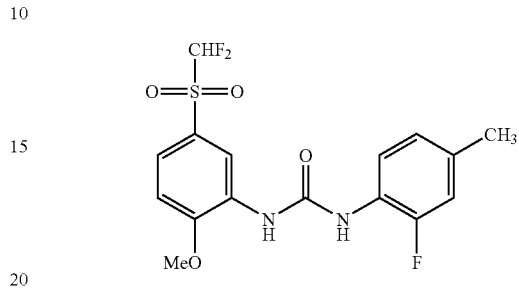

Step 2. N-(2-Methoxy-5-(difluoromethanesulfonyl)phenyl)-N'-(2-fluoro-4-methylphenyl)urea: 2-Fluoro-4-methylaniline (0.022 mL, 0.19 mmol) was added to a solution of 5-(difluoromethanesulfonyl)-2-methoxyphenyl isocyanate (0.046 g, 0.17 mmol) in EtOAc (1 mL). The reaction mixture was stirred at room temp. for 3 d. The resulting precipitate was washed with Et₂O to provide the title compound as a white solid (0.055 g); ¹H-NMR (CDCl₃) δ 2.24 (s, 3H), 4.01 (s, 3H), 6.93 (d, J=8.5 Hz, 1H), 7.01-7.36 (m, 3H), 7.56 (dd, J=2.4, 8.6 Hz, 1H), 7.98 (app t, J=8.6 Hz, 1H), 8.79 (d, J=2.2 Hz, 1H), 9.07 (s, 1H), 9.26 (s, 1H); FAB-MS m/z 389 ((M+1)⁺).

B3b. General Method for Reaction of an Aryl Amine with Phosgene with Isolation of the Isocyanate, Followed by Reaction with a Second Aryl Amine

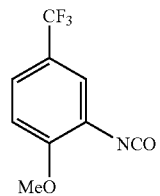

Step 1. 2-Methoxy-5-trifluoromethylphenyl Isocyanate: To a solution of phosgene (1.93 M in toluene; 16 mL, 31.4 mmol) in CH₂Cl₂ (120 mL) at 0° C. was added a solution of 2-methoxy-5-(trifluoromethyl)aniline (3.0 g, 15.7 mmol) and pyridine (2.3 mL, 47.1 mmol) in CH₂Cl₂ (30 mL) dropwise. The resulting mixture was stirred at 0° C. for 30 min and at room temp. for 3 h, the concentrated under reduced pressure. The residue was diluted with toluene (30 mL), concentrated under reduced pressure, and treated with Et₂O. The resulting precipitate (pyridinium hydrochloride) was removed and the filtrate was concentrated under redeuced pressure to give the title compound as a yellow oil (3.0 g) which crystallized upon standing at room temp. for a few days.

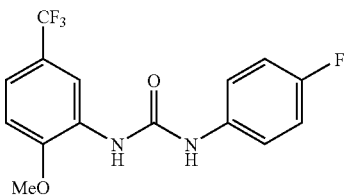

Step 2. N-(2-Methoxy-5-(trifluoromethyl)phenyl)-N'-(4-fluorophenyl)urea: 4-Fluoroaniline (0.24 mL, 2.53 mmol) was added to a solution of 2-methoxy-5-(trifluoromethyl) phenyl isocyanate (0.50 g, 2.30 mmol) in EtOAc (6 mL) and the reaction mixture was stirred at room temp. for 3 d. The resulting precipitate was washed with $Et_2O$ to give the title compound as a white solid (0.60 g): NMR: 3.94 (s, 3H), 7.13-7.18 (m, 3H), 7.30 (dd, J=1.5, 8.4 Hz, 1H), 7.44 (m, 2H), 8.45 (s, 1H), 8.52 (d, J=2.2 Hz, 1H), 9.42 (s, 1H); FAB-MS m/z 329 ((M+1)$^+$).

B4. General Method for Urea Formation via Curtius Rearrangement, Followed by Trapping with an Amine

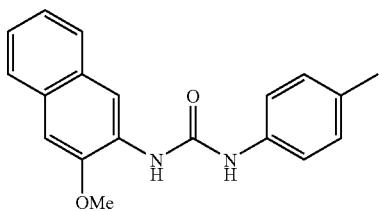

N-(3-Methoxy-2-naphthyl)-N'-(4-methylphenyl)urea: To a solution of 3-methoxy-2-naphthoic acid (Method A6, Step 2; 0.762 g, 3.80 mmol) and $Et_3N$ (0.588 mL, 4.2 mmol) in anh toluene (20 mL) at room temp. was added a solution of diphenylphosphoryl azide (1.16 g, 4.2 mmol) in toluene (5 mL). The resulting mixture was heated to 80° C. for 2 h, cooled to room temp., and p-toluidine (0.455 g, 4.1 mmol) was added. The mixture was heated at 80° C. overnight, cooled to room temp., quenched with a 10% citric acid solution, and extracted with EtOAc (2×25 mL). The combined organic layers were washed with a saturated NaCl solution (25 mL), dried ($MgSO_4$), and concentrated in vacuo. The residue was triturated with $CH_2Cl_2$ to give the desired urea as white powder (0.700 g, 61%): mp 171-172° C; $^1$H-NMR (DMSO-$d_6$) δ 2.22 (s, 3H), 3.99 (s, 3H), 7.07 (d, J=8.49 Hz, 2H), 7.27-7.36 (m, 5H), 7.67-7.72 (m, 2H), 8.43 (s, 1H), 8.57 (s, 1H), 9.33 (s, 1H); FAB-MS m/z 307 ((M+H)$^+$).

B5. General Method for the Reaction of Substituted Aniline with N,N'-Carbonyldiimidazole Followed by Reaction with a Second Amine

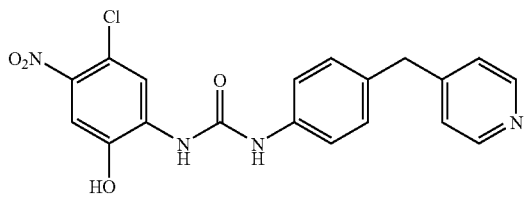

N-(5-Chloro-2-hydroxy-4-nitrophenyl)-N'-(4-(4-pyridinylmethyl)phenyl)urea: A solution of 4-(4-pyridinylmethyl) aniline (0.300 g, 1.63 mmol) and N,N'-carbonyldiimidazole (0.268 g, 1.65 mmol) in $CH_2Cl_2$ (10 mL) was stirred at room temp. for 1 h at which time TLC analysis indicated no starting aniline. The reaction mixture was then treated with 2-amino-4-chloro-5-nitrophenol (0.318 g, 1.65 mmol) and stirred a 40-45° C. for 48 h. The resulting mixture was cooled to room temp. and diluted with EtOAc (25 mL). The resulting precipitate was separated to give the desired product (0.416 g, 64%): TLC (50% acetone/50% $CH_2Cl_2$) $R_f$ 0.40; $^1$H-NMR (DMSO-$d_6$) δ 3.90 (s, 2H), 7.18 (d, J=8.4 Hz, 2H), 7.21 (d, J=6 Hz, 2H), 7.38 (d, J=8.4 Hz, 2H), 7.54 (s, 1H), 8.43-8.45 (m, 3H), 8.78 (s, 1H), 9.56 (s, 1H), 11.8 (br s, 1H); FAB-MS m/z (rel abundance) 399 ((M+H)$^+$, 10%).

B6. General Method for the Synthesis of Symmetrical Diphenyl Ureas as Side-Products of Urea Forming Reactions

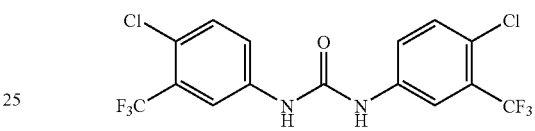

Bis(4-chloro-3-(trifluoromethyl)phenyl)urea: To a solution of 5-amino-3-tert-butylisoxazole (0.100 g) in anh toluene (5 mL) was added 4-chloro-3-(trifluoromethyl)phenyl isocyanate (0.395 g). The reaction vessel was sealed, heated at 85° C. for 24 h, and cooled to room temp. The reaction mixture was added to a slurry of Dowex® 50WX2-100 resin (0.5 g) in $CH_2Cl_2$ (40 mL), and the resulting mixture was stirred vigorously for 72 h. The mixture was filtered and the filtrate was concentrated under reduced pressure. The residue was purified by column chromatography (gradient form 100% $CH_2Cl_2$ to 5% MeOH/95% $CH_2Cl_2$) to give bis(4-chloro-3-(trifluoromethyl)phenyl)urea followed by N-(3-tert-butyl-5-isoxazolyl)-N'-(4-chloro-3-(trifluoromethyl)phenyl)urea.

The residue from the symmetrical urea fractions was triturated ($Et_2O$/hexane) to give the urea as a white solid (0.110 g): TLC (3% MeOH/97% $CH_2Cl_2$) $R_f$ 0.55; FAB-MS m/z 417 ((M+H)$^+$).

C. Urea Interconversions and Misc. Reactions

C1. General Method for Alkylation of Hydroxyphenyl Ureas

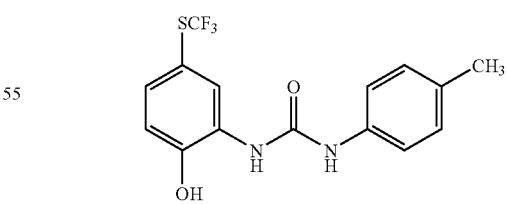

Step 1. N-(2-Hydroxy-5-(trifluoromethylthio)phenyl)-N'-(4-methylphenyl)urea: p-Tolyl isocyanate (0.066 mL, 0.52 mmol) was added to a solution of 2-hydroxy-5-(trifluoromethylthio)aniline (0.100 g, 0.48 mmol) in EtOAc (2 mL) and the reaction mixture was stirred at room temp. for 2 d. The resulting precipitate was washed with EtOAc to provide the title compound (0.13 g): ¹H-NMR (CDCl₃) δ 2.24 (s, 3H), 7.44-7.03 (m, 6H), 8.46 (s, 1H), 8.60 (d, J=1.8 Hz, 1H), 9.16 (s, 1H), 10.41 (s, 1H); FAB-MS m/z 343 ((M+1)⁺). This material was used in the next step without purification.

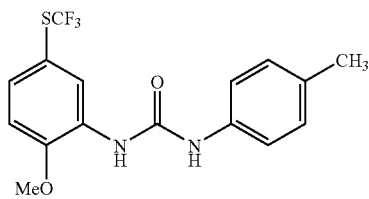

Step 2. N-(2-Methoxy-5-(trifluoromethylthio)phenyl)-N'-(4-methylphenyl)urea: A solution of N-(2-hydroxy-5-(trifluoromethylthio)phenyl)-N'-(4-methylphenyl)urea (0.125 g, 0.36 mmol), iodomethane (0.045 mL, 0.73 mmol), and K₂CO₃ (100 mg, 0.73 mmol) in acetone (2 mL) was heated at the reflux temp. for 6 h, then was cooled to room temp. and concentrated under reduced pressure. The residue was dissolved in a minimal amount of MeOH, absorbed onto silica gel, and then purified by flash chromatography (3% Et₂O/97% CH₂Cl₂) to provide the title compound as a white solid (68 mg): ¹H-NMR (CDCl₃) δ 2.22 (s, 3H), 3.92 (s, 3H), 7.05-7.32 (m, 6H), 8.37 (s, 1H), 8.52 (d, J=2.2 Hz, 1H), 9.27 (s, 1H); FAB-MS m/z 357 ((M+1)⁺).

C2. General Method for the Reduction of Nitro-Containing Ureas

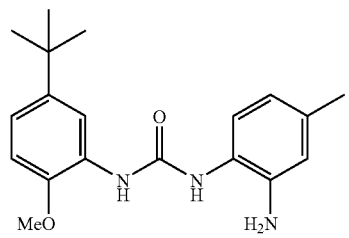

N-(5-tert-Butyl-2-methoxyphenyl)-N'-(2-amino-4-methylphenyl)urea: A solution of N-(5-tert-butyl-2-methoxyphenyl)-N'-(2-nitro-4-methylphenyl)urea (prepared in a manner analogous to Method B1a; 4.0 g, 11.2 mmol) in EtOH (100 mL) was added to a slurry of 10% Pd/C (0.40 g) in EtOH (10 mL), and the resulting mixture was stirred under an atmosphere of H₂ (balloon) at room temp. for 18 h. The mixture was filtered through a pad of Celite® and concentrated in vacuo to afford the desired product (3.42 g, 94%) as a powder: mp 165-166° C.; ¹H-NMR (DMSO-d₆) δ 1.30 (s, 9H), 2.26 (s, 3H), 3.50 (br s, 2H), 3.71 (s, 3H), 6.39 (br s, 1H), 6.62 (s, 1H), 6.73 (d, J=8.46 Hz, 1H), 6.99 (dd, J=2.21, 8.46 Hz, 1H), 7.05 (d, J=8.46 Hz, 1H), 7.29 (s, 1H), 8.22 (d, J=2.57 Hz, 1H); FAB-MS m/z 328 ((M+H)⁺).

C3. General Method of Thiourea Formation by Reaction with a Thioisocyanate

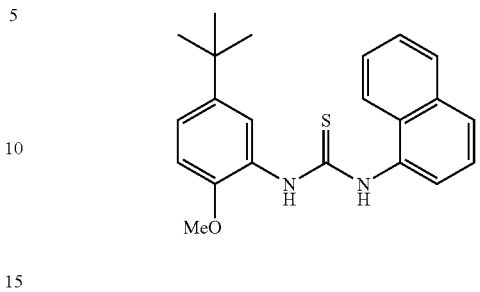

N-(5-tert-Butyl-2-methoxyphenyl)-N'-(1-naphthyl)thiourea: To a solution of 5-tert-butyl-2-methoxyaniline (0.372 g, 2.07 mmol) in toluene (5 mL) was added 1-naphthyl thioisocyanate (0.384 g, 2.07 mmol) and the resulting mixture was allowed to stir at room temp. for 8 h to produce a precipitate. The solids were separated and sequentially washed with toluene and hexane to give the desired product as an off-white pwoder (0.364 g, 48%): mp 158-160° C.; ¹H-NMR (DMSO-d₆) δ 1.31 (s, 9H), 3.59 (s, 3H), 6.74 (d, J=8.46 Hz, 1H), 7.13 (dd, J=2.21, 8.46 Hz, 1H), 7.53-7.62 (m, 4H), 7.88-7.95 (m, 4H), 8.06-8.08 (m, 1H), 8.09 (br s, 1H); FAB-MS m/z 365 ((M+H)⁺).

C4. General Method for Deprotection of tert-Butyl Carbonate-Containing Ureas

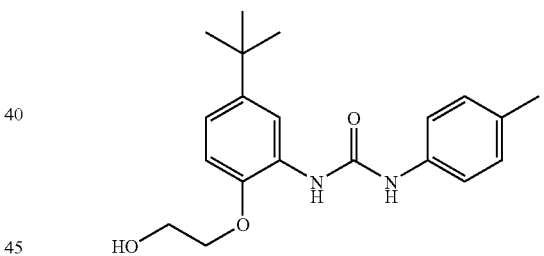

N-(5-tert-Butyl-2-(2-hydroxyethoxy)phenyl)-N'-(4-methylphenyl)urea: A solution of N-(5-tert-butyl-2-(2-tert-butoxycarbonyloxy)ethoxy)phenyl)-N'-(4-methylphenyl)urea (Method B1f; 0.237 g, 0.54 mmol) and TFA (0.21 mL, 2.7 mmol) in CH₂Cl₂ (2 mL) was stirred at room temp for 18 h, then was washed with a saturated NaHCO₃ solution (2 mL). The organic layer was dried by passing through 1PS filter paper (Whatman®) and concentrated under reduced pressure. The resulting white foam was triturated (Et₂O/hexane), then recrystallized (Et₂O) to give the desired product (3.7 mg): TLC (50% EtOAc/50% hexane) R_f 0.62; ¹H-NMR (DMSO-d₆) δ 1.22 (s, 9H), 3.75-3.76 (m, 2H), 4.00-4.03 (m, 2H), 4.80 (t, J=5.0 Hz, 1H), 6.88-6.89 (m, 4H), 7.06 (d, J=8.5 Hz, 2H), 7.33 (d, J=8.1 Hz, 2H), 7.97 (s, 1H), 8.20 brs, 1H), 9.14 (s, 1H); FAB-MS m/z (rel abundance) 343 ((M+H)⁺, 100%).

The following compounds have been synthesized according to the General Methods listed above:

TABLE 1

2-Substituted-5-tert-butylphenyl Ureas

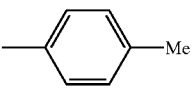

| Example | R¹ | R² | mp (°C.) | TLC $R_f$ | Solvent System | Mass Spec. | Source | Synth. Method |
|---|---|---|---|---|---|---|---|---|
| 1 | OH | 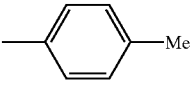 | | 0.54 | 2% MeOH/98% CH2Cl2 | 299 (M + H)+ | FAB | B1d |
| 2 | OMe | 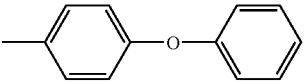 | 199-200 | | | 313 (M + H)+ | FAB | B1d |
| 3 | OMe | 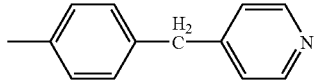 | 208-209 | | | 390 (M+) | EI | B1d |
| 4 | OMe | 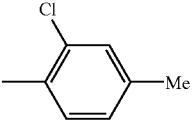 | 192-194 | | | 389 (M + H)+ | FAB | B1d |
| 5 | OMe | 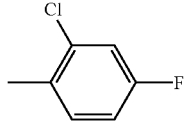 | | 0.58 | 50% EtOAc/50% hexane | 347 (M + H)+ | FAB | B3b |
| 6 | OMe | 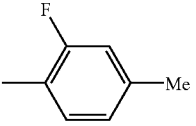 | | 0.62 | 50% EtOAc/50% hexane | 351 (M + H)+ | FAB | B3b |
| 7 | OMe | 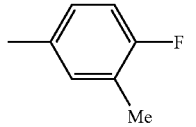 | | 0.71 | 50% EtOAc/50% hexane | 331 (M + H)+ | FAB | B1d |
| 8 | OMe | 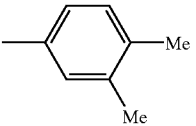 | | 0.74 | 50% EtOAc/50% hexane | 331 (M + H)+ | FAB | B3b |
| 9 | OMe | | | 0.66 | 20% EtOAc/80% hexane | 327 (M + H)+ | FAB | B1d |

TABLE 1-continued

2-Substituted-5-tert-butylphenyl Ureas

| Example | R¹ | R² | mp (° C.) | TLC R$_f$ | Solvent System | Mass Spec. | Source | Synth. Method |
|---|---|---|---|---|---|---|---|---|
| 10 | OMe | 4-Me-3-F-phenyl | | 0.62 | 20% EtOAc/80% hexane | 331 (M + H)+ | FAB | B1d |
| 11 | OMe | 2,4-diF-phenyl | | 0.42 | 13% EtOAc/87% hexane | 335 (M + H)+ | FAB | B1d |
| 12 | OMe | 2,4-diMe-phenyl | | 0.52 | 2% MeOH/98% CH2Cl2 | 327 (M + H)+ | FAB | B1d |
| 13 | OMe | 3,4-diF-phenyl | | 0.56 | 2% MeOH/98% CH2Cl2 | 335 (M + H)+ | FAB | B1d |
| 14 | OMe | 3-Cl-4-F-phenyl | | 0.48 | 2% MeOH/98% CH2Cl2 | 351 (M + H)+ | FAB | B1d |
| 15 | OMe | 3-Cl-4-Me-phenyl | | 0.50 | 2% MeOH/98% CH2Cl2 | 347 (M + H)+ | FAB | B1d |
| 16 | OMe | 4-(pyridin-3-ylmethyl)phenyl | 201-202 | | | 390 (M + H)+ | FAB | B2a |
| 17 | OMe | 4-(pyridin-2-ylmethyl)phenyl | 199-200 | | | 390 (M + H)+ | FAB | B2a |
| 18 | OMe | 4-Et-phenyl | 198-199 | 0.45 | 25% EtOAc/75% hexane | | | B1a |
| 19 | OMe | 4-benzyl-phenyl | 181-182 | | | 389 (M + H)+ | CI | B2a |

TABLE 1-continued

2-Substituted-5-tert-butylphenyl Ureas

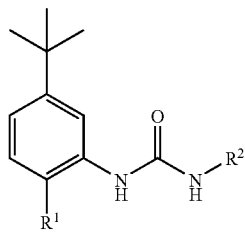

| Example | R¹ | R² | mp (° C.) | TLC R$_f$ | Solvent System | Mass Spec. | Source | Synth. Method |
|---|---|---|---|---|---|---|---|---|
| 20 | OMe | -C$_6$H$_4$-O-C$_6$H$_5$ (4-phenoxyphenyl) | 181-183 | | | 390 (M+) | EI | B1a |
| 21 | OMe | 2-methyl-5-nitro-... (2-Me, 5-NO$_2$ phenyl) | 175-177 | | | 358 (M + H)+ | FAB | B1a |
| 22 | OMe | 4-Me, 3-NO$_2$ phenyl | 219-220 | | | 358 (M + H)+ | FAB | B1a |
| 23 | OMe | 2-Me, 5-NH$_2$ phenyl | 165-166 | | | 328 (M + H)+ | FAB | C2 |
| 24 | OMe | 4-Me, 3-NH$_2$ phenyl | 102-104 | | | 271 (M + H)+ | FAB | C2 |
| 25 | OMe | 1-naphthyl | 236-238 | | | 349 (M + H)+ | FAB | B1a |
| 26 | OMe | 2-Me, 3-Cl, 4-Cl... (2,3-dichloro-6-methylphenyl) | 192-194 | | | 367 (M + H)+ | FAB | B1a |

TABLE 1-continued
2-Substituted-5-tert-butylphenyl Ureas
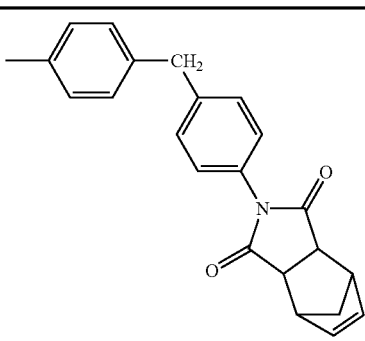
| Example | R¹ | R² | mp (° C.) | TLC R$_f$ | Solvent System | Mass Spec. | Source | Synth. Method |
|---|---|---|---|---|---|---|---|---|
| 27 | OMe | 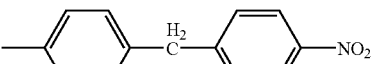 | 137–140 | | | 550 (M + H)+ | FAB | B2a |
| 28 | OMe | 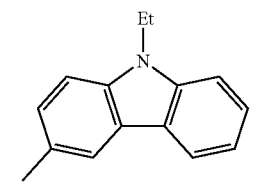 | 197–199 | | | 434 (M + H)+ | CI | A8, B2a |
| 29 | OMe | 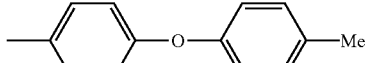 | 212–215 | | | 416 (M + H)+ | FAB | B2a |
| 30 | OMe | 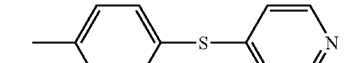 | 195 | | | 405 (M + H)+ | FAB | B1e |
| 31 | OMe | 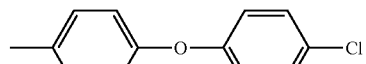 | 110 | 0.07 | 5% acetone/95% CH2Cl2 | 408 (M + H)+ | FAB | B2b |
| 32 | OMe | 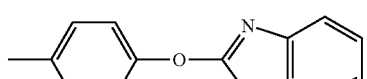 | 185 | 0.67 | 5% acetone/95% CH2Cl2 | 425 (M + H)+ | FAB | B2a |
| 33 | OMe |  | 214–215 | 0.54 | 5% acetone/95% CH2Cl2 | 448 (M + H)+ | FAB | B2a |
| 34 | OMe | 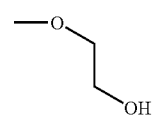 | 180 | 0.56 | 5% acetone/95% CH2Cl2 | 421 (M + H)+ | FAB | B2a |
| 35 | 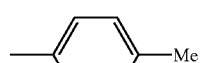 |  | | 0.67 | 50% EtOAc/50% hexane | 343 (M + H)+ | FAB | A10, B1f, C4 |

TABLE 1-continued

2-Substituted-5-tert-butylphenyl Ureas

| Example | R¹ | R² | mp (° C.) | TLC R_f | Solvent System | Mass Spec. | Source | Synth. Method |
|---|---|---|---|---|---|---|---|---|
| 36 | —NH—C(O)Me | —C₆H₄-4-Me | | 0.45 | 50% EtOAc/50% hexane | 340 (M + H)+ | FAB | B1d |
| 37 | —N(Me)—C(O)Me | —C₆H₄-4-Me | 222–223 | | | 354 (M + H)+ | ES | B1c |
| 38 | N-methyl-2-pyrrolidinone | —C₆H₄-4-Me | 203–205 | | | 366 (M + H)+ | FAB | B1d |
| 39 | 1-methyl-imidazolidin-2-one | —C₆H₄-4-Me | 230–232 | | | 367 (M + H)+ | FAB | B1d |
| 40 | —OCH₂C(O)NHMe | 1-naphthyl | 197–198 | | | 406 (M + H)+ | FAB | A9, B1a |
| 41 | —OCH₂C(O)NHMe | 2,4-difluorophenyl | 204–205 | | | 392 (M + H)+ | FAB | A9, B1a |
| 42 | —OCH₂C(O)NHMe | 2,3-dichlorophenyl | 217–218 | | | 424 (M + H)+ | FAB | A9, B1a |
| 43 | —OCH₂C(O)NHMe | —C₆H₄-4-Me | 187–188 | | | 370 (M + H)+ | FAB | A9, B1a |

TABLE 1-continued
2-Substituted-5-tert-butylphenyl Ureas
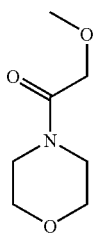
| Example | R¹ | R² | mp (° C.) | TLC R$_f$ | Solvent System | Mass Spec. | Source | Synth. Method |
|---|---|---|---|---|---|---|---|---|
| 44 | 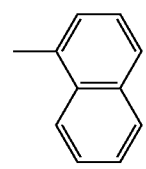 | 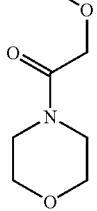 | 118–120 | | | 462 (M + H)+ | FAB | A9, B1a |
| 45 | 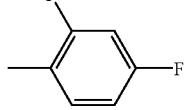 | 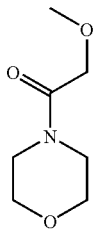 | 146–148 | | | 448 (M + H)+ | FAB | A9, B1a |
| 46 | 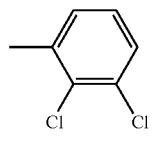 | 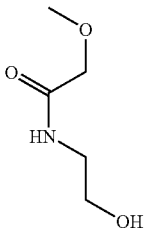 | 110–113 | | | 480 (M + H)+ | FAB | A9, B1a |
| 47 | 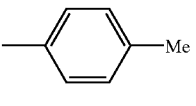 | 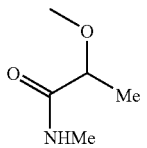 | 95-100 | | | 400 (M + H)+ | FAB | A9, B1a |
| 48 | 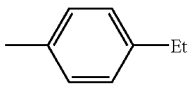 | 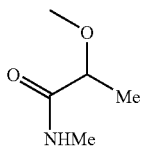 | 107–110 | | | 398 (M + H)+ | FAB | A9, B1a |
| 49 | 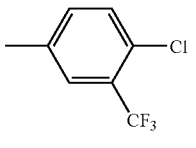 | | 180–182 | | | 472 (M + H)+ | FAB | A9, B1a |

TABLE 1-continued
2-Substituted-5-tert-butylphenyl Ureas
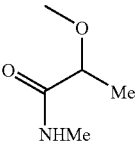
| Example | R¹ | R² | mp (° C.) | TLC R_f | Solvent System | Mass Spec. | Source | Synth. Method |
|---|---|---|---|---|---|---|---|---|
| 50 |  | 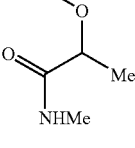 | 217–219 | | | 388 (M + H)+ | FAB | A9, R1a |
| 51 | 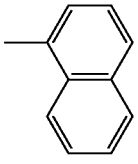 | 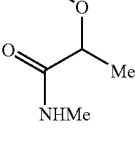 | 116–120 | | | 420 (M + H)+ | FAB | A9, B1a |
| 52 | 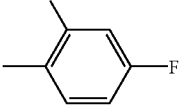 | 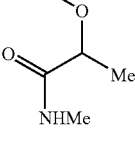 | 100–105 | | | 406 (M + H)+ | FAB | A9, B1a |
| 53 | 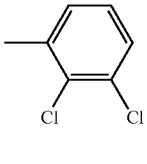 | 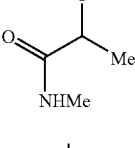 | 103–105 | | | 438 (M + H)+ | FAB | A9, B1a |
| 54 | 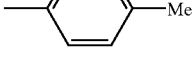 | 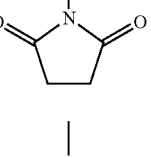 | 118–120 | | | 384 (M + H)+ | FAB | A9, B1a |
| 55 | 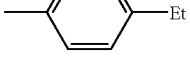 | 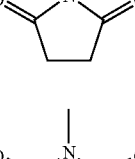 | 125–128 | | | 394 (M + H)+ | FAB | A1, B1a |
| 56 | 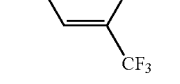 | 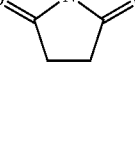 | 227–230 | | | 468 (M + H)+ | FAB | A1, B1a |
| 57 | 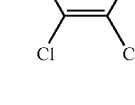 | | 154–156 | | | 434 (M + H)+ | FAB | A1, B1a |

TABLE 1-continued

2-Substituted-5-tert-butylphenyl Ureas

| Example | R¹ | R² | mp (° C.) | TLC R$_f$ | Solvent System | Mass Spec. | Source | Synth. Method |
|---|---|---|---|---|---|---|---|---|
| 58 | 3-methoxytetrahydrofuran | 4-F-phenyl | 169–171 | | | 373 (M + H)+ | FAB | A2, B1a |
| 59 | 3-methoxytetrahydrofuran | 2,3-diCl-phenyl | 157–159 | | | 423 (M + H)+ | FAB | A2, B1a |
| 60 | 3-methoxytetrahydrofuran | 4-Me-phenyl | 229–231 | | | 369 (M + H)+ | FAB | A2, B1a |
| 61 | N(SO₂Me)₂ | 4-Et-phenyl | 200–204 | | | 468 (M + H)+ | FAB | B2a |
| 62 | N(SO₂Me)₂ | 2,3-diCl-phenyl | 187–188 | | | 508 (M + H)+ | FAB | B2a |
| 63 | phenyl | 2,3-diCl-phenyl | 204–206 | | | 413 (M + H)+ | FAB | B1a |
| 64 | 3-OMe-phenyl | 4-Me-phenyl | 192–194 | | | 389 (M + H)+ | FAB | A7, B1a |
| 65 | 3-OMe-phenyl | 1-naphthyl | 183–185 | | | 425 (M + H)+ | FAB | A7, B1a |

TABLE 1-continued

2-Substituted-5-tert-butylphenyl Ureas

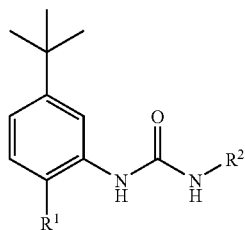

| Example | R¹ | R² | mp (°C.) | TLC R$_f$ | Solvent System | Mass Spec. | Source | Synth. Method |
|---------|----|----|----------|-----------|----------------|------------|--------|---------------|
| 66 | 3-OMe-phenyl | 2,3-diCl-phenyl | 159–160 | | | 443 (M + H)+ | FAB | A7, B1a |
| 67 | 3-OMe-phenyl | 2,4-diF-phenyl | 179–180 | | | 411 (M + H)+ | FAB | A7, B1a |
| 68 | 3-F-phenyl | 4-NO₂-phenyl | | 0.06 | 10% EtOAc/90% hexane | 408 (M + H)+ | FAB | A7, B1a |
| 69 | 4-Me-phenyl | 4-Me-phenyl | 227–229 | | | 377 (M + H)+ | FAB | A7, B1a |
| 70 | 4-Me-phenyl | 4-F-phenyl | 216–217 | | | 381 (M + H)+ | FAB | A7, B1a |
| 71 | 4-Me-phenyl | 2,3-diCl-phenyl | 213–214 | | | 431 (M + H)+ | FAB | A7, B1a |
| 72 | 4-Me-phenyl | 2,4-diF-phenyl | 200–201 | | | 399 (M + H)+ | FAB | A7, B1a |
| 73 | 3-methylthiophene | 4-(pyridin-4-yloxy)phenyl | 134–136 | | | 443 (M+) | EI | A7, B1a |
| 74 | 3-methylthiophene | 3-(pyridin-4-ylthio)phenyl | 185-186 | | | 459 (M + H)+ | FAB | A7, B1a |

TABLE 1-continued

2-Substituted-5-tert-butylphenyl Ureas

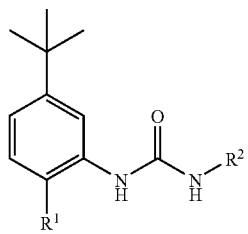

| Example | R¹ | R² | mp (° C.) | TLC R_f | Solvent System | Mass Spec. | Source | Synth. Method |
|---|---|---|---|---|---|---|---|---|
| 75 | 3-methylthiophene | 2,3-dichlorophenyl | 207–208 | | | 419 (M + H)+ | FAB | A7, B1a |

TABLE 2

2-Substituted-5-(trifluoromethyl)phenyl Ureas

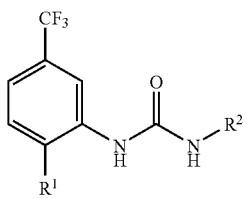

| Example | R¹ | R² | mp (° C.) | TLC R_f | Solvent System | Mass Spec. | Source | Synth. Method |
|---|---|---|---|---|---|---|---|---|
| 76 | OMe | 4-methylphenyl | 185–186 | | | 325 (M + H)+ | FAB | B1d |
| 77 | OMe | 4-fluorophenyl | | 0.22 | 20% EtOAc/80% hexane | 329 (M + H)+ | FAB | B3b |
| 78 | OMe | 2-fluoro-4-methylphenyl | | 0.49 | 20% EtOAc/80% hexane | 343 (M + H)+ | FAB | B3b |
| 79 | OMe | 4-fluoro-3-methylphenyl | | 0.32 | 20% EtOAc/80% hexane | 343 (M + H)+ | FAB | B3b |
| 80 | OMe | 2-chloro-4-methylphenyl | | 0.37 | 20% EtOAc/80% hexane | 359 (M + H)+ | FAB | B3b |

TABLE 2-continued

2-Substituted-5-(trifluoromethyl)phenyl Ureas

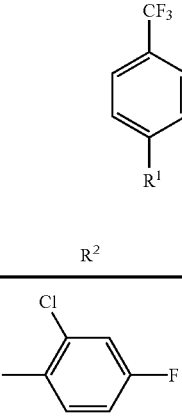

| Example | R¹ | R² | mp (° C.) | TLC R$_f$ | Solvent System | Mass Spec. | Source | Synth. Method |
|---|---|---|---|---|---|---|---|---|
| 81 | OMe | 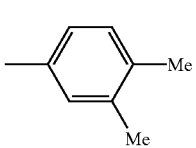 | | 0.44 | 20% EtOAc/80% hexane | 363 (M + H)+ | FAB | B3b |
| 82 | OMe | 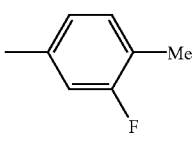 | | 0.68 | 50% EtOAc/50% hexane | 339 (M + H)+ | FAB | B1d |
| 83 | OMe | 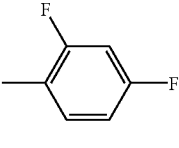 | | 0.68 | 50% EtOAc/50% hexane | 343 (M + H)+ | FAB | B1d |
| 84 | OMe | 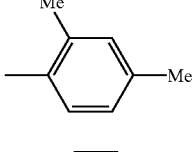 | | 0.60 | 50% EtOAc/50% hexane | 347 (M + H)+ | FAB | B1d |
| 85 | OMe | 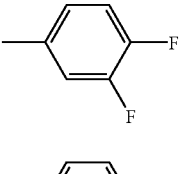 | | 0.53 | 2% MeOH/98% CH2Cl2 | 339 (M + H)+ | FAB | B1d |
| 86 | OMe | 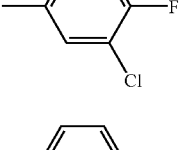 | | 0.29 | 2% MeOH/98% CH2Cl2 | 347 (M + H)+ | FAB | B1d |
| 87 | OMe | 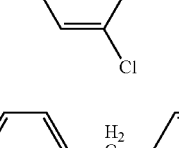 | | 0.27 | 2% MeOH/98% CH2Cl2 | 363 (M + H)+ | FAB | B1d |
| 88 | OMe | 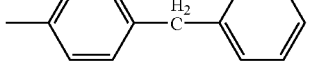 | | 0.45 | 2% MeOH/98% CH2Cl2 | 359 (M + H)+ | FAB | B1d |
| 89 | OMe |  | 184–185 | | | 401 (M + H)+ | FAB | B2a |

TABLE 2-continued

2-Substituted-5-(trifluoromethyl)phenyl Ureas

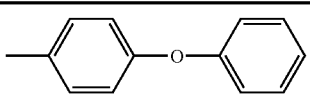

| Example | R¹ | R² | mp (° C.) | TLC R$_f$ | Solvent System | Mass Spec. | Source | Synth. Method |
|---|---|---|---|---|---|---|---|---|
| 90 | OMe | 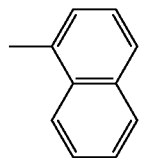 | 176–178 | | | 402 (M+) | EI | B1a |
| 91 | OMe | 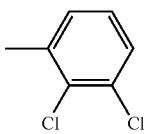 | 231–233 | | | 361 (M + H)+ | FAB | B1a |
| 92 | OMe | 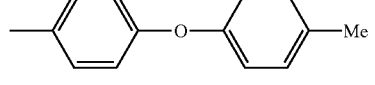 | 192–194 | | | 379 (M + H)+ | FAB | B1a |
| 93 | OMe | 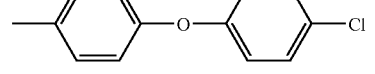 | 198 | | | 417 (M + H)+ | FAB | B1e |
| 94 | OMe | 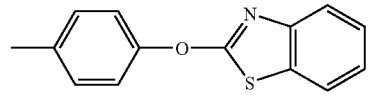 | 206 | 0.58 | 5% acetone/95% CH2Cl2 | 437 (M + H)+ | FAB | B2a |
| 95 | OMe | 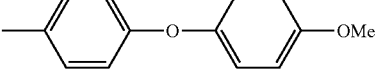 | 98-99 | 0.50 | 5% acetone/95% CH2Cl2 | | | B2a |
| 96 | OMe | 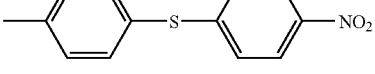 | 190 | 0.65 | 5% acetone/95% CH2Cl2 | | | B2a |
| 97 | OMe | 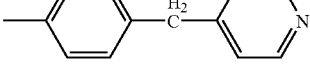 | 194 | 0.76 | 5% acetone/95% CH2Cl2 | 464 (M + H)+ | FAB | B2a |
| 98 | OMe | 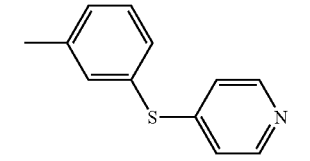 | 210–211 | 0.07 | 5% acetone/95% CH2Cl2 | 402 (M + H)+ | FAB | B2a |
| 99 | OMe | 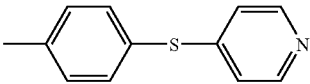 | 202 | 0.09 | 5% acetone/95% CH2Cl2 | 420 (M + H)+ | FAB | B2a |
| 100 | OMe |  | 215 | 0.08 | 5% acetone/95% CH2Cl2 | 420 (M + H)+ | FAB | B2a |

TABLE 2-continued

2-Substituted-5-(trifluoromethyl)phenyl Ureas

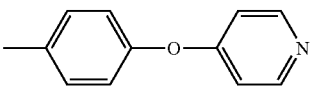

| Example | R¹ | R² | mp (° C.) | TLC $R_f$ | Solvent System | Mass Spec. | Source | Synth. Method |
|---|---|---|---|---|---|---|---|---|
| 101 | OMe | 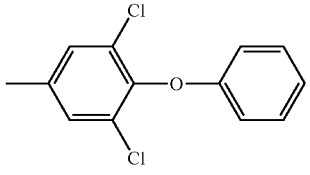 | 206 | 0.05 | 5% acetone/95% CH2Cl2 | 404 (M + H)+ | FAB | B2a |
| 102 | OMe | 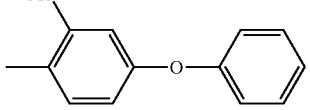 |  | 0.78 | 5% acetone/95% CH2Cl2 | 471 (M + H)+ | FAB | B1a |
| 103 | OMe | 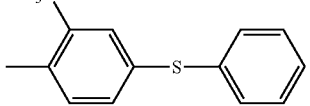 |  |  |  | 471 (M + H)+ | FAB | B1a |
| 104 | OMe | 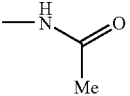 |  |  |  | 487 (M + H)+ | FAB | B1a |
| 105 | 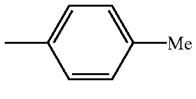 |  |  | 0.65 | 20% EtOAc/80% hexane | 352 (M + H)+ | FAB | B1d |
| 106 | 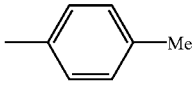 |  | 159-160 | 0.33 | 25% EtOAc/75% hexane | 353 (M + H)+ | FAB | A5, B1a |
| 107 | 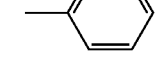 | 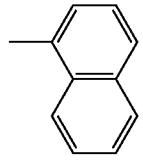 | 152-153 | 0.35 | 25% EtOAc/75% hexane | 339 (M + H)+ | FAB | A5, B1a |
| 108 | SMe | 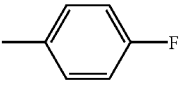 | 246-247 | 0.30 | 25% EtOAc/75% hexane | 377 (M + H)+ | FAB | B1a |
| 109 | SMe | 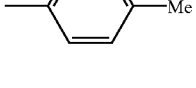 | 210-211 | 0.35 | 25% EtOAc/75% hexane | 345 (M + H)+ | CI | B1a |
| 110 | SMe |  | 195-196 | 0.35 | 25% EtOAc/75% hexane | 314 (M + H)+ | FAB | B1a |

TABLE 2-continued

2-Substituted-5-(trifluoromethyl)phenyl Ureas

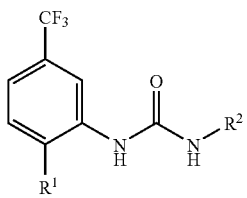

| Example | R¹ | R² | mp (° C.) | TLC $R_f$ | Solvent System | Mass Spec. | Source | Synth. Method |
|---|---|---|---|---|---|---|---|---|
| 111 | SMe | (2,3-dichlorophenyl) | 196–197 | 0.40 | 25% EtOAc/75% hexane | 395 (M + H)+ | FAB | B1a |

TABLE 3

S-Substituted 2-Methoxy-5-sulfonylphenyl Ureas

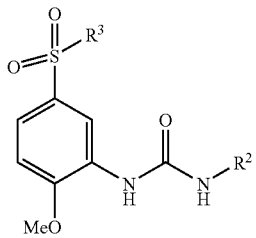

| Example | R² | R³ | mp (° C.) | TLC $R_f$ | Solvent System | Mass Spec. | Source | Synth. Method |
|---|---|---|---|---|---|---|---|---|
| 112 | 4-Me-phenyl | F | 205-207 | | | 339 (M + H)+ | HPLC ES-MS | B1d |
| 113 | 4-Me-phenyl | CHF₂ | 195-196 | | | 370 (M+) | EI | B1d |
| 114 | 4-F-3-Me-phenyl | CHF₂ | | 0.46 | 50% EtOAc/50% hexane | 389 (M + H)+ | FAB | B3a |
| 115 | 3-Cl-4-Me-phenyl | CHF₂ | | 0.21 | 50% EtOAc/50% hexane | 405 (M + H)+ | FAB | B3a |
| 116 | 3-Cl-4-F-phenyl | CHF₂ | | 0.23 | 20% EtOAc/80% hexane | 409 (M + H)+ | FAB | B3a |

TABLE 3-continued

S-Substituted 2-Methoxy-5-sulfonylphenyl Ureas

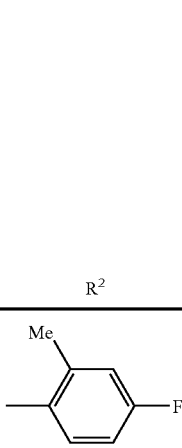

| Example | R² | R³ | mp (° C.) | TLC R_f | Solvent System | Mass Spec. | Source | Synth. Method |
|---|---|---|---|---|---|---|---|---|
| 117 | 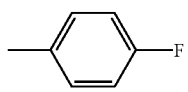 | CHF₂ | | 0.40 | 50% EtOAc/50% hexane | 389 (M + H)+ | FAB | B3a |
| 118 | 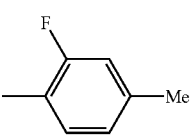 | CHF₂ | | 0.53 | 50% EtOAc/50% hexane | 375 (M + H)+ | FAB | B3a |
| 119 | 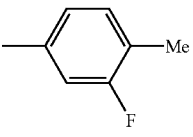 | CHF₂ | | 0.58 | 50% EtOAc/50% hexane | 389 (M + H)+ | FAB | B1c |
| 120 | 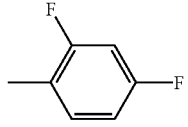 | CHF₂ | | 0.48 | 50% EtOAc/50% hexane | 389 (M + H)+ | FAB | B1d |
| 121 | 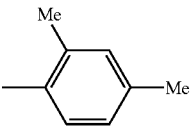 | CHF₂ | | 0.44 | 50% EtOAc/50% hexane | 393 (M + H)+ | FAB | B1c |
| 122 | 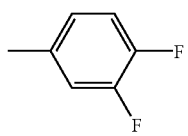 | CHF₂ | | 0.33 | 5% MeOH/95% CH2Cl2 | 385 (M + H)+ | FAB | B1c |
| 123 | 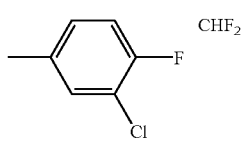 | CHF₂ | | | | 393 (M + H)+ | FAB | B1c |
| 124 | 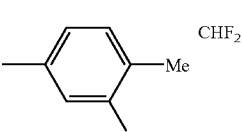 | CHF₂ | | | | 409 (M + H)+ | FAB | B1c |
| 125 | | CHF₂ | | | | 405 (M + H)+ | FAB | B1c |

TABLE 3-continued

S-Substituted 2-Methoxy-5-sulfonylphenyl Ureas

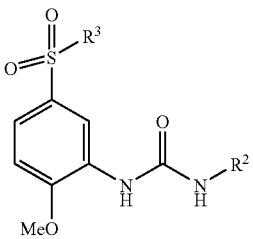

| Example | R² | R³ | mp (° C.) | TLC R$_f$ | Solvent System | Mass Spec. | Source | Synth. Method |
|---|---|---|---|---|---|---|---|---|
| 126 | 2,4-diMe-phenyl | CHF₂ | | 0.56 | 50% EtOAc/50% hexane | 385 (M + H)+ | FAB | B1c |
| 127 | 4-Me-phenyl | CF₃ | | 0.56 | 50% EtOAc/50% hexane | 389 (M + H)+ | FAB | A3, B1d |

TABLE 4

3-Substituted-2-naphthyl Ureas

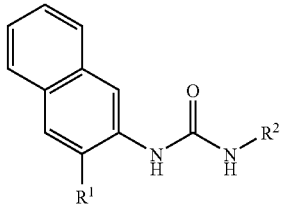

| Example | R¹ | R² | mp (° C.) | TLC R$_f$ | Solvent System | Mass Spec. | Source | Synth. Method |
|---|---|---|---|---|---|---|---|---|
| 128 | OMe | 4-Me-phenyl | 171–172 | 0.40 | 25% EtOAc/75% hexane | 307 (M + H)+ | FAB | B4 |
| 129 | OMe | 2-Me-3-F-phenyl | 197–199 | 0.40 | 14% EtOAc/86% hexane | 325 (M + H)+ | FAB | B4 |
| 130 | OMe | 1-naphthyl | 235–236 | 0.45 | 25% EtOAc/75% hexane | 343 (M + H)+ | FAB | A6, B1a |
| 131 | OMe | 4-F-phenyl | 236–237 | 0.45 | 25% EtOAc/75% hexane | 311 (M + H)+ | FAB | A6, B1a |

TABLE 4-continued
3-Substituted-2-naphthyl Ureas
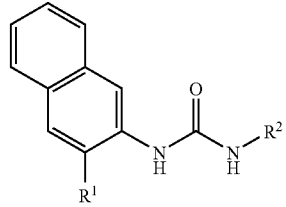
| Example | R¹ | R² | mp (°C.) | TLC R$_f$ | Solvent System | Mass Spec. | Source | Synth. Method |
|---|---|---|---|---|---|---|---|---|
| 132 | OMe | 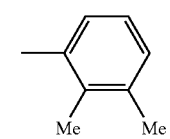 | 209–211 | | | 311 (M + H)+ | FAB | A6, B1a |
| 133 | OMe | 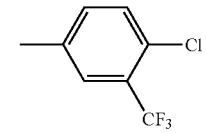 | 225–226 | | | 321 (M + H)+ | FAB | A6, B1a |
| 134 | OMe | 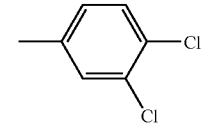 | 199–200 | | | 395 (M + H)+ | FAB | A6, B1a |
| 135 | OMe | 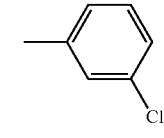 | 227–228 | | | 361 (M + H)+ | FAB | A6, B1a |
| 136 | OMe | 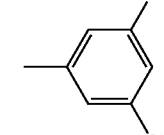 | 207–208 | | | 327 (M + H)+ | FAB | A6, B1a |
| 137 | OMe | 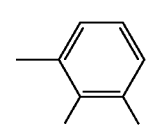 | 234–235 | | | 361 (M + H)+ | FAB | A6, B1a |
| 138 | OMe | 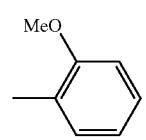 | 228–229 | | | 352 (M + H)+ | FAB | A6, B1a |
| 139 | OMe |  | 190–195 | | | 323 (M + H)+ | FAB | A6, B1a |

TABLE 4-continued

3-Substituted-2-naphthyl Ureas

| Example | R¹ | R² | mp (° C.) | TLC R$_f$ | Solvent System | Mass Spec. | Source | Synth. Method |
|---|---|---|---|---|---|---|---|---|
| 140 | OMe | 3-F-phenyl | 203–205 | | | 310 (M + H)+ | FAB | A6, B1a |
| 141 | OMe | 3-Me-phenyl | 209–210 | | | 307 (M + H)+ | FAB | A6, B1a |
| 142 | OMe | 4-OMe-phenyl | 200–201 | | | 323 (M + H)+ | FAB | A6, B1a |
| 143 | OMe | -CH₂-phenyl | 201–202 | | | 307 (M + H)+ | FAB | A6, B1a |
| 144 | OMe | 4-phenoxyphenyl | 216–218 | | | 385 (M + H)+ | FAB | A6, B1a |
| 145 | OMe | 4-CF₃-phenyl | 181–182 | | | 361 (M + H)+ | FAB | A6, B1a |
| 146 | OMe | 4-(pyridin-4-ylthio)phenyl | 238–239 | 0.25 | 25% EtOAc/75% hexane | 402 (M + H)+ | FAB | B4 |
| 147 | OMe | 4-(pyridin-4-ylmethyl)phenyl | 199–200 | 0.20 | 25% EtOAc/75% hexane | 384 (M + H)+ | FAB | B4 |
| 148 | OMe | 4-Et-phenyl | 175–176 | | | 321 (M + H)+ | FAB | A6, B1a |

TABLE 4-continued
3-Substituted-2-naphthyl Ureas
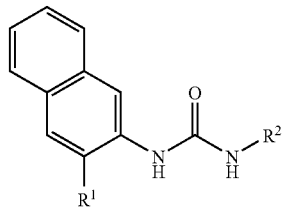
| Example | R[1] | R[2] | mp (° C.) | TLC R$_f$ | Solvent System | Mass Spec. | Source | Synth. Method |
|---|---|---|---|---|---|---|---|---|
| 149 | OMe | | 164–166 | | | 544 (M + H)+ | FAB | A6, B1a |
| 150 | OMe | | 206–209 | | | 446 (M + H)+ | FAB | A6, B1a |
| 151 | OMe | | 234–237 | | | 410 (M + H)+ | FAB | B2a |
| 152 | OMe | | 209–211 | 0.40 | 25% EtOAc/75% hexane | 414 (M+) | EI | B4 |
TABLE 5
Misc. Ureas
| Example | R[2] | mp (° C.) | TLC R$_f$ | Solvent System | Mass Spec. | Source | Synth. Method |
|---|---|---|---|---|---|---|---|
| 153 | | 183–184 | | | 327 (M + H)+ | FAB | B1d |

TABLE 5-continued

Misc. Ureas

| Example | R² | mp (° C.) | TLC R_f | Solvent System | Mass Spec. | Source | Synth. Method |
|---|---|---|---|---|---|---|---|
| 154 | (structure: 5-sec-butyl-2-methoxyphenyl urea with p-tolyl) | 156–157 | | | 312 (M+) | EI | B1d |
| 155 | (structure: 5-chloro-2-methoxyphenyl urea with p-tolyl) | | 0.46 | 50% EtOAc/50% hexane | 291 (M + H)+ | FAB | B1d |
| 156 | (structure: 4-chloro-5-nitro-2-hydroxyphenyl urea with phenyl) | | | | | | |
| 157 | (structure: 4-chloro-5-nitro-2-hydroxyphenyl urea with 4-(pyridin-4-ylmethyl)phenyl) | | 0.40 | 50% acetone/50% CH2Cl2 | 399 (M + H)+ | FAB | B5 |
| 158 | (structure: 4-chloro-5-nitro-2-methoxyphenyl urea with p-tolyl) | 219–221 | | | 336 (M + H)+ | FAB | B1d |
| 159 | (structure: 4-chloro-5-methyl-2-methoxyphenyl urea with p-tolyl) | 204–205 | | | 305 (M + H)+ | FAB | B1d |
| 160 | (structure: 5-nitro-2-methoxyphenyl urea with p-tolyl) | 208–210 | | | 302 (M + H)+ | FAB | B1d |

TABLE 5-continued

Misc. Ureas

| Example | R² | mp (°C.) | TLC R_f | Solvent System | Mass Spec. | Source | Synth. Method |
|---|---|---|---|---|---|---|---|
| 161 | (4-MeO, 2-MeO, 5-CF3-phenyl)-NH-C(O)-NH-(4-Me-phenyl) | 226–228 | | | 355 (M + H)+ | FAB | B1d |
| 162 | (4-Me, 2-MeO-phenyl)-NH-C(O)-NH-(4-Me-phenyl) | 160–162 | | | 328 (M + H)+ | FAB | B1a |
| 163 | (4-Cl, 2-MeO-phenyl)-NH-C(O)-NH-(4-Me-phenyl) | | 0.85 | 50% EtOAc/50% hexane | 291 (M + H)+ | FAB | B1b |
| 164 | (4-tBu, 2-MeO-phenyl)-NH-C(O)-NH-(2,3-diCl-phenyl) | 225–226 | 0.60 | 25% EtOAc/75% hexane | 367 (M + H)+ | FAB | A4, B1a |
| 165 | (4-Cl, 3-CF3-phenyl)-NH-C(O)-NH-(4-Cl, 3-CF3-phenyl) | | 0.55 | 3% MeOH/97% CH2Cl2 | 417 (M + H)+ | FAB | B6 |
| 166 | (4-Cl, 3-CF3-phenyl)-NH-C(O)-NH-(4-phenoxy-phenyl) | 169–171 | | | 407 (M + H)+ | FAB | B1a |
| 167 | (5-tBu, 2-MeO-phenyl)-NH-C(S)-NH-(1-naphthyl) | 158–160 | | C3 | 365 (M + H)+ | FAB | C3 |

BIOLOGICAL EXAMPLES

P38 Kinase Assay:

The in vitro inhibitory properties of compounds were determined using a p38 kinase inhibition assay. P38 activity was detected using an in vitro kinase assay run in 96-well microtiter plates. Recombinant human p38 (0.5 μg/mL) was mixed with substrate (myelin basic protein, 5 μg/mL) in kinase buffer (25 mM Hepes, 20 mM MgCl$_2$ and 150 mM NaCl) and compound. One μCi/well of $^{33}$P-labeled ATP (10 μM) was added to a final volume of 100 μL. The reaction was run at 32° C. for 30 min. and stopped with a 1M HCl solution. The amount of radioactivity incorporated into the substrate was determined by trapping the labeled substrate onto negatively charged glass fiber filter paper using a 1% phosphoric acid solution and read with a scintillation counter. Negative controls include substrate plus ATP alone.

All compounds exemplified displayed p38 $IC_{50}$s of between 1 nM and 10 μM.

LPS Induced TNFα Production in Mice:

The in vivo inhibitory properties of selected compounds were determined using a murine LPS induced TNFα production in vivo model. BALB/c mice (Charles River Breeding Laboratories; Kingston, N.Y.) in groups of ten were treated with either vehicle or compound by the route noted. After one hour, endotoxin (*E. coli* lipopolysaccharide (LPS) 100 μg) was administered intraperitoneally (i.p.). After 90 min, animals were euthanized by carbon dioxide asphyxiation and plasma was obtained from individual animals by cardiac punture ionto heparinized tubes. The samples were clarified by centrifugation at 12,500×g for 5 min at 4° C. The supernatants were decanted to new tubes, which were stored as needed at −20° C. TNFα levels in sera were measured using a commercial murine TNF ELISA kit (Genzyme).

The preceeding examples can be repeated with similar success by substituting the generically of specifically described reactants and/or operating conditions of this invention for those used in the preceeding examples.

From the foregoing discussion, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

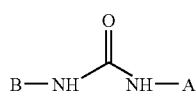

wherein A is

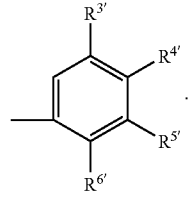

B is naphthyl substituted by —Q—Ar and optionally substituted by one or more substituents which is selected from the group consisting of halogen, up to per-halo, and $W_n$, wherein n is 0-2 and each W is independently —CN, —$CO_2R^7$, —$C(O)NR^7R^7$, —C(O)—$R^7$, —$NO_2$, —$OR^7$, —$SR^7$, —$NR^7R^7$, —$NR^7C(O)OR^7$, —$NR^7C(O)R^7$, $C_1$-$C_{10}$ alkyl, $C_{2-10}$-alkenyl, $C_{1-10}$-alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_{2-10}$-alkenyl, substituted $C_{1-10}$-alkoxy, substituted $C_3$-$C_{10}$ cycloalkyl, substituted $C_4$-$C_{23}$ alkheteroaryl or Q-Ar;

wherein if W is a substituted group, it is substituted by one or more substituents which is independently of —CN, —$CO_2R^7$, —$C(O)R^7$, —$C(O)NR^7R^7$, —$OR^7$, —$SR^7$, —$NR^7R^7$, $NO_2$, —$NR^7C(O)R^7$, —$NR^7C(O)OR^7$ or halogen up to per-halo;

wherein each $R^7$ is independently H, $C_1$-$C_{10}$ alkyl, $C_{2-10}$-alkenyl, $C_3$-$C_{10}$ cycloalkyl, up to per-halosubstituted $C_2$-$C_{10}$ alkyl, up to per-halosubstituted $C_{2-10}$-alkenyl or up to per-halosubstituted $C_3$-$C_{10}$ cycloalkyl, wherein Q is —O—, —S—, —$N(R^7)$—, —$(CH_2)_m$—, —C(O)—, —CH(OH)—, —$(CH_2)_mO$—, —$NR^7C(O)NR^7R^7$—, —$NR^7C(O)$—, —$C(O)NR^7$—, —$(CH_2)_mS$—, —$(CH_2)_mN(R^7)$—, —$O(CH_2)_m$—, —$CHX^a$—, —$CX^a_2$—, —S—$(CH_2)_m$— or —$N(R^7)(CH_2)_m$—, m=1-3, and $X^a$ is halogen; and Ar is a 5-10 member aromatic structure containing 1-2 members of the group consisting of nitrogen, oxygen and sulfur, which is unsubstituted or substituted by halogen up to per-halo and substituted by $Z_{n1}$, wherein $n1$ is 1 to 3 and each Z is independently —CN, —C(O) $NR^7R^7$, —$COR^7$, —$NR^7C(O)OR^7$, —$NR^7C(O)R^7$, substituted $C_1$-$C_{10}$ alkyl or substituted $C_3$-$C_{10}$ cycloalkyl wherein the one or more substituents of the substituted $C_1$-$C_{10}$ alkyl and substituted $C_1$-$C_{10}$ cycloalkyl is are —CN, —$C(O)NR^7R^7$, —$NR^7C(O)R^7$ or —$NR^7C(O)OR^7$, $R^{3'}$, $R^{4'}$, $R^{5'}$ are each independently H, $C_1$-$C_{10}$-alkyl, optionally substituted by halogen, up to perhalo, $C_{1-10}$ alkoxy, optionally substituted by halogen, up to perhaloalkoxy, halogen; $NO_2$ or $NH_2$;

$R^{6'}$ is H, $C_{1-10}$-alkyl, $C_{1-10}$ alkoxy, —$NHCOR^1$; —$NR^1COR^1$; or $NO_2$;

one of $R^{4'}$, $R^{5'}$ or $R^{6'}$ can be -X-Y, or 2 adjacent $R^{4'}$, $R^{5'}$, or $R^{6'}$ can together be an aryl or hetaryl ring with 5-12 atoms, optionally substituted by $C_{1-10}$-alkyl, $C_{1-10}$ alkoxy, $C_{3-10}$ cycloalkyl, $C_{2-10}$ alkenyl, $C_{1-10}$ alkanoyl, $C_{6-12}$ aryl, $C_{5-12}$ hetaryl or $C_{6-12}$ aralkyl;

$R^1$ is $C_{1-10}$-alkyl optionally substituted by halogen, up to perhalo;

X is —$CH_2$—, —S—, —$N(CH_3)$—, —NHC(O)—, —$CH_2$—S—, —S—$CH_2$—, —C(O)—, or —O—; and X is additionally a single bond where Y is pyridyl;

Y is phenyl, pyridyl, naphthyl, pyridone, pyrazine, benzodioxane, benzopyridine, pyrimidine or benzothiazole, each optionally substituted by $C_{1-10}$-alkyl, $C_{1-10}$-alkoxy, halogen, OH, —$SCH_3$ or $NO_2$ or, where Y is phenyl, by

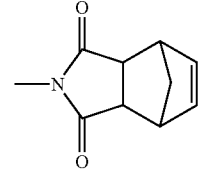

or a pharmaceutically acceptable salt thereof.

2. A compound according to claim 1, wherein $R^1$ is H, halogen, $C_{1-10}$-alkyl optionally substituted by halogen, up to perhalo, $NO_2$, —$SO_2F$ or —$SO_2CF_3$;

$R^4$ is H, halogen, $C_{1-10}$-alkyl, $C_{1-10}$-alkoxy, or $NO_2$;

$R^5$ is H or $C_{1-10}$-alkyl optionally substituted by halogen, up to perhalo;

$R^6$ is H, $C_{1-10}$-alkoxy optionally substituted by at least one hydroxy group: —$COOR^1$; $OR^{1a}CONHR^1$; —$NHCOR^1$; —$SR^1$; phenyl optionally substituted by halo or $C_{1-10}$-alkoxy; $NH_2$; or $N(SO_2R^1)_2$.

3. A compound according to claim 1, wherein $R^4$ is $C_{1-10}$-alkyl or halogen; $R^5$ is H, $C_{1-10}$-alkyl, halogen, $CF_3$, $NO_2$ or $NH_2$; and $R^6$ is H, $C_{1-10}$-alkyl, $C_{1-10}$ alkoxy or halogen.

4. A compound according to claim 1, wherein $R^5$ is $C_{1-10}$-alkyl, halogen, $CF_3$, halogen, $NO_2$ or $NH_2$.

5. A compound according to claim 1, wherein $R^6$ is $C_{1-10}$-alkyl, $C_{1-10}$ alkoxy halogen, $NHCOCH_3$ or $—N(CH_3)COCH_3$.

6. A compound according to claim 1, wherein $R^3$ is t-butyl or $CF_3$ and $R^6$ is $OCH_3$.

7. A compound according to claim 1 wherein $R^1$ is $C_{1-10}$-alkyl or halogen; $R^5$ is H, $C_{1-10}$-alkyl, halogen, $CF_3$, $NO_2$ or $NH_2$; and $R^{6'}$ is H, $C_{1-10}$-alkyl, halogen, $—NHCOCH_3$, $—N(CH_3)COCH_3$, or $NO_2$.

8. A compound according to claim 1 wherein $R^3$ is t-butyl or $CF_3$, $R^4$ is H or halogen, and $R^6$ is H or $—OCH_3$.

9. A pharmaceutical composition comprising a compound of claim 1, and a physiologically acceptable carrier.

10. A pharmaceutical composition comprising a compound of claim 8, and a physiologically acceptable carrier.

11. A compound as in claim 1 wherein $R^3$ is hydrogen, halogen, $C_1$-$C_{10}$-alkyl substituted by halogen up to perhalo, $C_1$-$C_{10}$ alkoxy substituted by halogen up to perhalo, $NHCOR^1$, $—NR^{4a}COR$, $SO_2R$, $NR^1CONR^1$, or $—SO_2CH_pX^a_{tp}$.

12. A compound as in claim 1 wherein $R^3$ is hydrogen, Cl, F, $C_{4-5}$ branched alkyl, $—SO_2F$, $—SO_2CF_3$ or $—CF_3$.

13. A compound as in claim 1 wherein $R^3$ is t-butyl, $—CF_3$, hydrogen, $—SO_2CHF_2$ or $SO_2F$.

14. A compound as in claim 1 wherein $R^6$ is independently H; halogen; $C_{1-10}$-alkyl optionally substituted by halogen up to perhalo; $C_{1-10}$-alkoxy optionally substituted by at least one hydroxy group; $NO_2$; $—SO_2CH_2H$; $—COOR^1$; $—OR^{1a}CONHR^1$; $—SR^1$; $—NH_2$; $—N(SO_2R^1)_2$, $—NR^1COR$, thiophene or phenyl substituted by halogen or alkoxy.

15. A compound as in claim 1 wherein $R^6$ is phenyl substituted by halo or $C_{1-10}$ alkoxy, $NH_2$, $—N(SO_2R^1)_2$, 2,5-dioxo-1-pyrolidinyl, thiophene, $—SR^1$, $COOR^1$ or $—OR^{1a}CONHR^1$.

16. A pharmaceutical composition comprising a compound of claim 13, and a physiologically acceptable carrier.

17. A pharmaceutical composition comprising a compound of claim 14, and a physiologically acceptable carrier.

18. A compound according to claim 1, wherein phenyl and Ar is a 5-10 member aromatic structure containing nitrogen.

19. A compound according to claim 1, wherein Ar is pyridyl.

20. A compound according of claim 8, wherein Ar is pyridyl.

21. A pharmaceutical composition comprising a compound of claim 19, and a physiologically acceptable carrier.

* * * * *

UNITED STATES PATENT AND TRADEMARK OFFICE
CERTIFICATE OF CORRECTION

PATENT NO. : 7,517,880 B2
APPLICATION NO. : 10/060396
DATED : April 14, 2009
INVENTOR(S) : Scott Miller et al.

It is certified that error appears in the above-identified patent and that said Letters Patent is hereby corrected as shown below:

Column 97, line 40 reads

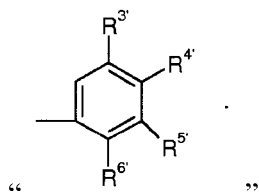

" "

should read

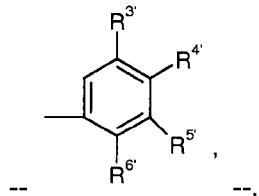

-- --.

Column 97, line 60 reads "or more substituents which is independently of -CN,"

should read -- or more substituents which is independently -CN, --.

Column 97, line 66 reads "$C_2$-$C_{10}$ alkyl, up to per-halosubstituted $C_{2-10}$-alkenyl or"

should read -- $C_{1-10}$ alkyl, up to per-halosubstituted $C_{2-10}$-alkenyl or --.

Column 98, line 16 reads "substituted $C_1$-$C_{10}$ alkyl and substituted $C_{1-10}$"

should read -- substituted $C_1$-$C_{10}$ alkyl and substituted $C_3$-$C_{10}$ --.

Signed and Sealed this
Seventh Day of February, 2012

David J. Kappos
*Director of the United States Patent and Trademark Office*

CERTIFICATE OF CORRECTION (continued)
U.S. Pat. No. 7,517,880 B2

Column 98, line 17 reads "cycloalkyl is are -CN, -C(O)NR$^7$R$^7$, -NR$^7$C(O)R$^7$"

should read -- cycloalkyl is -CN, -C(O)NR$^7$R$^7$, -NR$^7$C(O)R$^7$ --.

Column 98, line 19 reads "R$^{3'}$, R$^{4'}$, R$^{5'}$ are each independently H, C$_1$-C$_{10}$-alkyl,"

should read -- R$^{3'}$, R$^{4'}$, R$^{5'}$ are each independently H, C$_{1-10}$-alkyl, --.

Column 98, line 53 reads "R$^1$ is H, halogen, C$_{1-10}$-alkyl optionally substituted by"

should read -- R$^{3'}$ is H, halogen, C$_{1-10}$-alkyl optionally substituted by --.

Column 98, line 55 reads "R$^4$ is H, halogen C$_{1-10}$-alkyl, C$_{1-10}$-alkoxy, or NO$_2$;"

should read -- R$^{4'}$ is H, halogen C$_{1-10}$-alkyl, C$_{1-10}$-alkoxy, or NO$_2$; --.

Column 98, line 56 reads "R$^5$ is H or C$_{1-10}$-alkyl optionally substituted by halogen, up"

should read -- R$^{5'}$ is H or C$_{1-10}$-alkyl optionally substituted by halogen, up --.

Column 98, line 58 reads "R$^6$ is H, C$_{1-10}$-alkoxy optionally substituted by at least one"

should read -- R$^{6'}$ is H, C$_{1-10}$-alkoxy optionally substituted by at least one --.

Column 98, line 59 reads "hydroxy group: -COOR$^1$; OR$^{1a}$CONHR$^1$; -NH-"

should read -- hydroxy group; -COOR$^1$; -OR$^{1a}$CONHR$^1$; -NH- --.

Column 98, line 62 reads "3. A compound according to claim 1, wherein R$^4$ is C$_{1-10}$-"

should read -- 3. A compound according to claim 1, wherein R$^{4'}$ is C$_{1-10}$- --.

CERTIFICATE OF CORRECTION (continued)
U.S. Pat. No. 7,517,880 B2

Column 98, line 63 reads "alkyl or halogen; $R^5$ is H, $C_{1-10}$-alkyl, halogen, $CF_3$, $NO_2$ or"

should read -- alkyl or halogen; $R^{5'}$ is H, $C_{1-10}$-alkyl, halogen, $CF_3$, $NO_2$ or --.

Column 98, line 64 reads "$NH_2$; and $R^6$ is H, $C_{1-10}$ alkoxy or halogen."

should read -- $NH_2$; and $R^{6'}$ is H, $C_{1-10}$ alkoxy or halogen --.

Column 98, line 65 reads "4. A compound according to claim 1, wherein $R^5$ is $C_{1-10}$-"

should read -- 4. A compound according to claim 1, wherein $R^{5'}$ is $C_{1-10}$- --.

Column 99, line 1 reads "5. A compound according to claim 1, wherein $R^6$ is $C_{1-10}$-"

should read -- 5. A compound according to claim 1, wherein $R^{6'}$ is $C_{1-10}$- --.

Column 99, line 2 reads "alkyl, $C_{1-10}$ alkoxy halogen, $NHCOCH_3$ or -$N(CH_3)$"

should read -- alkyl, $C_{1-10}$ alkoxy, halogen, -$NHCOCH_3$ or -$N(CH_3)$ --

Column 99, line 4 reads "6. A compound according to claim 1, wherein $R^3$ is t-butyl"

should read -- 6. A compound according to claim 1, wherein $R^{3'}$ is t-butyl --.

Column 99, line 5 reads "or $CF_3$ and $R^6$ is $OCH_3$."

should read -- or $CF_3$ and $R^{6'}$ is $OCH_3$. --.

Column 99, line 6 reads "7. A compound according to claim 1 wherein $R^1$ is $C_{1-10}$-"

should read -- 7. A compound according to claim 1, wherein $R^{4'}$ is $C_{1-10}$- --.

Column 99, line 7 reads "alkyl or halogen; $R^5$ is H, $C_{1-10}$-alkyl, halogen, $CF_3$, $NO_2$ or"

should read -- alkyl or halogen; $R^{5'}$ is H, $C_{1-10}$-alkyl, halogen, $CF_3$, $NO_2$ or --.

Column 99, line 10 reads "8. A compound according to claim 1 wherein $R^3$ is t-butyl"

should read -- 8. A compound according to claim 1, wherein $R^{3'}$ is t-butyl --.

Column 99, line 11 reads "or $CF_3$, $R^4$ is H or halogen, and $R^6$ is H or $-OCH_3$."

should read -- or $CF_3$, $R^{4'}$ is H or halogen, and $R^{6'}$ is H or $-OCH_3$. --.

Column 99, line 16 reads "11. A compound as in claim 1 wherein $R^3$ is hydrogen,"

should read -- 11. A compound as in claim 1 wherein $R^{3'}$ is hydrogen, --.

Column 99, line 19 reads "$NHCOR^1$, $-NR^{4a}COR$, $SO_2R$, $-NR^1CONR^1$, or"

should read -- $-NHCOR^1$, $-NR^{1a}COR^1$, $SO_2F$, $-NR^{1a}CONR^1$, or --.

Column 99, line 20 reads "$-SO_2CH_pX^a_{tp}$."

should read -- $-SO_2CH_pX^a_{3-p}$. --.

Column 99, line 21 reads "12. A compound as in claim 1 wherein $R^3$ is hydrogen, Cl,"

should read -- 12. A compound as in claim 1 wherein $R^{3'}$ is hydrogen, Cl, --.

Column 99, line 23 reads "13. A compound as in claim 1 wherein $R^3$ is t-butyl, $-CF_3$,"

should read -- 13. A compound as in claim 1 wherein $R^{3'}$ is t-butyl, $-CF_3$, --.

CERTIFICATE OF CORRECTION (continued)
U.S. Pat. No. 7,517,880 B2

Column 100, line 1 reads "14. A compound as in claim 1 wherein $R^6$ is independently"

should read -- 14. A compound as in claim 1 wherein $R^{6'}$ is independently --.

Column 100, line 4 reads " hydroxy group; $NO_2$; $-SO_2CH_2H$; $-COOR^1$;"

should read -- hydroxy group; $NO_2$; $-SO_2CF_2H$; $-COOR^1$; --.

Column 100, line 6 reads "$-NR^1COR$, thiophene or phenyl substituted by halogen or"

should read -- $-NR^1COR^1$, thiophene or phenyl substituted by halogen or --.

Column 100, line 8 reads "15. A compound as in claim 1 wherein $R^6$ is phenyl sub-"

should read -- 15. A compound as in claim 1 wherein $R^{6'}$ is phenyl sub- --.

Column 100, line 16 reads "18. A compound according to claim 1, wherein phenyl and"

should read -- 18. A compound according to claim 1, wherein --.

Column 100, line 20 reads "20. A compound according of claim 8, wherein Ar is"

should read -- 20. A compound according to claim 8, wherein Ar is --.